US008030089B2

(12) United States Patent
Geromanos et al.

(10) Patent No.: US 8,030,089 B2
(45) Date of Patent: Oct. 4, 2011

(54) METHOD OF ANALYZING DIFFERENTIAL EXPRESSION OF PROTEINS IN PROTEOMES BY MASS SPECTROMETRY

(75) Inventors: Scott Geromanos, Middletown, NJ (US); Ashok R. Dongre, Newtown, PA (US); Gregory Opiteck, Montreal (CA); Jeffrey Silva, Beverly, MA (US)

(73) Assignee: Micromass UK Limited (GB)

( * ) Notice: Subject to any disclaimer, the term of this patent is extended or adjusted under 35 U.S.C. 154(b) by 712 days.

(21) Appl. No.: 10/893,415

(22) Filed: Jul. 16, 2004

(65) Prior Publication Data

US 2008/0142696 A1      Jun. 19, 2008

Related U.S. Application Data

(63) Continuation of application No. 10/497,896, filed as application No. PCT/GB02/05571 on Dec. 9, 2002, now abandoned.

(60) Provisional application No. 60/364,847, filed on Mar. 14, 2002, provisional application No. 60/340,460, filed on Dec. 8, 2001.

(51) Int. Cl.
*G01N 24/00* (2006.01)

(52) U.S. Cl. .......................................... 436/173; 436/86

(58) Field of Classification Search ........................ None
See application file for complete search history.

(56) References Cited

U.S. PATENT DOCUMENTS

| | | | |
|---|---|---|---|
| 4,735,777 A | 4/1988 | Mitsui et al. | |
| 6,017,693 A | 1/2000 | Yates et al. | |
| 6,835,927 B2 | 12/2004 | Becker et al. | |
| 2002/0115056 A1 | 8/2002 | Goodlett | |
| 2002/0119490 A1 | 8/2002 | Aebersold et al. | |

FOREIGN PATENT DOCUMENTS

| | | |
|---|---|---|
| EP | 1456667 | 5/2006 |
| GB | 2387653 | 10/2003 |
| JP | 2001 330599 | 11/2001 |
| WO | 00/03240 A | 1/2000 |
| WO | WO 00/60361 A3 | 10/2000 |
| WO | WO 01/57518 A3 | 8/2001 |
| WO | 02/052259 | 7/2002 |
| WO | 02/072863 | 9/2002 |

(Continued)

OTHER PUBLICATIONS

Link et al. "Direct analysis of protein complexes using mass spectrometry", Nature Biotechnology, 1999, v. 17, pp. 676-682.*

(Continued)

*Primary Examiner* — Yelena G Gakh
(74) *Attorney, Agent, or Firm* — Diederiks & Whitelaw, PLC

(57) ABSTRACT

A method of identifying molecules of biological origin is disclosed. The molecules are identified and the basis of the accurately determined mass to charge ratio of the molecules and at least a further physico-chemical property such as elution time or charge state. Further physico-chemical properties may be used. The experimentally determined accurate mass and physico-chemical properties can then be compared with a look-up table of information. The look-up table may generated or physico-chemical properties of data in a conventional database may be calculated. The ability to recognize and preferably identify the same molecules in two different samples may be used to determine whether a particular biological molecules has been expressed differently in an experimental sample relative to a control sample.

9 Claims, 33 Drawing Sheets

FOREIGN PATENT DOCUMENTS

WO    WO 03/042774 A2    5/2003

OTHER PUBLICATIONS

Carr et al. "Overview of Peptide and Protein Analysis by Mass Spectrometry", Current Protocols in Protein Science, 1996, pp. 16.1.1-16.1.27.*
Bakhtiar et al. "Mass spectrometry of the proteome", Molecular Pharmacology, 2001, 2001, v.60, pp. 405-415.*
Clauser et al. "Role of Accurate Mass Measurement (±10 ppm) in Protein Identification Strategies Employing MS or MS/MS and Database Searching", Anal. Chem., 1999, v. 71, pp. 2871-2882.*
Stone discloses "Surface-Induced Dissociation on a MALDI-Ion Mobility-Orthogonal Time-of-Flight Mass Spectrometer: Sequencing Peptides from an "In-Solution" Protein Digest", Anal. Chem., 2001, v/ 73, pp. 2233-2236.*
Sequence analysis of peptide mixtures by automated integratin of Edman and mass spectrometric data, R.S. Johnson and K.A. Walsh, Proteing Science (1991), I, 1083-1091.
Quantitative Profiling of Proteins in Complex Mixtures Using Liquid Chromatography and Mass Spectrometry, Dirk Chelius Journal of Proteome Research 202, 1, 317-323.
American Society for Mass Spectrometry: Education, ASMS, What is Mass Spectrometry, p. 1 of 1, last updated Dec. 1, 2001.
Direct analysis of protein complexes using mass spectrometry, Link, et al., Nature Biotechnology, 1999, vol. 17, pp. 676-682.
De Novo Peptide Sequencing via Tandem Mass Spectrometry: A Graph-Theoretical Approach, Dancik, et al., RECOMB '99 , pp. 135-144.
Biomedical applications of two-dimensional electrophoresis using immobilized pH gradients:, S. Hanash, Electrophoresis 2000, 21, 12-02-1209.
Two-dimensional map of the proteome of *Haemophilus influenzae*, Langen, et al., Electrophoresis 2000, 21, 411-429.
"Capillary column high-performance liquid chromatographic-electrospray ionization . . . ", Nakayama, et al., J. Chrom. A, 1996, vol. 730, p. 279-287.
Large-scale analysis of the yeast proteome by multidimensional protein identification technology, Washburn, et al, Nat. Bio., 2001, vol. 19 p. 242-247.
Analysis of the microbial proteome, Washburn et al., Current Opinion in Microbiology, 2000, vol. 3, p. 292-297.
Accurate quantitation of protein expression and site-specific phosphorylation, Oda, et al, Proc. Nat. Aca. Sci. USA 1999.
The N-end rule: Functions, mysteries, uses, A. Varshaysky, Proc. Nat. Acad. Sci. USA, 1996,93 p. 12142-12149.
Rapid identification of proteins by peptide-mass fingerprinting, Pappin, et al., Current Biology 1993, vol. 3, pp. 327-332.
DeRisi, et al., Exploring the Metabolic and Genetic Control of Gene Expression on a Genomic Scale, Science, vol. 278, pp. 680-686.
Roth, et al., "Finding DNA regulatory motifs within unaligned noncoding sequences . . . ", Nature Biotech, 1998, vol. 16, pp. 939-945.
Pandey, et al., Proteomics to study genes and genomes, Nature 2000, vol. 405, pp. 837-846.
John Cottrell, Protein Identification by Peptide Mass Fingerprinting, Peptide Research, 1994, vol. 7 (3) pp. 115-124.
Li, et al., "High-Throughput Peptide Identification from Protein Digests Using . . . ", Anal chem. 2001, vol. 73, pp. 3312-3322.
Shen, et al., "High-Throughput Proteomics Using High-Efficiency Multiple-Capillary . . . ", Anal. Chem. 2001, vol. 73 pp. 3011-3021.
Jensen, et al., "Identification of the Components of Simple Protein Mixtures by High-Accuracy Peptide Mass Mapping . . . ", Anal. Chem., vol. 69, pp. 4741-4750.
Griffin, et al., "Quantitative Proteomic Analysis Using a MALDI Quadrupole . . . ", Anal Chem. 2001, vol. 73 pp. 978-986.
Dongre, Ashok R., et al; Emerging tandem-mass-spectrometry techniques for the rapid identification of proteins; TIBTECH Oct. 1997, (vol. 15); Elsevier Science Ltd 1997; 418-425.
Soskic, V. et al; Functional Proteomics Analysis of Signal Transduction Pathways of the Platelet-Derived Growth Factor Beta Receptor, Biochemistry, American Chemical Society, vol. 38, 1999, pp. 1757-1764.
Perkins, David N. et al; Probability-based protein identification by searching sequence databases using mass spectrometry data; Electrophoresis 1999, vol. 20, pp. 3551-3567.
Gras, Robin, et al; Improving protein identification from peptide mass fingerprinting through a parameterized multi-level scoring algorithm and an optimized peak detection; Electrophoresis 1999, vol. 20, pp. 3535-3550.
Pang, James X. et al; Biomarker Discovery in Urine by Proteomics; Journal of Proteome Research Mar. 2002, vol. 1, No. 2, pp. 161-169.
Gygi, S. P. et al; Quantitative analysis of complex protein mixtures using isotope-coded affinity tags; Nature Biotechnology, vol. 17, No. 10, Oct. 1999, pp. 994-999.
Tempst, Paul, et al; MALDI-TOF Mass Spectrometry in the Protein Biochemistry Lab: From Characterization of Cell Cycle Regulators to the Quest for Novel Antibiotics; Mass Spectrometry In The Biological Sciences; 1995, 105-133.
Thomas, Rexford L. et al, Mass Spectrometric Identification of Increased C16 Ceramide Levels During Apoptosis, The Journal of Biological Chemistry; 1999, pp. 30580-30588, vol. 274, The American Society for Biochemistry and Molecular Biology, Inc.
Fiehn, Oliver et al, Metabolite profiling for plant functional genomics, Nature Biotechnology, 2000, pp. 1157-1161, vol. 18.
Fiehn, Oliver et al, Identification of Uncommon Plant Metabolites Based on Calculation of Elemental Compositions Using Gas Chromatography and Quadrupole Mass Spectrometry, Analytical Chemistry, 2000, pp. 3573-3580, vol. 72, American Chemical Society.
Niwa, Toshimitsu et al, Gas Chromatographic-Mass Spectrometric Profile of Organic Acids in Urine and Serum of Diabetic Ketotic Patients, Journal of Chromatography, 1981, pp. 1-8, Elsevier Scientific Publishing Company, Amesterdam.
Lochner, April et al, Gas Chromatographic-Mass Spectrometric Analysis of Volatile Constituents in Saliva, Journal of Chromatography, 1986, pp. 267-282, Elsevier Scientific Publishing Company, Amesterdam.
Goodlett, David R. et al, Protein Identification with a Single Accurate Mass of a Cysteine-Containing Peptide and Constrained Database Searching, Analytical Chemistry, 2000, pp. 1112-1118, vol. 72, No. 6, American Chemical Society.
Griffin, Timothy J. et al, Quantitative Proteomic Analysis Using a MALDI Quadrupole Time-of-Flight Mass Spectrometer, Analytical Chemistry, 2001, pp. 978-986, vol. 73, No. 5, American Chemical Society.
Johnson, R. S. et al, Sequence Analysis of Peptide Mixtures by Automated Integratin of Edman and Mass Spectrometric Data, Proteing Science, 1991, 1, 1083-1091.
Chelius, Dirk, Quantitative Profiling of Proteins in Complex Mixtures Using Liquid Chromatography and Mass Spectrometry, Journal of Proteome Research, 202, 1, 317-323.
ASMS, American Society for Mass Spectrometry; Education, What is Mass Spectrometry, p. 1 of 1, last updated Dec. 1, 2001.
McLuckey, Scott A. et al, Mass Analysis at the Advent of the 21st Century, Chemical Reviews, 2001, pp. 571-606, vol. 101, No. 2, American Chemical Society.

* cited by examiner

| Protein | Protein Mw | Mixture A (μL) | Mixture B (μL) |
|---|---|---|---|
| Lactoperoxidase | 80642 | 20 | 40 |
| Lysozyme | 16238 | 20 | 20 |
| Alpha-lactalbumin | 16246 | 20 | 0 |
| Phosphorylase B | 97158 | 20 | 10 |
| Ribonuclease A | 16461 | 20 | 20 |
| Enolase | 46671 | 20 | 80 |
| Catalase | 57585 | 20 | 30 |
| Fetuin | 36353 | 20 | 20 |
| Cytochrome C | 11572 | 20 | 0 |
| Alcohol Dehydrogenase | 36692 | 20 | 80 |
| Beta-caseine | 25267 | 20 | 0 |
| Glucose oxidase | 65638 | 20 | 40 |
| Carbonic Anhydrase | 28508 | 20 | 100 |
| Serum Albumin | 66433 | 20 | 60 |

FIG. 4

| Avg MH+ | Avg Intensity | Avg Area | Avg RT | Avg CS |
|---|---|---|---|---|
| 1072.5099 | 216 | 6.4 | 6.31 | 2 |
| 1163.6300 | 221 | 6.9 | 48.11 | 2 |
| 1249.6222 | 5141 | 174.6 | 31.25 | 2 |
| 1283.7119 | 2813 | 95.7 | 58.27 | 2 |
| 1291.6039 | 6894 | 233.3 | 21.37 | 2 |
| 1305.7171 | 45349 | 1548.8 | 37.26 | 2 |
| 1319.6482 | 662 | 22.1 | 36.94 | 2 |
| 1324.6014 | 1714 | 58 | 27.52 | 2 |
| 1335.5916 | 1019 | 33.9 | 29.01 | 2 |
| 1399.6592 | 1905 | 62.5 | 26.58 | 2 |
| 1399.6964 | 38120 | 1298.3 | 58.93 | 2 |
| 1419.6976 | 29525 | 1007 | 45.67 | 2 |
| 1439.8124 | 15776 | 538.7 | 53.03 | 2 |
| 1443.6453 | 24108 | 821.9 | 2.58 | 2 |
| 1456.6412 | 2332 | 79.4 | 60.68 | 2 |
| 1463.5944 | 6301 | 214.7 | 12.50 | 2 |
| 1467.7430 | 3021 | 102.3 | 30.17 | 2 |
| 1478.5275 | 11457 | 389.9 | 25.47 | 2 |
| 1479.7991 | 29123 | 993.4 | 59.13 | 2 |
| 1491.7571 | 8698 | 297.5 | 38.45 | 2 |
| 1502.6189 | 17836 | 607 | 18.03 | 2 |
| 1511.8494 | 1532 | 51.9 | 30.68 | 2 |
| 1527.6758 | 1856 | 63 | 41.93 | 2 |
| 1532.7874 | 8311 | 281.2 | 22.32 | 2 |
| 1537.8062 | 792 | 26.4 | 35.51 | 2 |
| 1553.6662 | 741 | 23.6 | 25.30 | 2 |
| 1554.6599 | 19122 | 647.7 | 32.70 | 2 |
| 1567.7465 | 24188 | 823.7 | 81.11 | 2 |
| 1592.6639 | 6558 | 223.3 | 6.11 | 2 |

FIG. 6A

| Avg MH+ | Avg Intensity | Avg Area | Avg RT | Avg CS |
|---|---|---|---|---|
| 1608.6331 | 645 | 21.5 | 7.03 | 2 |
| 1623.6019 | 17549 | 599.5 | 34.88 | 2 |
| 1624.6034 | 6791 | 231.4 | 16.69 | 2 |
| 1624.6051 | 7805 | 264.9 | 45.24 | 2 |
| 1625.6144 | 485 | 14.2 | 43.22 | 2 |
| 1627.6233 | 786 | 25.6 | 8.92 | 2 |
| 1627.6308 | 671 | 21.8 | 42.27 | 2 |
| 1639.9458 | 23842 | 810.9 | 43.65 | 2 |
| 1748.6952 | 9942 | 339.6 | 26.88 | 2 |
| 1749.6830 | 16643 | 567 | 27.05 | 2 |
| 1753.7942 | 1390 | 46.7 | 28.17 | 2 |
| 1778.8297 | 4295 | 145.6 | 28.01 | 2 |
| 1838.7457 | 2822 | 95.4 | 6.75 | 2 |
| 1862.8981 | 941 | 31.6 | 31.06 | 3 |
| 1880.9229 | 25542 | 870.1 | 47.12 | 2.13 |
| 1888.9339 | 2533 | 85.6 | 77.76 | 2.03 |
| 1889.9011 | 1395 | 47.2 | 36.98 | 3 |
| 1901.8675 | 5962 | 201.8 | 37.89 | 2.67 |
| 1902.8566 | 1210 | 40.7 | 27.54 | 2.98 |
| 1907.9214 | 35302 | 1205.2 | 70.08 | 2.56 |
| 1910.7877 | 13815 | 470.6 | 27.65 | 2 |
| 1927.7967 | 9553 | 325.8 | 8.00 | 2.63 |
| 1955.9760 | 3518 | 119.4 | 37.71 | 2 |
| 2045.0278 | 13939 | 475.6 | 74.20 | 2.71 |
| 2046.0386 | 1178 | 39.3 | 40.20 | 2.46 |
| 2106.8021 | 1329 | 44.7 | 6.75 | 2 |
| 2159.0352 | 4738 | 160.2 | 36.92 | 2.8 |
| 2458.1805 | 39033 | 1333 | 36.93 | 2.81 |
| 2459.2065 | 534 | 17.5 | 37.15 | 2 |

FIG. 6B

| Avg MH+ | Avg Intensity | Avg Area | Avg RT | Avg CS |
|---|---|---|---|---|
| 2467.2532 | 829 | 27.7 | 48.09 | 2.36 |
| 2487.5035 | 986 | 33.3 | 56.12 | 3 |
| 2487.5581 | 2109 | 70.9 | 27.76 | 3 |
| 2487.5999 | 1326 | 44.1 | 35.82 | 3 |
| 2487.6116 | 2038 | 64.7 | 51.20 | 3 |
| 2487.7130 | 1674 | 56.4 | 15.63 | 3 |
| 2487.9076 | 16456 | 561.6 | 53.42 | 3 |
| 2487.9321 | 18565 | 633.7 | 32.90 | 3 |
| 2487.9973 | 5182 | 176.4 | 15.82 | 3 |
| 2488.2505 | 502 | 16.6 | 43.38 | 3 |
| 2492.2704 | 17187 | 585.6 | 89.93 | 2.76 |
| 1659.0013 | 1208 | 39.8 | 52.94 | 2 |
| 1659.0133 | 695 | 23.3 | 56.74 | 2 |
| 1659.0434 | 1055 | 35.3 | 14.95 | 2 |
| 1659.5446 | 3103 | 105.6 | 52.69 | 2 |
| 1659.5541 | 972 | 32.8 | 16.23 | 2 |
| 1680.5279 | 663 | 22.1 | 48.07 | 2 |
| 1724.8437 | 38060 | 1295.9 | 66.08 | 2 |
| 1730.6864 | 8632 | 292.8 | 28.15 | 2 |
| 1747.7125 | 2624 | 67.8 | 6.74 | 2 |

FIG. 6C

| Theor. MH+ | HPLC Index | Peptide pI | Calc. CS | His | XC R K | Length | Freq | Sequence | Protein MW | Protein pI |
|---|---|---|---|---|---|---|---|---|---|---|
| 1941.9227 | 21.6 | 4.35 | 2 | | 1; 0, 5 | 17 | 1 | ADLAKYICDNQDTISSK | 69275 | 6.1 |
| 922.4886 | 23 | 4.54 | 2 | | | 8 | 1 | AEFVEVTK | 69275 | 6.1 |
| 1692.9424 | 61.5 | 4.68 | 2 | | 1; 0, 8 | 15 | 1 | AEFVEVTKLVTDLTK | 69275 | 6.1 |
| 2498.1913 | 91.3 | 4.41 | 2.5 | | 1; 0, 5 | 21 | 1 | AFDEKLFTHADICTLPDTEK | 69275 | 6.1 |
| 1001.5896 | 56.9 | 11.2 | 2 | 1; 10: | 1; 0, 3 | 9 | 1 | ALKAWSVAR | 69275 | 6.1 |
| 2199.1007 | 59.7 | 4.41 | 2 | | 1; 0, 7 | 19 | 1 | ATEEQLKTVMENFVAFVDK | 69275 | 6.1 |
| 1145.6431 | 45.2 | 11.2 | 2 | | 1; 6, 0 | 10 | 1 | AWSVARLSQK | 69275 | 6.1 |
| 1195.5893 | 10.5 | 8.63 | 2 | | 1; 0, 6 | 10 | 1 | CASIQKFGER | 69275 | 6.1 |
| 1927.7987 | 7.4 | 4.29 | 2 | | 1; 0, 7 | 17 | 1 | CCAADDKEACFAVEGPK | 69275 | 6.1 |
| 1138.4984 | -8 | 6.34 | 2 | | | 9 | 1 | CCTESLVNR | 69275 | 6.1 |
| 3000.4016 | 34.2 | 6.48 | 3.2 | | 2; 9, 0 | 25 | 1 | CCTESLVNRRPCFSALTPDETYVPK | 69275 | 6.1 |
| 1166.4933 | -31.5 | 6.48 | 2 | | 1; 0, 4 | 9 | 1 | CCTKPESER | 69275 | 6.1 |
| 2872.3100 | 19.9 | 4.89 | 2.5 | | 2; 0, 4 | 23 | 1 | CCTKPESERMPCTEDYLSLILNR | 69275 | 6.1 |
| 1567.7433 | 81.1 | 4.32 | 2 | | | 13 | 1 | DAFLGSFLYEYSR | 69275 | 6.1 |
| 1723.8444 | 77.5 | 6.46 | 2 | | 1; 13, 0 | 14 | 1 | DAFLGSFLYEYSRR | 69275 | 6.1 |
| 1554.6534 | 20.6 | 4.34 | 2.15 | 1; 4: | | 13 | 1 | DDPHACYSTVFDK | 69275 | 6.1 |
| 1795.8325 | 38.9 | 5.46 | 2.15 | 1; 4: | 1; 0, 13 | 15 | 1 | DDPHACYSTVFDKLK | 69275 | 6.1 |
| 2444.1855 | 55.3 | 4.11 | 2 | | 2; 0, 8 | 21 | 1 | DDSPDLPKLKPDPNTLCDEFK | 69275 | 6.1 |
| 974.4583 | 21.7 | 4.67 | 2 | 1; 6: | | 8 | 1 | DLGEEHFK | 69275 | 6.1 |
| 3447.7047 | 120.8 | 4.92 | 3.2 | 2; 6: | 1; 0, 8 | 29 | 1 | DLGEEHFKGLVLIAFSQYLQQCPFDEHVK | 69275 | 6.1 |
| 1193.6027 | -4.3 | 7.52 | 2.25 | 2; 3: | 1; 0, 4 | 10 | 1 | DTHKSEIAHR | 69275 | 6.1 |
| 1254.5788 | -9.3 | 6.42 | 2 | | 1; 0, 4 | 10 | 1 | DVCKNYQEAK | 69275 | 6.1 |
| 1107.5144 | 20.7 | 4.54 | 2 | | | 10 | 1 | EACFAVEGPK | 69275 | 6.1 |
| 2091.0796 | 79.5 | 4.54 | 2 | | 1; 0, 10 | 20 | 1 | EACFAVEGPKLVVSTQTALA | 69275 | 6.1 |
| 1291.6025 | 8.8 | 4.68 | 2 | | 1; 0, 5 | 10 | 1 | ECCDKPLLEK | 69275 | 6.1 |
| 2345.0938 | -7.1 | 5.01 | 2.15 | 1; 12: | 2; 0, 5 | 19 | 1 | ECCDKPLLEKSHCIAEVEK | 69275 | 6.1 |
| 1749.6629 | -3.5 | 4.05 | 2.15 | 1; 4: | | 14 | 1 | ECCHGDLLECADDR | 69275 | 6.1 |
| 2247.9431 | 24.5 | 4.19 | 2.65 | 1; 4: | 1; 14, 0 | 19 | 1 | ECCHGDLLECADDRADLAK | 69275 | 6.1 |
| 1478.5237 | -17.1 | 3.84 | 2 | | | 12 | 1 | ETYGDMADCCEK | 69275 | 6.1 |
| 2117.8213 | -30.1 | 4.06 | 2.15 | | 1; 0, 12 | 17 | 1 | ETYGDMADCCEKQEPER | 69275 | 6.1 |

FIG. 7A

| Theor. MH+ | HPLC Index | Peptide pI | Calc. CS | His | X C R K | Length | Freq | Sequence | Protein MW | Protein pI |
|---|---|---|---|---|---|---|---|---|---|---|
| 1502.6142 | -2.6 | 4.09 | 2 | | | 12 | 1 | EYEATLEECCAK | 69275 | 6.1 |
| 3038.2493 | 11.4 | 4.18 | 3.2 | 1;16: | 1;0,12 | 25 | 1 | EYEATLEECCAKDDPHACYSTVFDK | 69275 | 6.1 |
| 1249.6217 | 37.2 | 5.66 | 2.15 | 1;8: | 1;0,2 | 10 | 1 | FKDLGEEHFK | 69275 | 6.1 |
| 1294.7047 | 43.6 | 6.55 | 2 | | 1;0,3 | 11 | 1 | FPKAEFVEVTK | 69275 | 6.1 |
| 1445.7581 | 72.2 | 8.93 | 2 | | 1;0,4 | 11 | 1 | FWGKYLYEIAR | 69275 | 6.1 |
| 1388.7394 | 47.2 | 8.63 | 2 | | 1;0,7 | 12 | 1 | GACLLPKIETMR | 69275 | 6.1 |
| 2492.2647 | 105.7 | 5.53 | 2.5 | 1;19: | | 21 | 1 | GLVIJAFSQYLQQCPFDEHVK | 69275 | 6.1 |
| 1308.7276 | 12.1 | 9.09 | 2 | 1;1: | 2;0,2 | 11 | 1 | HKPKATEEQLK | 69275 | 6.1 |
| 1305.7167 | 40 | 5.53 | 2 | 1;1: | | 11 | 1 | HLVDEPQNLIK | 69275 | 6.1 |
| 2355.1403 | 30 | 4.77 | 2.15 | 1;1: | 1;0,11 | 19 | 1 | HLVDEPQNLIKQNCDQFEK | 69275 | 6.1 |
| 1283.7112 | 55 | 7.35 | 2 | 1;1: | | 11 | 1 | HPEYAVSVLLR | 69275 | 6.1 |
| 1595.9273 | 78.6 | 9.06 | 2.65 | 1;1: | 1;11,0 | 14 | 1 | HPEYAVSVLRLAK | 69275 | 6.1 |
| 1888.9274 | 95.6 | 7.33 | 2.15 | 1;1: | | 15 | 1 | HPYFYAPELLYYANK | 69275 | 6.1 |
| 906.4719 | -1.9 | 6.56 | 2 | | 1;5,0 | 7 | 1 | IETMREK | 69275 | 6.1 |
| 1142.7149 | 63.4 | 8.19 | 2 | | 1;0,1 | 10 | 1 | KQTALVELLK | 69275 | 6.1 |
| 1639.9383 | 29.5 | 9.34 | 2 | | 1;0,3 | 15 | 1 | KVPQVSTPTLVEVSR | 69275 | 6.1 |
| 1814.8304 | 21 | 4.52 | 2.15 | | 1;0,7 | 15 | 1 | LAKEYEATLEECCAK | 69275 | 6.1 |
| 1539.8204 | 22.5 | 7.31 | 2.15 | 1;5: | | 13 | 2 | LCVLHEKTPVSEK | 69275 | 6.1 |
| 1907.9213 | 78.5 | 4.51 | 2.5 | 1;5: | | 16 | 1 | LFTFHADICTLPDTEK | 69275 | 6.1 |
| 2277.1589 | 81.1 | 5.58 | 2.15 | 1;5: | 1;0,16 | 19 | 1 | LFTFHADICTLPDTEKQIK | 69275 | 6.1 |
| 1479.7960 | 70 | 6.41 | 2 | | | 13 | 1 | LGEYGFQNALIVR | 69275 | 6.1 |
| 1900.0081 | 73.1 | 8.98 | 2 | | 1;13,0 | 16 | 1 | LGEYGFQNALIVRYTR | 69275 | 6.1 |
| 1532.7816 | 25.1 | 6.51 | 2.5 | | 2;0,2 | 12 | 1 | LKECCDKPLLEK | 69275 | 6.1 |
| 1546.8957 | 56.3 | 7.35 | 2.15 | 1;3: | 1;0,2 | 13 | 1 | LKHLVDEPQNLIK | 69275 | 6.1 |
| 1576.7681 | 41.6 | 4.52 | 2 | | 1;0,2 | 13 | 1 | LKPDPNTLCDEFK | 69275 | 6.1 |
| 2019.9697 | 35.2 | 4.41 | 3 | | 2;0,2 | 17 | 1 | LKPDPNTLCDEFKADEK | 69275 | 6.1 |
| 975.5409 | 19.6 | 9.75 | 2 | | 1;2,0 | 8 | 1 | LRCASIQK | 69275 | 6.1 |
| 1163.6312 | 53.8 | 4.54 | 2 | | | 10 | 1 | LVNELTEFAK | 69275 | 6.1 |
| 2608.2022 | 26.1 | 4.6 | 2.5 | 1;18: | 1;0,10 | 23 | 1 | LVNELTEFAKTCVADESHAGCEK | 69275 | 6.1 |
| 1153.6945 | 42.8 | 9.19 | 2 | 1;9: | 1;0,7 | 10 | 1 | LVTDLTKVHK | 69275 | 6.1 |

FIG. 7B

| Theor. MH+ | HPLC Index | Peptide Pi | Calc. CS | His | XC R K | Length | Freq | Sequence | Protein MW | Protein pI |
|---|---|---|---|---|---|---|---|---|---|---|
| 1002.5835 | 65.4 | 5.75 | 2 | | | 10 | 1 | LVVSTQTALA | 69275 | 6.1 |
| 2262.2361 | 147.3 | 10.2 | 2.15 | | 1; 0, 2 | 19 | 1 | MKWVTFISLLLLFSSAYSR | 69275 | 6.1 |
| 1724.8351 | 58 | 4.32 | 2 | | | 14 | 1 | MPCTEDYLSILNR | 69275 | 6.1 |
| 2604.2987 | 79.4 | 5.66 | 3 | 1;19: | 1; 14, 0 | 21 | 1 | MPCTEDYLSILNRLCVLHEK | 69275 | 6.1 |
| 1034.4729 | 13.9 | 7.3 | 2 | 1;7: | | 8 | 1 | NECFLSHK | 69275 | 6.1 |
| 1901.8703 | 27.6 | 4.64 | 2.5 | 1;7: | 1; 0, 8 | 16 | 1 | NECFLSHKDDSPDLPK | 69275 | 6.1 |
| 2301.0828 | 77.5 | 4.88 | 2.15 | | 1; 0, 6 | 19 | 1 | NYQEAKDAFLGSFLYEYSR | 69275 | 6.1 |
| 1673.7705 | 0.9 | 5.72 | 2.65 | 1; 12: | 1; 5, 0 | 13 | 1 | QEPERNECFLSHK | 69275 | 6.1 |
| 1068.4420 | -3.4 | 4.32 | 2 | | | 8 | 1 | QNCDQFEK | 69275 | 6.1 |
| 2529.2196 | 60 | 4.68 | 2.5 | | 1; 0, 8 | 21 | 1 | QNCDQFEKLGEYGFQNALIVR | 69275 | 6.1 |
| 1014.6199 | 67.1 | 6.41 | 2 | | | 9 | 1 | QTALVELLK | 69275 | 6.1 |
| 1504.9215 | 62.7 | 10.11 | 2.15 | 1;10: | 2; 0, 9 | 13 | 1 | QTALVELLKHKPK | 69275 | 6.1 |
| 1439.8123 | 51.4 | 9.15 | 2.5 | 1; 2: | 1; 1, 0 | 12 | 1 | RHPEYAVSVLLR | 69275 | 6.1 |
| 2045.0285 | 92 | 8.78 | 2.65 | 1; 2: | 1; 1, 0 | 16 | 1 | RHPYFYAPELLYYANK | 69275 | 6.1 |
| 1880.9216 | 48.8 | 6.42 | 2.15 | | 1; 1, 0 | 16 | 1 | RPCFSALTPDETYVPK | 69275 | 6.1 |
| 2471.1916 | 61.6 | 4.78 | 2.5 | | 2; 1, 16 | 21 | 1 | RPCFSALTPDETYVPKAFDEK | 69275 | 6.1 |
| 987.5376 | 19.1 | 9.35 | 2.25 | 1; 5: | 1; 6, 0 | 8 | 1 | SEIAHRFK | 69275 | 6.1 |
| 1072.5097 | -9.3 | 5.62 | 2 | 1; 2: | | 9 | 1 | SHCIAEVEK | 69275 | 6.1 |
| 1419.6942 | 56.3 | 5.53 | 2 | 1; 3: | | 12 | 1 | SLHTLFGDELCK | 69275 | 6.1 |
| 1946.0169 | 79.4 | 7.31 | 2.65 | 1; 3: | 1; 0, 12 | 17 | 1 | SLHTLFGDELCKVASLR | 69275 | 6.1 |
| 1463.5894 | -21.1 | 4.67 | 2.15 | 1; 8: | | 13 | 1 | TCVADESHAGCEK | 69275 | 6.1 |
| 2864.2652 | 28.6 | 4.92 | 3.2 | 2; 8: | 1; 0, 13 | 25 | 1 | TCVADESHAGCEKSLHTLFGDELCK | 69275 | 6.1 |
| 988.5679 | 1.7 | 9.19 | 2 | | 1; 0, 6 | 9 | 1 | TPVSEKVTK | 69275 | 6.1 |
| 1399.6932 | 49.8 | 4.32 | 2 | | | 12 | 1 | TVMENFVAFVDK | 69275 | 6.1 |
| 2219.9774 | 36.5 | 4.17 | 2 | | 1; 0, 12 | 19 | 1 | TVMENFVAFVDKCCAADDK | 69275 | 6.1 |
| 2004.8464 | 6 | 4.29 | 2.15 | | 1; 5, 0 | 17 | 1 | VASLRETYGDMADCCEK | 69275 | 6.1 |
| 1579.7320 | -32 | 8.42 | 2.15 | | 2; 4, 8 | 13 | 1 | VGTRCCTKPESER | 69275 | 6.1 |
| 2113.8852 | -5.8 | 4.83 | 2.65 | 2; 2: | 1; 0, 3 | 17 | 1 | VHKECCHGDLLECADDR | 69275 | 6.1 |
| 1511.8433 | 33.2 | 6.41 | 2 | | | 14 | 1 | VPQVSTPTLVEVSR | 69275 | 6.1 |

FIG. 7C

| Theor. MH+ | HPLC Index | Peptide pI | Calc. CS | His | XC R K | Length | Freq | Sequence | Protein MW | Protein pI |
|---|---|---|---|---|---|---|---|---|---|---|
| 1897.0759 | 44.2 | 9.34 | 2.15 | | 1;14, 0 | 18 | 1 | VPQVSTPTLVEVSRSLGK | 69275 | 6.1 |
| 1466.7095 | -7.4 | 8.42 | 2 | | 1; 0, 3 | 12 | 1 | VTKCCTESLVNR | 69275 | 6.1 |
| 2003.1006 | 145.4 | 9.15 | 2 | | | 17 | 1 | WVTFISLLLLFSSAYSR | 69275 | 6.1 |
| 2462.3600 | 163.3 | 10.84 | 2 | | 1;17, 0 | 21 | 1 | WVTFISLLLLFSSAYSRGVFR | 69275 | 6.1 |
| 1443.6425 | -6.4 | 4.1 | 2 | | | 12 | 1 | YICDNQDTISSK | 69275 | 6.1 |
| 1684.8216 | 9.9 | 6.27 | 2 | | 1; 0, 12 | 14 | 1 | YICDNQDTISSKLK | 69275 | 6.1 |
| 927.4940 | 41.6 | 6.4 | 2 | | | 7 | 1 | YLYEIAR | 69275 | 6.1 |
| 1083.5951 | 38 | 8.98 | 2 | | 1; 7, 0 | 8 | 1 | YLYEIARR | 69275 | 6.1 |
| 1747.7055 | -4.2 | 4.09 | 2 | | | 14 | 1 | YNGVFQECCQAEDK | 69275 | 6.1 |
| 2487.1105 | 34.1 | 4.68 | 2 | | 1; 0, 14 | 21 | 1 | YNGVFQECCQAEDKGACLLPK | 69275 | 6.1 |

FIG. 7D

SERUM ALBUMIN　　　　　　　　　　　　　　　　　Protein Coverage: 64%

| Obs. MH+ | Calc. MH+ | Mass Error ppm | RT | Obs. HPLC Index | Theor. HPLC Index | HPLC Index Diff. | Obs. CS | Theor. CS | CS Diff. | Sequence |
|---|---|---|---|---|---|---|---|---|---|---|
| 1072.5099 | 1072.5097 | -0.1865 | 6.31 | -4.8 | -9.3 | 4.5 | 2.00 | 2.00 | 0.0 | SHCIAEVEK |
| 1163.6300 | 1163.6312 | 1.0313 | 48.11 | 47.3 | 53.8 | 6.5 | 2.00 | 2.00 | 0.0 | LVNELTEFAK |
| 1249.6222 | 1249.6217 | -0.4001 | 31.25 | 26.3 | 37.2 | 10.9 | 2.00 | 2.15 | 0.2 | FKDLGEEHFK |
| 1283.7119 | 1283.7112 | -0.5453 | 58.27 | 59.9 | 55 | 4.9 | 2.00 | 2.00 | 0.0 | HPEYAVSVLLR |
| 1291.6039 | 1291.6025 | -1.0839 | 21.37 | 14.0 | 8.8 | 5.2 | 2.00 | 2.00 | 0.0 | ECCDKPLLEK |
| 1305.7171 | 1305.7167 | -0.3063 | 37.26 | 33.8 | 40 | 6.2 | 2.00 | 2.00 | 0.0 | HLVDEPQNLIK |
| 1399.6964 | 1399.6932 | -2.2862 | 58.93 | 60.7 | 49.8 | 10.9 | 2.00 | 2.00 | 0.0 | TVMENFVAFVDK |
| 1419.6976 | 1419.6942 | -2.3949 | 45.67 | 44.2 | 56.3 | 12.1 | 2.00 | 2.00 | 0.0 | SLHTLFGDELCK |
| 1439.8124 | 1439.8123 | -0.0695 | 53.03 | 53.4 | 51.4 | 2.0 | 2.00 | 2.50 | 0.5 | RHPEYAVSVLLR |
| 1443.6453 | 1443.6425 | -1.9395 | 2.58 | -9.4 | -6.4 | 3.0 | 2.00 | 2.00 | 0.0 | YICDNQDTISSK |
| 1463.5944 | 1463.5894 | -3.4163 | 12.50 | 3.0 | -21.1 | 24.1 | 2.00 | 2.15 | 0.2 | TCVADESHAGCEK |
| 1478.5275 | 1478.5237 | -2.5701 | 25.47 | 19.1 | 1.3 | 17.8 | 2.00 | 2.00 | 0.0 | ETYGDMADCCEK |
| 1479.7991 | 1479.7960 | -2.0949 | 59.13 | 61.0 | 70 | 9.0 | 2.00 | 2.00 | 0.0 | LGEYGFQNALIVR |
| 1502.6189 | 1502.6142 | -3.1279 | 18.03 | 9.8 | -2.6 | 12.4 | 2.00 | 2.00 | 0.0 | EYEATLEECCAK |
| 1511.8494 | 1511.8433 | -4.0348 | 30.68 | 25.6 | 33.2 | 7.6 | 2.00 | 2.00 | 0.0 | VPQVSTPTLVEVSR |
| 1532.7874 | 1532.7816 | -3.7840 | 22.32 | 15.2 | 25.1 | 9.9 | 2.00 | 2.50 | 0.5 | LKECCDKPLLEK |
| 1554.6599 | 1554.6534 | -4.1810 | 32.70 | 28.1 | 20.6 | 7.5 | 2.00 | 2.15 | 0.2 | DDPHACYSTVFDK |

FIG. 8A

SERUM ALBUMIN  Protein Coverage: 64%

| Obs. MH+ | Calc. MH+ | Mass Error ppm | RT | Obs. HPLC Index | Theor. HPLC Index | HPLC Index Diff. | Obs. CS | Theor. CS | CS Diff. | Sequence |
|---|---|---|---|---|---|---|---|---|---|---|
| 1567.7465 | 1567.7433 | -2.0412 | 81.11 | 88.4 | 81.1 | 7.3 | 2.00 | 2.00 | 0.0 | DAFLGSFLYEYSR |
| 1639.9458 | 1639.9383 | -4.5733 | 43.65 | 41.7 | 29.5 | 12.2 | 2.00 | 2.15 | 0.2 | KVPQVSTPTLVEVSR |
| 1724.8437 | 1724.8351 | -4.9860 | 66.08 | 69.6 | 58 | 11.6 | 2.00 | 2.00 | 0.0 | MPCTEDYLSLILNR |
| 1747.7125 | 1747.7055 | -4.0053 | 6.74 | -4.2 | -4.2 | 0.0 | 2.00 | 2.00 | 0.0 | YNGVFQECCQAEDK |
| 1880.9229 | 1880.9216 | -0.6912 | 47.12 | 46.1 | 48.8 | 2.7 | 2.13 | 2.15 | 0.0 | RPCFSALTPDETYVPK |
| 1888.9339 | 1888.9274 | -3.4411 | 77.76 | 84.2 | 95.6 | 11.4 | 2.03 | 2.15 | 0.1 | HPYFYAPELLYYANK |
| 1901.8675 | 1901.8703 | 1.4722 | 37.89 | 34.6 | 27.6 | 7.0 | 2.67 | 2.50 | 0.2 | NECFLSHKDDSPDLPK |
| 1907.9214 | 1907.9213 | -0.0524 | 70.08 | 74.6 | 78.5 | 3.9 | 2.56 | 2.50 | 0.1 | LFTFHADICTLPDTEK |
| 1927.7967 | 1927.7987 | 1.0375 | 8.00 | -2.7 | 7.4 | 10.1 | 2.63 | 2.00 | 0.6 | CCAADDKEACFAVEGPK |
| 2045.0278 | 2045.0285 | 0.3423 | 74.20 | 79.8 | 92 | 12.2 | 2.71 | 2.65 | 0.1 | RHPYFYAPELLYYANK |
| 2492.2704 | 2492.2647 | -2.2871 | 89.93 | 99.3 | 105.7 | 6.4 | 2.76 | 2.50 | 0.3 | GLVLIAFSQYLQQCPFDEHVK |

FIG. 8B

| | Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|---|
| ALCOHOL DEHYRDOGENASE I | | | | | | | | | | | Sequence Coverage 26% |
| 1 | 1013.5976 | 1013.5998 | 2.2 | 42.9 | 40.7 | 41.8 | 1.1 | 2.00 | 2.00 | 0.0 | ANELLINVK |
| 2 | 1071.6453 | 1071.6418 | -3.3 | 40.6 | 37.9 | 28.9 | 9.0 | 2.00 | 2.00 | 0.0 | EKDIVGAVLK |
| 3 | 1136.5729 | 1136.5738 | 0.8 | 33.3 | 28.8 | 22.4 | 6.4 | 2.00 | 2.00 | 0.0 | GVIFYESHGK |
| 4 | 1312.6808 | 1312.6788 | -1.5 | 64.4 | 67.6 | 42.3 | 25.3 | 2.00 | 2.00 | 0.0 | SIGGEVFIDFTK |
| 5 | 1447.8038 | 1447.8048 | 0.7 | 60.1 | 62.2 | 48.8 | 13.4 | 2.00 | 2.00 | 0.0 | VVGLSTLPEIYEK |
| 6 | 1618.8428 | 1618.8438 | 0.6 | 52.3 | 52.5 | 39.6 | 12.9 | 2.36 | 2.15 | 0.2 | VLGIDGGEGKEELFR |
| 7 | 2019.0656 | 2019.0698 | 2.1 | 59.3 | 61.2 | 49.2 | 12.0 | 2.88 | 2.50 | 0.4 | LPLVGGHEGAGVVVGMGENVK |
| ALCOHOL DEHYDROGENASE II | | | | | | | | | | | Sequence Coverage 16% |
| 1 | 1291.6136 | 1291.6108 | -2.2 | 21.8 | 14.5 | 4.5 | 10.0 | 2.00 | 2.00 | 0.0 | CSSDVFNHVVK |
| 2 | 2019.0656 | 2019.0698 | 2.1 | 59.3 | 61.2 | 49.2 | 12.0 | 2.88 | 2.50 | 0.4 | LPLVGGHEGAGVVVGMG |
| 3 | 2477.1375 | 2477.1458 | 3.4 | 59.6 | 61.6 | 76.2 | 14.6 | 3.31 | 3.50 | 0.2 | YSGVCHTDLHAWHGDWP |
| ALCOHOL DEHYDROGENASE III | | | | | | | | | | | Sequence Coverage 3% |
| 1 | 1154.6233 | 1154.6208 | -2.2 | 21.9 | 14.7 | 19.2 | 4.5 | 2.00 | 2.00 | 0.0 | GVIFYENKGK |

FIG. 9A

| | Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|---|
| FETUIN | | | | | | | | | Sequence Coverage | | 31% |
| 1 | 1154.6133 | 1154.6168 | 3.0 | 21.9 | 14.7 | 18.7 | 4.0 | 2.00 | 2.00 | 0.0 | HTLNQIDSVK |
| 2 | 1269.6487 | 1269.6478 | -0.7 | 56.1 | 57.2 | 56.8 | 0.4 | 2.00 | 2.00 | 0.0 | QDGQFSVLFTK |
| 3 | 1474.8407 | 1474.8378 | -2.0 | 42.2 | 39.9 | 36.4 | 3.5 | 2.00 | 2.00 | 0.0 | TPIVGQPSIPGGPVR |
| 4 | 1502.8035 | 1502.7968 | -4.4 | 67.3 | 64.8 | 19.7 | 45.1 | 2.12 | 2.30 | 0.2 | GYKHTLNQIDSVK |
| 5 | 1740.8381 | 1740.8408 | 1.6 | 60.2 | 62.4 | 71.6 | 9.2 | 2.09 | 2.00 | 0.1 | LCPDCPLLAPLNDSR |
| 6 | 1977.9428 | 1977.9448 | 1.0 | 33.5 | 29.1 | 16.2 | 12.9 | 2.96 | 2.75 | 0.2 | QQTQHAVEGDCDIHVLK |
| 7 | 2120.0091 | 2120.0048 | -2.0 | 44.5 | 42.8 | 24.7 | 18.1 | 3.00 | 2.50 | 0.5 | HTFSGVASVESSSGEAFH |
| 8 | 2406.0795 | 2406.0768 | -1.1 | 59.8 | 61.8 | 45.4 | 16.4 | 2.20 | 2.50 | 0.3 | EPACDDPDTEQAALAAVD |
| 9 | 2519.3261 | 2519.3218 | -1.7 | 109 | 123.7 | 105.2 | 18.5 | 2.33 | 2.50 | 0.2 | AQFVPLPVSVSVEFAVAAT DCIAK |
| ALPHA-LACTALBUMIN | | | | | | | | | Sequence Coverage | | 54% |
| 1 | 1091.5162 | 1091.5198 | 3.3 | 38.1 | 34.8 | 39.7 | 4.9 | 2.00 | 2.00 | 0.0 | LDQWLCEK |
| 2 | 1200.6519 | 1200.6528 | 0.7 | 52.8 | 53.1 | 53.5 | 0.4 | 2.00 | 2.00 | 0.0 | VGINYWLAHK |
| 3 | 1699.7598 | 1699.7558 | -2.4 | 63.8 | 66.8 | 54.9 | 11.9 | 3.55 | 2.00 | 0.0 | FLDDDLTDDIMCVK |
| 4 | 4711.1932 | 4711.1788 | -3.1 | 85.8 | 94.2 | 82.1 | 12.1 | 3.50 | 3.50 | 0.0 | GYGGVSLPEWVCTTFHTS GYDTQAIVQNNDSTEYGL FQINNK |

FIG. 9B

| | Obs. MH+ | Actual MH+ | Mass Error ppm | RT | Obs. HPLC Index | Theor HPLC Index | HPLCI Diff | Obs. CS | Theor CS | CS Diff. | Sequence |
|---|---|---|---|---|---|---|---|---|---|---|---|
| BETA CASEIN | | | | | | | | | | Sequence Coverage | 15% |
| 1 | 1591.9470 | 1591.9428 | -2.6 | 80.8 | 87.9 | 62.8 | 25.1 | 2.24 | 2.15 | 0.1 | VLPVPQKAVPYPQR |
| 2 | 2186.1795 | 2186.1688 | -4.9 | 89.2 | 98.5 | 118.1 | 19.6 | 2.07 | 2.00 | 0.1 | DMPIQAFLLYQEPVLGPVR |
| CARBONIC ANHYDRASE II | | | | | | | | | | Sequence Coverage | 31% |
| 1 | 973.5648 | 973.5668 | 2.1 | 42.2 | 39.9 | 50.4 | 10.5 | 2.00 | 2.00 | 0.0 | VLDALDSIK |
| 2 | 1581.8040 | 1581.8078 | 2.4 | 52.6 | 52.9 | 67.0 | 14.1 | 3.00 | 2.15 | 0.9 | YAAELHLVHWNTK |
| 3 | 1709.9058 | 1709.9128 | 4.1 | 50.8 | 50.6 | 63.3 | 12.7 | 2.89 | 2.50 | 0.4 | KYAAELHLVHWNTK |
| 4 | 2198.2252 | 2198.2188 | -2.9 | 75.3 | 81.2 | 100.3 | 19.1 | 2.93 | 2.50 | 0.4 | AVVQDPALKPLALVYGEA |
| 5 | 2253.1664 | 2253.1558 | -4.7 | 82.9 | 90.6 | 114.3 | 23.7 | 2.12 | 2.50 | 0.4 | YGDFGTAAQQPDGLAVV GVFLK |
| CYTOCHROME C | | | | | | | | | | Sequence Coverage | 36% |
| 1 | 1168.6202 | 1168.6228 | 2.2 | 50.4 | 50.2 | 56.7 | 6.5 | 2.00 | 2.00 | 0.0 | TGPNLHGLFGR |
| 2 | 1456.6732 | 1456.6708 | -1.6 | 23.4 | 16.6 | 33.9 | 17.3 | 2.00 | 2.00 | 0.0 | TGQAPGFSYTDANK |
| 3 | 1584.7697 | 1584.7658 | -2.5 | 22.4 | 15.3 | 30.2 | 14.9 | 2.00 | 2.00 | 0.0 | KTGQAPGFSYTDANK |

FIG. 9C

| | Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|---|
| | CATALASE | | | | | | | | | | 53% |
| 1 | 1046.4978 | 1046.5018 | 3.8 | 2.6 | -9.4 | 15.9 | 25.3 | 2.00 | 2.00 | 0.0 | THFSGDVQR |
| 2 | 1154.6038 | 1154.5988 | -4.3 | 32.1 | 27.3 | 31.5 | 4.2 | 2.00 | 2.00 | 0.0 | LCENIAGHLK |
| 3 | 1285.6169 | 1285.6178 | 0.7 | 22.7 | 15.7 | 45.1 | 29.4 | 2.00 | 2.00 | 0.0 | LAHEDPDYGLR |
| 4 | 1338.6464 | 1338.6468 | 0.3 | 21.9 | 14.7 | 24.3 | 9.6 | 2.00 | 2.00 | 0.0 | LVNADGEAVYCK |
| 5 | 1407.6310 | 1407.6288 | -1.6 | 22.9 | 15.9 | 9.5 | 6.4 | 2.00 | 2.00 | 0.0 | NFSDVHPEYGSR |
| 6 | 1479.6797 | 1479.6828 | 2.1 | 21.8 | 14.5 | 10.0 | 4.5 | 2.00 | 2.00 | 0.0 | FNSANDDNVTQVR |
| 7 | 1483.7019 | 1483.7028 | 0.6 | 22.1 | 14.9 | 20.7 | 5.8 | 2.00 | 2.00 | 0.0 | FSTVAGESGSADTVR |
| 8 | 1502.8035 | 1502.8008 | -1.8 | 67.3 | 71.2 | 86.8 | 15.6 | 2.00 | 2.00 | 0.0 | DALLFPSFIHSQK |
| 9 | 1577.8359 | 1577.8378 | 1.2 | 60.3 | 62.4 | 66.6 | 4.2 | 2.00 | 2.15 | 0.2 | VWPHGDYPLIPVGK |
| 10 | 1688.9165 | 1688.9218 | 3.1 | 39.1 | 36.0 | 37.3 | 1.3 | 3.00 | 2.75 | 0.3 | IQALLDKYNEEKPK |
| 11 | 1740.8381 | 1740.8348 | -1.9 | 60.2 | 62.4 | 57.9 | 4.5 | 2.78 | 2.00 | 0.8 | GAGAFGYFEVTHDITR |
| 12 | 1803.9270 | 1803.9218 | -2.9 | 60.1 | 62.2 | 58.1 | 4.1 | 2.09 | 2.15 | 0.1 | LGPNYLQIPVNCPYR |
| 13 | 1851.8871 | 1851.8838 | -1.8 | 22.6 | 15.5 | 19.3 | 3.8 | 2.00 | 2.00 | 0.0 | FSTVAGESGSADTVRDPR |
| 14 | 2189.0672 | 2189.0698 | 1.2 | 81.0 | 88.3 | 91.3 | 3.0 | 2.34 | 2.15 | 0.2 | GPLLVQDVVFTDEMAHFD |
| 15 | 2518.2212 | 2518.2238 | 1.0 | 85.6 | 93.9 | 93.8 | 0.1 | 2.90 | 2.75 | 0.2 | FYTEDGNWDLVGNNTPIF FIR |
| 16 | 3202.5331 | 3202.5338 | 0.2 | 90.2 | 99.7 | 77.7 | 22.0 | 2.27 | 2.00 | 0.2 | NPVNYFAEVEQLAFDPSN MPPGIEPSPDK |
| 17 | 3209.5273 | 3209.5158 | -3.6 | 103 | 116.2 | 134.9 | 18.7 | 2.96 | 3.20 | 0.2 | DPDMVWDFWSLRPESLH QVSFLFSDR |

Sequence Coverage

FIG. 9D

| | Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|---|
| | ENOLASE 1 | | | | | | | | | Sequence Coverage | 56% |
| 1 | 1100.5217 | 1100.5268 | 4.6 | 36.2 | 32.4 | 34.4 | 2.0 | 2.00 | 2.00 | 0.0 | DGKYDLDFK |
| 2 | 1159.6101 | 1159.6108 | 0.6 | 22.9 | 15.9 | 18.7 | 2.8 | 2.00 | 2.00 | 0.0 | IGSEVYHNLK |
| 3 | 1286.7108 | 1286.7108 | 0.0 | 52.5 | 52.7 | 44.6 | 8.1 | 2.00 | 2.00 | 0.0 | NVNDVIAPAFVK |
| 4 | 1288.7073 | 1288.7108 | 2.7 | 40.4 | 37.7 | 17.9 | 19.8 | 2.00 | 2.00 | 0.0 | VNQIGTLSESIK |
| 5 | 1373.6400 | 1373.6408 | 0.6 | 58.4 | 60.1 | 46.6 | 13.5 | 2.00 | 2.00 | 0.0 | IGLDCASSEFFK |
| 6 | 1412.8248 | 1412.8228 | -1.4 | 61.2 | 63.6 | 86.0 | 22.4 | 2.00 | 2.00 | 0.0 | LGANAILGVSLAASR |
| 7 | 1416.7245 | 1416.7218 | -1.9 | 39.4 | 36.4 | 9.2 | 27.2 | 2.00 | 2.00 | 0.0 | GNPTVEVELTTEK |
| 8 | 1578.8048 | 1578.8018 | -1.9 | 64.4 | 67.5 | 67.9 | 0.4 | 2.00 | 2.00 | 0.0 | AVDDFLISLDGTANK |
| 9 | 1755.9415 | 1755.9488 | 4.2 | 59.9 | 61.9 | 52.2 | 9.7 | 2.00 | 2.00 | 0.0 | TAGIQIVADDLTVTNPK |
| 10 | 1789.8470 | 1789.8448 | -1.2 | 60.0 | 62.1 | 64.4 | 2.3 | 2.30 | 2.15 | 0.2 | AAQDSFAAGWGVMVSHR |
| 11 | 1840.9287 | 1840.9228 | -3.2 | 52.2 | 52.4 | 31.7 | 20.7 | 2.28 | 2.15 | 0.1 | SIVPSGASTGVHEALEMR |
| 12 | 1872.9659 | 1872.9678 | 1.0 | 83.7 | 91.6 | 113.3 | 21.7 | 2.70 | 2.50 | 0.2 | WLTGPQLADLYHSLMK |
| 13 | 2441.1447 | 2441.1368 | -3.2 | 57.5 | 58.9 | 52.6 | 6.3 | 2.98 | 3.00 | 0.0 | IEEELGDNAVFAGENFHHGDKL |
| 14 | 2828.2985 | 2828.2888 | -3.4 | 103 | 116.1 | 100.2 | 15.9 | 2.98 | 2.50 | 0.5 | YPIVSIEDPFAEDDWEAWSHFFK |
| 15 | 2984.3924 | 2984.3898 | -0.9 | 99.6 | 111.4 | 96.6 | 14.8 | 3.03 | 3.00 | 0.0 | RYPIVSIEDPFAEDDWEAWSHFFK |

FIG. 9E

| Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|
| ENOLASE 2 | | | | | | | | | | 42% |
| 1 | 1100.5217 | 1100.5268 | 4.6 | 36.2 | 32.4 | 34.4 | 2.0 | 2.00 | 2.00 | 0.0 | DGKYDLDFK |
| 2 | 1159.6101 | 1159.6108 | 0.6 | 22.9 | 15.9 | 18.7 | 2.8 | 2.00 | 2.00 | 0.0 | IGSEVYHNLK |
| 3 | 1288.7073 | 1288.7108 | 2.7 | 40.4 | 37.7 | 17.9 | 19.8 | 2.00 | 2.00 | 0.0 | VNQIGTLSESIK |
| 4 | 1373.6400 | 1373.6408 | 0.6 | 58.4 | 60.1 | 46.6 | 13.5 | 2.00 | 2.00 | 0.0 | IGLDCASSEFFK |
| 5 | 1416.7245 | 1416.7218 | -1.9 | 39.4 | 36.4 | 9.2 | 27.2 | 2.00 | 2.00 | 0.0 | GNPTVEVELTTEK |
| 6 | 1557.7377 | 1557.7448 | 4.6 | 40.8 | 38.2 | 43.8 | 5.6 | 2.00 | 2.00 | 0.0 | AVYAGENFHHGDKL |
| 7 | 1578.8048 | 1578.8018 | -1.9 | 64.4 | 67.5 | 81.3 | 13.8 | 2.00 | 2.00 | 0.0 | AVDDFLLSLDGTANK |
| 8 | 1840.9287 | 1840.9228 | -3.2 | 52.2 | 52.4 | 31.7 | 20.7 | 2.28 | 2.15 | 0.1 | SIVPSGASTGVHEALEMR |
| 9 | 2328.1112 | 2328.1138 | 1.1 | 45.9 | 44.5 | 15.1 | 29.4 | 3.00 | 3.00 | 0.0 | SIVPSGASTGVHEALEMR DEDK |
| 10 | 2828.2985 | 2828.2888 | -3.4 | 103 | 116.1 | 100.2 | 15.9 | 2.98 | 2.50 | 0.5 | YPIVSIEDPFAEDDWEAW SHFFK |
| 11 | 2984.4124 | 2984.3998 | -4.2 | 99.6 | 111.4 | 96.6 | 14.8 | 3.03 | 3.00 | 0.0 | RYPIVSIEDPFAEDDWEA WSHFFK |

FIG. 9F

| Obs. MH+ | Actual MH+ | Mass Error ppm | RT | Obs. HPLC Index | Theor HPLC Index | HPLC Diff | Obs. CS | Theor CS | CS Diff. | Sequence |
|---|---|---|---|---|---|---|---|---|---|---|
| GLUCOSE OXIDASE | | | | | | | | | | 32% |
| 1 1003.4925 | 1003.4958 | 3.3 | 6.1 | -5.0 | 5.7 | 10.7 | 2.00 | 2.00 | 0.0 | GNTHNVYAK |
| 2 1044.5446 | 1044.5478 | 3.1 | 23.9 | 17.1 | 25.6 | 8.5 | 2.00 | 2.00 | 0.0 | AVGVEFGTHK |
| 3 1209.5640 | 1209.5638 | -0.2 | 22.7 | 15.6 | 10.8 | 4.8 | 2.00 | 2.00 | 0.0 | DTGDDYSPIVK |
| 4 1301.6447 | 1301.6488 | 3.1 | 40.3 | 37.5 | 43.1 | 5.6 | 2.00 | 2.00 | 0.0 | LEQWAEEAVAR |
| 5 1455.6694 | 1455.6678 | -1.1 | 59.6 | 61.6 | 44.5 | 17.1 | 2.00 | 2.00 | 0.0 | ISDAILEDYASMQ( |
| 6 1850.0122 | 1850.0118 | -0.2 | 64.3 | 67.4 | 83.0 | 15.6 | 2.00 | 2.00 | 0.0 | TVDYIIAGGGLTGLTTAAR |
| 7 1990.9938 | 1991.0008 | 3.5 | 48.4 | 47.6 | 38.7 | 8.9 | 3.00 | 2.00 | 1.0 | EMGGVVDNAARVYGVQ |
| 8 2443.2984 | 2443.2908 | -3.1 | 77.5 | 83.9 | 90.2 | 6.3 | 2.86 | 2.50 | 0.4 | HEVLLAAGSAVSPTILEYS GIGMK |
| 9 2615.1537 | 2615.1408 | -4.9 | 55.8 | 56.8 | 42.1 | 14.7 | 3.17 | 3.20 | 0.0 | DFGCGDPHGVSMFPNTL HEDQVR |
| 10 3077.6959 | 3077.6938 | -0.7 | 92.9 | 103.0 | 122.3 | 19.3 | 2.85 | 3.20 | 0.4 | SILEPLGIDTVVDLPVGLN LQDQTTATVR |
| 11 3342.5363 | 3342.5288 | -2.2 | 85.9 | 94.3 | 82.1 | 12.2 | 2.90 | 3.20 | 0.3 | AQVDSWETVFGNEGWN DNVAAYSLQAER |

Sequence Coverage

FIG. 9G

| Obs. MH+ | Actual MH+ | Mass Error ppm | RT | Obs. HPLC Index | Theor HPLC Index | HPLCI Diff | Obs. CS | Theor CS | CS Diff. | Sequence |
|---|---|---|---|---|---|---|---|---|---|---|
| GLYCOGEN PHOSPHORYLASE | | | | | | | Sequence Coverage | | | 50% |
| 1053.5690 | 1053.5728 | 3.6 | 51.1 | 51.0 | 45.4 | 5.6 | 2.00 | 2.00 | 0.0 | VIFLENYR |
| 1145.5619 | 1145.5628 | 0.8 | 55.2 | 56.2 | 39.5 | 16.7 | 2.00 | 2.00 | 0.0 | YEFGIFNQK |
| 1177.5530 | 1177.5528 | -0.2 | 39.0 | 35.9 | 33.9 | 2.0 | 2.00 | 2.00 | 0.0 | DFYELEPHK |
| 1229.6724 | 1229.6738 | 1.1 | 42.5 | 40.3 | 35.7 | 4.6 | 2.00 | 2.00 | 0.0 | GLAGVENVTELK |
| 1253.6402 | 1253.6408 | 0.5 | 40.5 | 37.8 | 15.3 | 22.5 | 2.05 | 2.00 | 0.0 | CQERVSALYK |
| 1262.5983 | 1262.5948 | -2.8 | 43.3 | 41.3 | 31.1 | 10.2 | 2.00 | 2.00 | 0.0 | VFADYEEYVK |
| 1278.5432 | 1278.5388 | -3.4 | 21.7 | 14.5 | 10.8 | 3.7 | 2.00 | 2.00 | 0.0 | GYNAQEYYDR |
| 1355.6758 | 1355.6748 | -0.7 | 53.0 | 53.3 | 67.9 | 14.6 | 2.00 | 2.00 | 0.0 | DYYFALAHTVR |
| 1357.7584 | 1357.7588 | 0.3 | 40.3 | 37.5 | 32.0 | 5.5 | 2.00 | 2.00 | 0.0 | GLAGVENVTELKK |
| 1426.7832 | 1426.7808 | -1.7 | 51.6 | 51.6 | 33.2 | 18.4 | 2.00 | 2.00 | 0.0 | HLQIIYEINQR |
| 1440.7373 | 1440.7378 | 0.3 | 59.9 | 61.9 | 68.5 | 6.6 | 2.00 | 2.00 | 0.0 | LLSYVDDEAFIR |
| 1442.7004 | 1442.6958 | -3.2 | 54.1 | 54.7 | 53.2 | 1.5 | 2.00 | 2.00 | 0.0 | VLYPNDNFFEGK |
| 1473.8544 | 1473.8578 | 2.3 | 84.1 | 92.1 | 104.6 | 12.5 | 2.01 | 2.00 | 0.0 | WPVHLLETLLPR |
| 1550.7702 | 1550.7698 | -0.3 | 59.4 | 61.4 | 36.5 | 24.9 | 2.00 | 2.00 | 0.0 | IGEEYISDLDQLR |
| 1554.7635 | 1554.7668 | 2.1 | 80.7 | 87.9 | 79.7 | 8.2 | 2.00 | 2.00 | 0.0 | IYYLSLEFYMGR |
| 1609.8735 | 1609.8698 | -2.3 | 60.7 | 62.9 | 43.5 | 19.4 | 2.00 | 2.15 | 0.2 | VHINPNSLFDVQVK |
| 1666.8411 | 1666.8478 | 4.0 | 60.5 | 62.7 | 56.8 | 5.9 | 2.80 | 2.75 | 0.0 | TIFKDFYELEPHK |
| 1689.8763 | 1689.8768 | 0.3 | 61.8 | 64.4 | 75.1 | 10.7 | 3.00 | 3.00 | 0.0 | ARPEFTLPVHFYGR |
| 1756.9566 | 1756.9528 | -2.2 | 66.5 | 70.2 | 76.8 | 6.6 | 2.46 | 2.50 | 0.0 | QLLNCLHVITLYNR |

FIG. 9H

| Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|
| GLYCOGEN PHOSPHORYLASE | | | | | | | | | | 50% |
| 20 1765.9608 | 1765.9688 | 4.5 | 59.6 | 61.6 | 73.1 | 11.5 | 2.89 | 3.00 | 0.1 | QEYFVVAATLQDIIR |
| 21 1840.9287 | 1840.9238 | -2.7 | 52.2 | 52.4 | 62.5 | 10.1 | 2.28 | 2.15 | 0.1 | VLYPNDNFFEGKELR |
| 22 1854.0020 | 1853.9948 | -3.9 | 83.5 | 91.4 | 85.4 | 6.0 | 2.00 | 2.00 | 0.0 | WLVLCNPGLAEIIAER |
| 23 1865.8046 | 1865.8048 | 0.1 | 65.1 | 68.5 | 43.2 | 25.3 | 2.00 | 2.00 | 0.0 | ICGGWQMEEADDWLR |
| 24 1874.9032 | 1874.9068 | 1.9 | 44.8 | 43.1 | 43.3 | 0.2 | 2.89 | 3.00 | 0.1 | TCAYTNHTVLPEALER |
| 25 1890.0078 | 1890.0088 | 0.5 | 59.7 | 61.7 | 44.5 | 17.2 | 2.68 | 3.00 | 0.3 | LITAIGDVVNHDPVVGDR |
| 26 1990.9938 | 1991.0008 | 3.5 | 48.4 | 47.6 | 46.7 | 0.9 | 3.00 | 2.50 | 0.5 | INMAHLCIAGSHAVNGVAR |
| 27 2033.0317 | 2033.0358 | 2.0 | 65.0 | 68.3 | 81.6 | 13.3 | 3.00 | 2.50 | 0.5 | DYYFALAHTVRDHLVGR |
| 28 2118.1411 | 2118.1378 | -1.6 | 72.8 | 78.0 | 88.7 | 10.7 | 2.93 | 3.00 | 0.1 | VAIQLNDTHPSLAIPELMR |
| 29 2307.1678 | 2307.1688 | 0.4 | 74.7 | 80.4 | 87.6 | 7.2 | 2.07 | 2.00 | 0.1 | WVDTQVVLAMPYDTPVP GYR |
| 30 2448.2091 | 2448.2028 | -2.6 | 54.7 | 55.4 | 42.9 | 12.5 | 2.20 | 2.50 | 0.3 | VIPAADLSEQISTAGTEAS GTGNMK |

Sequence Coverage

FIG. 9I

| Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|
| LACTOPEROXIDASE | | | | | | | | | | 33% |
| 910.5061 | 910.5068 | 0.8 | 36.2 | 32.5 | 47.8 | 15.3 | 2.00 | 2.00 | 0.0 | KLMDLYK |
| 1168.6844 | 1168.6878 | 2.9 | 77.3 | 83.6 | 87.3 | 3.7 | 2.00 | 2.00 | 0.0 | VGPLLACLLGR |
| 1181.5736 | 1181.5778 | 3.6 | 59.7 | 61.7 | 64.0 | 2.3 | 2.00 | 2.00 | 0.0 | VPCFLAGDFR |
| 1201.6357 | 1201.6368 | 0.9 | 72.4 | 77.5 | 69.0 | 8.5 | 2.00 | 2.00 | 0.0 | ISNVFTFAFR |
| 1214.6183 | 1214.6198 | 1.2 | 21.7 | 14.4 | 17.8 | 3.4 | 2.02 | 2.00 | 0.0 | LICDNTHITK |
| 1319.5617 | 1319.5588 | -2.2 | 35.9 | 32.1 | 18.7 | 13.4 | 2.00 | 2.00 | 0.0 | DHGMPGYNSWR |
| 1345.6880 | 1345.6868 | -0.9 | 44.4 | 42.7 | 13.6 | 29.1 | 2.00 | 2.00 | 0.0 | NGQVWEESLKR |
| 1391.8452 | 1391.8418 | -2.4 | 93.0 | 103.2 | 94.4 | 8.8 | 2.00 | 2.00 | 0.0 | ILGAFIQIITFR |
| 1467.8100 | 1467.8068 | -2.2 | 62.2 | 64.8 | 77.8 | 13.0 | 2.00 | 2.15 | 0.2 | IHGFDLAAINLQR |
| 1492.7750 | 1492.7718 | -2.1 | 63.7 | 66.7 | 54.0 | 12.7 | 2.00 | 2.00 | 0.0 | DYLPIVLGSEMQK |
| 1539.7279 | 1539.7268 | -0.7 | 71.5 | 76.4 | 62.2 | 14.2 | 2.00 | 2.00 | 0.0 | FWWENPGVFTEK |

Sequence Coverage

FIG. 9J

| Obs. MH+ | Actual MH+ | Mass Error ppm | RT | Obs. HPLC Index | Theor HPLC Index | HPLCi Diff | Obs. CS | Theor CS | CS Diff. | Sequence |
|---|---|---|---|---|---|---|---|---|---|---|
| LACTOPEROXIDASE | | | | | | | | Sequence Coverage | | 33% |
| 12 | 1663.8301 | 1663.8268 | -2.0 | 51.4 | 51.4 | 67.5 | 16.1 | 2.00 | 2.00 | 0.0 | AGFVCPTPPYQSLAR |
| 13 | 1719.8620 | 1719.8548 | -4.2 | 51.0 | 50.8 | 34.1 | 16.7 | 2.00 | 2.00 | 0.0 | IVGYLDEEGVLDQNR |
| 14 | 2654.3463 | 2654.3408 | -2.1 | 84.4 | 92.4 | 84.7 | 7.7 | 2.36 | 2.50 | 0.1 | EQINAVTSFLDASLVYGSEPSLASR |
| 15 | 2674.2407 | 2674.2358 | -1.8 | 54.3 | 55.0 | 65.4 | 10.4 | 3.27 | 3.20 | 0.1 | VPLHAFQANNYPHDFVDCSTVDK |
| 16 | 3443.6405 | 3443.6318 | -2.5 | 102 | 114.3 | 111.3 | 3.0 | 3.56 | 3.20 | 0.4 | SLLFMQWGQIVDHDLDFAPETELGSNEHSK |
| LYSOZYME C | | | | | | | | Sequence Coverage | | 64% |
| 1 | 993.4005 | 993.3998 | -0.7 | 22.7 | 15.7 | 16.6 | 0.9 | 2.00 | 2.00 | 0.0 | WWCNDGR |
| 2 | 1045.5410 | 1045.5428 | 1.7 | 42.0 | 39.6 | 33.1 | 6.5 | 2.00 | 2.00 | 0.0 | GTDVQAWIR |
| 3 | 1325.6338 | 1325.6308 | -2.3 | 54.7 | 55.5 | 41.8 | 13.7 | 2.00 | 2.00 | 0.0 | GYSLGNWVCAAK |
| 4 | 1352.6804 | 1352.6818 | 1.0 | 58.0 | 59.6 | 52.0 | 7.6 | 2.00 | 2.00 | 0.0 | VFGRCELAAAMK |
| 5 | 1428.6503 | 1428.6508 | 0.3 | 22.3 | 15.1 | 21.7 | 6.6 | 2.00 | 2.00 | 0.0 | FESNFNTQATNR |
| 6 | 1753.8418 | 1753.8358 | -3.4 | 45.0 | 43.3 | 15.6 | 27.7 | 2.00 | 2.00 | 0.0 | NTDGSTDYGILQINSR |
| 7 | 2508.2044 | 2508.1998 | -1.8 | 65.2 | 68.5 | 43.4 | 25.1 | 2.27 | 2.50 | 0.2 | NLCNIPCSALLSSDITASVNCAK |

FIG. 9K

| | Obs. MH+ | Actual MH+ | Mass Error ppm | RT | Obs. HPLC Index | Theor HPLC Index | HPLCI Diff | Obs. CS | Theor CS | CS Diff. | Sequence |
|---|---|---|---|---|---|---|---|---|---|---|---|
| RIBONUCLEASE | | | | | | | | | | | Sequence Coverage 29% |
| 1 | 915.4034 | 915.4038 | 0.4 | 2.1 | -10.0 | 12.2 | 22.2 | 2.00 | 2.00 | 0.0 | YPNCAYK |
| 2 | 1558.7341 | 1558.7328 | -0.8 | 40.8 | 38.2 | 11.4 | 26.8 | 3.00 | 2.00 | 1.0 | YPNCAYKTTQANK |
| 3 | 2224.0938 | 2224.0858 | -3.6 | 62.8 | 65.5 | 49.3 | 16.2 | 2.53 | 2.50 | 0.0 | HIIVACEGNPYVPVHFDASV |
| SERUM ALBUMIN | | | | | | | | | | | Sequence Coverage 67% |
| 1 | 974.4546 | 974.4578 | 3.3 | 21.7 | 14.5 | 21.7 | 7.2 | 2.00 | 2.00 | 0.0 | DLGEEHFK |
| 2 | 1014.6145 | 1014.6158 | 1.3 | 59.7 | 61.7 | 67.1 | 5.4 | 3.00 | 2.00 | 0.0 | QTALVELLK |
| 3 | 1034.4719 | 1034.4728 | 0.9 | 21.9 | 14.7 | 13.9 | 0.8 | 2.53 | 2.00 | 0.0 | NECFLSHK |
| 4 | 1072.5071 | 1072.5098 | 2.5 | 6.6 | -4.3 | -9.3 | 5.0 | 2.00 | 2.00 | 0.0 | SHCIAEVEK |
| 5 | 1142.7132 | 1142.7148 | 1.4 | 54.6 | 55.4 | 63.4 | 8.0 | 2.00 | 2.00 | 0.0 | KQTALVELLK |
| 6 | 1163.6293 | 1163.6308 | 1.3 | 50.6 | 50.4 | 53.8 | 3.4 | 2.00 | 2.00 | 0.0 | LVNELTEFAK |
| 7 | 1249.6200 | 1249.6218 | 1.4 | 32.1 | 27.3 | 37.2 | 9.9 | 2.22 | 2.15 | 0.1 | FKDLGEEHFK |
| 8 | 1283.7121 | 1283.7108 | -1.0 | 56.9 | 58.2 | 55.0 | 3.2 | 2.00 | 2.00 | 0.0 | HPEYAVSVLLR |
| 9 | 1291.6036 | 1291.6028 | -0.6 | 21.8 | 14.5 | 8.8 | 5.7 | 2.00 | 2.00 | 0.0 | ECCDKPLLEK |
| 10 | 1305.7071 | 1305.7068 | -0.2 | 40.5 | 37.8 | 40.0 | 2.2 | 2.00 | 2.00 | 0.0 | HLVDEPQNLIK |
| 11 | 1399.6947 | 1399.6928 | -1.4 | 71.9 | 76.8 | 49.8 | 27.0 | 2.00 | 2.00 | 0.0 | TVMENFVAFVDK |
| 12 | 1419.6967 | 1419.6938 | -2.0 | 55.7 | 56.7 | 56.3 | 0.4 | 2.04 | 2.00 | 0.0 | SLHTLFGDELCK |
| 13 | 1439.8099 | 1439.8118 | 1.3 | 54.4 | 55.1 | 51.4 | 3.7 | 2.31 | 2.50 | 0.2 | RHPEYAVSVLLR |
| 14 | 1443.6496 | 1443.6428 | -4.7 | 2.5 | -9.5 | -6.4 | 3.1 | 2.00 | 2.00 | 0.0 | YICDNQDTISSK |

FIG. 9L

| | Obs. MH+ | Actual MH+ | Mass Error ppm | RT | Obs. HPLC Index | Theor. HPLC Index | HPLCi Diff | Obs. CS | Theor CS | CS Diff. | Sequence |
|---|---|---|---|---|---|---|---|---|---|---|---|
| SERUM ALBUMIN | | | | | | | | | | | 67% |
| 15 | 1463.5911 | 1463.5898 | -0.9 | 6.2 | -4.9 | -21.1 | 16.2 | 2.00 | 2.15 | 0.2 | TCVADESHAGCEK |
| 16 | 1479.7951 | 1479.7958 | 0.5 | 60.3 | 62.5 | 70.0 | 7.5 | 2.00 | 2.00 | 0.0 | LGEYGFQNALIVR |
| 17 | 1502.6188 | 1502.6138 | -3.3 | 22.0 | 14.8 | -2.6 | 17.4 | 2.00 | 2.00 | 0.0 | EYEATLEECCAK |
| 18 | 1510.8350 | 1510.8327 | -1.5 | 36.8 | 33.2 | 22.2 | 11 | 2.00 | 2.00 | 0 | VPQVSTPTLVEVSR |
| 19 | 1532.7737 | 1532.7718 | -1.2 | 22.8 | 15.7 | 25.1 | 9.4 | 2.68 | 2.50 | 0.2 | LKECCDKPLLEK |
| 20 | 1554.6599 | 1554.6538 | -3.9 | 35.5 | 31.6 | 20.6 | 11.0 | 2.00 | 2.15 | 0.2 | DDPHACYSTVFDK |
| 21 | 1567.7451 | 1567.7428 | -1.5 | 77.3 | 83.6 | 81.1 | 2.5 | 2.00 | 2.00 | 0.0 | DAFLGSFLYEYSR |
| 22 | 1575.7600 | 1575.7598 | -0.1 | 43.5 | 41.6 | 44.2 | 0.6 | 2.00 | 2.15 | 0.2 | LKPDPNTLCDEFK |
| 23 | 1639.9443 | 1639.9378 | -4.0 | 46.0 | 44.6 | 29.5 | 15.1 | 2.00 | 2.15 | 0.2 | KVPQVSTPTLVEVSR |
| 24 | 1724.8376 | 1724.8348 | -1.6 | 80.6 | 87.7 | 58.0 | 29.7 | 2.00 | 2.00 | 0.0 | MPCTEDYLSLILNR |
| 25 | 1880.9320 | 1880.9318 | -0.1 | 51.2 | 51.2 | 48.8 | 2.4 | 2.00 | 2.15 | 0.2 | RPCFSALTPDETYVPK |
| 26 | 1888.9369 | 1888.9278 | -4.8 | 70.7 | 75.4 | 95.6 | 20.2 | 2.00 | 2.15 | 0.2 | HPYFYAPELLYYANK |
| 27 | 1901.8646 | 1901.8698 | 2.7 | 39.9 | 37.0 | 27.6 | 9.4 | 2.88 | 2.50 | 0.4 | NECFLSHKDDSPDLPK |
| 28 | 1907.9209 | 1907.9208 | -0.1 | 60.9 | 63.3 | 78.5 | 15.2 | 2.72 | 2.50 | 0.2 | LFTFHADICTLPDTEK |
| 29 | 2019.9676 | 2019.9698 | 1.1 | 40.7 | 38.1 | 35.2 | 2.9 | 2.96 | 3.00 | 0.0 | LKPDPNTLCDEFKADEK |
| 30 | 2045.0290 | 2045.0288 | -0.1 | 67.5 | 71.4 | 92.0 | 20.6 | 2.74 | 2.65 | 0.1 | RHPYFYAPELLYYANK |
| 31 | 2458.1886 | 2458.1808 | -3.2 | 61.9 | 64.5 | 65.8 | 1.3 | 2.92 | 3.00 | 0.1 | DAIPENLPPLTADFAEDKDVCK |
| 32 | 2492.2753 | 2492.2648 | -4.2 | 89.9 | 99.3 | 105.7 | 6.4 | 2.95 | 2.50 | 0.5 | GLVLIAFSQYLQQCPFDEHVK |

FIG. 9M

| Avg. RT | Avg MH+ | Normalized Low Dose Intensity | | | Normalized High Dose Intensity | | | Abundance Change | p-Score |
| --- | --- | --- | --- | --- | --- | --- | --- | --- | --- |
| | | Inj 1 | Inj 2 | Inj 3 | Inj 1 | Inj 2 | Inj 3 | | |
| 48.65 | 319.1417 | 413.56 | 451.27 | 421.27 | 7938.03 | 6222.29 | 7410.21 | 16.77 | 0.0029 |
| 36.14 | 192.9818 | 26.17 | 30.62 | 29.99 | 407.90 | 473.64 | 399.50 | 14.76 | 0.0016 |
| 40.64 | 209.9866 | 25.01 | 28.23 | 23.32 | 392.38 | 302.09 | 324.09 | 13.30 | 0.0039 |
| 36.07 | 433.1172 | 37.22 | 40.11 | 39.88 | 530.53 | 428.37 | 527.46 | 12.68 | 0.0028 |
| 38.32 | 315.0882 | 24.91 | 32.27 | 29.74 | 352.14 | 363.40 | 324.56 | 11.97 | 0.0007 |
| 50.83 | 287.1573 | 39.32 | 48.52 | 43.54 | 578.98 | 442.16 | 519.61 | 11.73 | 0.0040 |
| 44.02 | 203.0540 | 87.28 | 120.92 | 119.06 | 1215.05 | 1208.65 | 1196.31 | 11.06 | 0.0001 |
| 33.82 | 291.1976 | 25.31 | 25.53 | 20.91 | 300.09 | 245.49 | 245.77 | 11.03 | 0.0026 |
| 42.69 | 215.0178 | 85.76 | 69.55 | 58.20 | 797.51 | 790.05 | 667.34 | 10.56 | 0.0014 |
| 43.24 | 299.1386 | 367.80 | 451.34 | 399.19 | 4236.71 | 3427.31 | 3747.13 | 9.37 | 0.0029 |
| 54.34 | 293.2148 | 25.87 | 32.77 | 29.72 | 296.22 | 250.15 | 268.61 | 9.22 | 0.0020 |
| 35.79 | 243.1147 | 65.48 | 58.15 | 57.84 | 524.13 | 594.80 | 521.30 | 9.04 | 0.0013 |
| 30.45 | 365.2370 | 68.82 | 59.99 | 52.56 | 565.95 | 511.89 | 495.80 | 8.68 | 0.0006 |
| 36.07 | 431.1120 | 444.55 | 390.26 | 376.09 | 3240.02 | 2549.03 | 3122.30 | 7.36 | 0.0031 |
| 36.14 | 193.0491 | 37.93 | 38.89 | 32.53 | 302.15 | 225.54 | 252.71 | 7.14 | 0.0050 |
| 35.79 | 215.1620 | 161.33 | 118.37 | 95.68 | 952.30 | 831.84 | 769.74 | 6.80 | 0.0011 |
| 41.27 | 331.2322 | 100.12 | 70.85 | 63.05 | 532.72 | 456.69 | 474.10 | 6.25 | 0.0005 |
| 18.20 | 202.0556 | 200.51 | 170.14 | 143.72 | 999.28 | 803.61 | 844.09 | 5.15 | 0.0023 |
| 34.52 | 325.2098 | 51.66 | 52.70 | 45.74 | 254.94 | 276.74 | 221.25 | 5.02 | 0.0024 |
| 34.03 | 260.1525 | 7886.64 | 9276.61 | 7612.38 | 2291.91 | 1930.65 | 1880.74 | 0.25 | 0.0040 |
| 33.26 | 234.0990 | 468.09 | 405.77 | 399.49 | 82.65 | 122.90 | 81.37 | 0.23 | 0.0041 |
| 43.17 | 318.1936 | 449.31 | 448.82 | 391.68 | 85.22 | 71.97 | 74.37 | 0.18 | 0.0013 |
| 37.05 | 337.2423 | 239.88 | 224.03 | 183.98 | 31.15 | 49.81 | 25.58 | 0.16 | 0.0034 |
| 18.80 | 202.1467 | 373.78 | 405.23 | 369.31 | 61.80 | 62.91 | 56.32 | 0.16 | 0.0005 |
| 43.24 | 299.1623 | 455.28 | 447.49 | 421.41 | 68.87 | 50.29 | 64.85 | 0.14 | 0.0005 |
| 39.80 | 351.2019 | 359.03 | 404.65 | 341.35 | 29.78 | 36.24 | 25.12 | 0.08 | 0.0011 |
| 35.65 | 437.2397 | 895.33 | 1015.08 | 976.73 | 68.54 | 48.85 | 65.95 | 0.06 | 0.0010 |

FIG. 10

METHOD OF ANALYZING DIFFERENTIAL EXPRESSION OF PROTEINS IN PROTEOMES BY MASS SPECTROMETRY

The present invention relates a method of mass spectrometry. The preferred embodiment relates to protein identification, protein quantitation, proteases, high-resolution mass spectrometry, proteomics, genomics, and bioinformatics.

The growing importance of genomic and proteomic information in biotechnology and pharmaceutical research and development has stimulated the development of many innovative technologies. Technology platforms such as transcriptional profiling or gene expression analysis are making it possible to better understand cellular physiology and to develop correlations between gene expression (mRNA) and cellular responses to internal and environmental stimuli. See, J. L. DeRisi et al., Exploring the metabolic and genetic control of gene expression on a genomic scale, *Science* 278:680-686 (1997); F. P. Roth et al., Finding DNA regulatory motifs within unaligned noncoding sequences clustered by whole-genome mRNA Quantitation, *Nat. Biotechnol.* 16:939-945 (1998). Internal stimuli include genetic variations and disease states, while external stimuli include changes in environmental conditions (e.g., temperature, pH, osmolality, etc.) or chemical concentrations (e.g., drugs, hormones, toxins, etc.) Understanding how gene expression profiles vary dynamically as conditions fluctuate can provide valuable insight into the identification and development of novel therapeutic targets, treatments and disease progression/regression markers (biomarkers). Elucidating changes in expression profiles should allow for a greater understanding of many biochemical processes on a macroscopic level.

Gene expression analysis techniques measure changes in mRNA levels and relate these changes to a cellular response characteristic to a given stimulus. The field has expanded considerably with the development of DNA arrays (e.g., the GeneChip™ arrays marketed by Affymetrix, Santa Clara, Calif.). However, research in this field has demonstrated that there is often a poor correlation between measured mRNA levels and levels of the actual protein encoded by the mRNA. See S. P. Gygi et al., Correlation between protein and mRNA abundance in yeast, *Mol. Cell. Biol.* 19:1720-1730 (1999); L. M. Hartford and D. R. Morris, Post-transcriptional gene regulation, Wiley-Liss Inc (1997); and A. Varshavsky, The N-end rule: functions, mysteries, uses, *Proc. Natl. Acad. Sci. USA*, 93:12142-12149 (1996). The discrepancy can be attributed to a variety of factors such as poor experimental reproducibility across various transcriptional profiling platforms, effects of cellular compartmentalization, translation efficiency, post-translational modifications, and protein degradation systems.

An improved approach to quantitative proteomics would complement the existing genomic approaches, by directly examining the proteins involved in cellular processes. A combination of these two technologies will lead to a more complete conceptual understanding of the functional architecture of genome and proteome networks, allowing for a more comprehensive view of a cell's physiology.

Two common goals in proteomic research are to qualitatively identify the proteins present in a cell given a set of conditions and to quantitatively determine the relative levels of these proteins as those conditions change. Unfortunately, the majority of current analytical approaches in proteomics yield either qualitative information or a rudimentary level of quantitative information. Reliable and accurate methods for quantitatively measuring the relative expression levels of proteins are lacking. The ability to elicit this quantitative information is crucial to proteomics and will aid in the enhancement of discovery and development of drugs, development of novel protein based diagnostic/prognostic tests, and monitoring the efficacy of drug treatment strategies (biomarkers). Some of the existing methods associated with the identification of proteins and current technologies designed to quantitate proteins will now be briefly described.

The utility of both single stage and tandem mass spectrometry for the identification of cellular proteins using protein and nucleotide databases is well documented. In single stage mass spectrometry the instrument of choice has been a Matrix Assisted Laser Desorption Ionization (MALDI) Time of Flight Mass Spectrometer (TOF-MS or MALDI-TOF). The MALDI instrument characteristically generates a mass spectrum of singly charged peptide ions with a mass accuracy of 20 to 50 ppm. The generated list of peptide ion mass values is then presented to any of a number of previously described search-engines for protein identification (see Mann et al., Use of mass spectrometric molecular weight information to identify proteins in sequence databases, *Biological Mass Spectr.* 22(6): 338-45 (1993); Henzel et al., Identification of 2-D Gel Proteins at the femtomole level by Molecular Mass Searching of Peptide Fragments in a Protein Sequence Database, *Techniques in Protein Chemistry V*, John Crabb ed., (1994); and Pappin et al., Peptide Mass Fingerprinting using MALDI-TOF mass spectrometry, *Current Biology* 3:327-332 (1993)). Those skilled in the art have coined the name Peptide Mass Fingerprinting ("PMF") for this method of identifying proteins. Although peptide mass fingerprinting has been shown to facilitate the identification of multiple proteins in simple mixtures (Jensen et al., *Anal. Chem.* 69(23): 4741-50 (1997)), the technique's limited accuracy leads to ambiguities when it is applied to complex mixtures, and the likelihood of false positive assignments rises to unacceptable levels. Additionally, peptide mass fingerprinting cannot be used reliably for quantitative analysis because of ion suppression problems associated with the MALDI ionization process. Among the other mass spectrometer designs that have been employed for protein analysis are triple-stage quadrupole (TSQ) instruments and quadrupole ion trap (QIT) devices. Both types of instrument are also suitable for MS/MS applications (described below) but tend to be limited to mass accuracies of 50 to 100 ppm, and low sensitivity due to the scanning nature of the design. QIT instruments also have a relatively limited charge capacity and consequently have a limited dynamic range.

An alternative approach to peptide mass fingerprinting involves tandem mass spectrometry (MS/MS). Tandem mass spectrometric identification of proteins involves the acquisition and analysis of the mass spectrum of product ions generated from each precursor ion selected in the primary mass spectrum of a set of proteolyzed protein fragments. The additional information is helpful in that different protein fragments with the same nominal mass, can be distinguished by their product ion spectra. MS/MS data may also be used to deduce the amino acid sequence of the protein fragment precursor ions, and the resulting sequence can be compared to a protein or translated nucleotide databases for protein identification. Tandem mass spectrometric identifications greatly improve the confidence of MALDI-TOF based protein identifications by providing primary sequence data that confirm the identity generated by the peptide mass fingerprint. See Wilm and Mann, Error-tolerant identification of peptides in sequence databases by peptide sequence tags, *Anal. Chem.* 66:4390-4399 (1994); W. Hines et al., Pattern-Based Algorithm for Peptide Sequencing from Tandem High Energy Collision-Induced Dissociation Mass Spectra, *J. Am. Soc. Mass Spectrom*, 3:326-336 (1992); V. Dancik et al., De Novo Peptide Sequencing via Tandem Mass Spectrometry: A Graph-Theoretical Approach, *RECOMB*, 135-144 (1999); and Yates et al., U.S. Pat. No. 5,538,897.

Although useful in providing a system for rapidly correlating fragment spectra with known protein sequences, the algorithm within these automated processes assigns a most probable match to every spectrum and the user has to rely on multiple unique peptide assignments to the same protein fragment to offset the probability of generating false positives from the peptide MS/MS data. MS/MS-based strategies for protein identification can involve automatic switching between MS and MS/MS modes of analysis on any polypeptide ion, which satisfies user-defined criteria. Switching to the MS/MS mode interrupts data collection in the MS mode, and because only one precursor ion at a time can be analyzed, the net throughput of the system is limited. MS/MS analysis of every ion in the primary spectrum of a mixture as complex as a proteome would be extremely time and sample consuming. To achieve comprehensive protein coverage of a complex heterogeneous mixture, as in the case of a proteome, MS/MS switching must occur very often, and this compromises the quality of both the MS and MS/MS data. Compromising the quality of the tentative identifications MS spectra significantly decreases the quantitative accuracy of the experiment. Compromising the quality of peptide MS/MS spectra significantly increases the probability of generating false positive identifications, especially in a proteome where the components of the mixture are not present in equimolar quantities and the number of ions derived from some proteins is low.

Many scientists have extracted or dissected 2-D protein gels, and subjected the separated proteins to mass spectroscopy for characterization and possible identification by the methods described above. See for example, H. Nakayama, et al., Capillary column high-performance liquid chromatographic-electrospray ionization triple-stage mass spectrometric analysis of proteins separated by two-dimensional polyacrylamide gel electrophoresis. Application to cerebellar protein mapping, *J. Chrom. A* 730:279-287 (1996); S. M. Hanash, Biomedical applications of two-dimensional electrophoresis using immobilized pH gradients: current status, *Electrophoresis* 21:1202-1209 (2000); A. Pandey, M. Mann, Proteomics to study genes and genomes, *Nature* 405:837-846 (2000); M. P. Washburn, J. R. Yates, Analysis of the microbial proteome, *Curr. Opin. Microbiol.* 3:292-297 (2000); H. Langen et al., Two-dimensional map of the proteome of *Haemophilus influenzae*, *Electrophoresis*, 21:411-429 (2000). Such hybrid methods are quite sensitive, but are limited by the resolving capacity of the 2D gel itself and require tedious extraction and analysis of individual spots on the gel.

One approach suggested by those skilled in proteomics involves generating a complex peptide mixture by enzymatically digesting all the protein members of a given proteome, followed by chromatographic separations interfaced to mass spectrometric techniques such as Fourier Transform Ion Cyclotron Resonance (FTICR; see L. Li et al., High-throughput peptide identification from protein digests using data-dependent multiplexed tandem FTICR Mass spectrometry coupled with capillary liquid chromatography, *Anal. Chem.* 73:3312-33222 (2001); Y. Shen et al., High-Throughput Proteomics Using High-Efficiency Multiple-Capillary Liquid Chromatography with On-Line High-Performance ESI FTICR Mass Spectrometry, *Anal. Chem.* 73:3011-3021 (2001)). This is a very promising approach, but the instrumentation required for FTICR is extremely expensive. An FTICR spectrometer can cost in excess of five million dollars, making the method impractical for widespread routine use.

Another is a tandem mass spectrometric technique called Multi-Dimensional Protein Identification Technology ("MudPIT") (A. Link et al., Direct Analysis of Protein Complexes Using Mass Spectrometry, *Nat. Biotechnol.* 17:676-682 (1999); M. P. Washburn et al., Large-Scale Analysis of the Yeast Proteome by Multidimensional Protein Identification Technology, *Nat. Biotechnol.* 19:242-247 (2001). This technique, actually a type of chromatography applied to pre-fractionate samples prior to tandem mass spectrometry, has not been shown to be capable of monitoring changes in protein expression levels.

Proteomes are generally quite complex. They contain many thousands of proteins, which can range in relative concentration by five or six orders of magnitude. Unlike genomes, proteomes are dynamic: the proteins making up a cell's proteome change in response to the cell's chemical and physical environment. Post-translational processing is constantly modifying the functional forms of cellular proteins, and this level of protein expression is affected by many different stimuli. Transcriptional profiling (examining mRNA) is of limited use in deciphering such a dynamic system. Therefore, direct qualitative and quantitative analysis of the actual proteins within the proteome is required to achieve a functional understanding of proteins on a cellular scale. The following section details methods currently used to obtain quantitative protein information.

Several biochemical techniques such as staining proteins separated on 2-D gels with non-fluorescent dyes (Coomassie Blue, Fast Green), fluorescent dyes (Sypro Red, Sypro Orange), and colloidal metal stains (silver, gold) are used to quantify relative protein amounts. These staining techniques are limited by poor quantitative precision and accuracy because varying amounts of stain is incorporated into each protein and stained proteins can be difficult to resolve from the background staining of the gel matrix. Other techniques such as introducing radioactive labels or metabolic labeling ($^{14}$C-amino acids, $^{3}$H-lucine, $^{35}$S-methionine) during cellular protein synthesis can overcome some of these problems associated with background noise in the classical staining techniques. Radiolabeling is unfortunately time consuming, expensive, and not practical (or rarely allowed) for human sourced samples, e.g. plasma, tissue, or tumor. Thus, radiolabeling is not a practical option.

To overcome the shortcomings associated with gel-based techniques, other researchers have used various mass spectral based methods. One such method uses MS-isotopic labeling techniques to perform accurate quantitation of the relative quantities of proteins in cells grown under different conditions. In this procedure, stable isotopes such as $^{15}$N are introduced into the cell growth medium. The $^{15}$N-enriched proteins produced during the cell growth process are then compared with unaltered proteins by mixing the two and analyzing them together. The corresponding $^{15}$N labeled peptides are compared with their $^{14}$N companion because they have almost identical physical properties except the predicted mass shift. This strategy makes it possible to record fairly accurately the quantitative differences between native and isotopically enriched "companion" peptides. Y. Oda, et al., *Proc. Natl. Acad. Sci. USA* 96:6591-6596 (1999). However, this strategy has limited utility because it requires treatment with an enriched stable isotope medium prior to protein isolation, for a length of time sufficient for incorporation of the isotopes into the proteome itself.

Another approach that overcomes this shortcoming was presented recently (Gygi, S. P., et al., Quantitative analysis of complex protein mixtures using isotope-coded affinity tags, *Nat. Biotechnol.* 17:994-999 (1999); Griffin, T. J., et al., Quantitative proteomic analysis using a MALDI quadrupole time-of-flight mass spectrometer, *Anal. Chem.,* 73:978-986 (2001)). This approach involves derivatizing protein mixtures with heavy and light isotope-coded affinity tags (ICAT). These tags are covalently bound to specific amino acid residues, and carry a high-affinity moiety such as biotin that serves as means of isolation from untagged material. The proteins are then digested and the tagged peptides are affinity purified for subsequent quantitative analysis. The affinity-purified fractions are subjected to sequence identification using tandem mass spectrometry methods and concurrently analyzed to measure the relative expression levels of individual proteins from complex, control and experimental protein mixtures. Early development of this technology suggested that it was fairly robust and could be widely applicable. Even this method is plagued, however, with the poor yields associated with incomplete tagging and the affinity purification steps. Another problem with this approach is that it is only useful for proteins containing at least one free cysteine group. An example of this pitfall is illustrated by the fact that 35% of the yeast ribosomal proteins are cysteine-free and therefore cannot be identified or quantified using the ICAT technology. Furthermore these tagged peptides must be of a mass amenable to sensitive MS/MS analysis.

The growing importance of genomic, proteomic, and metabolomic information in biotechnology and pharmaceutical research and development has stimulated the development of many innovative technologies. A common goal of many analytical studies in the life sciences is the qualitative identification of chemical components in complex chemical mixtures of biological origin and the quantitative measurement of the relative abundance of chemical components in these mixtures. A more targeted goal is the discovery of chemical species or biomarkers in such mixtures that can be used as an indication of a particular disease. Such studies play a key role in the field of metabolomics and proteomics, but are easily extended to other fields of life science. Frequently these biomarkers provide information about a chemical species or a biological pathway that can serve as either a target for treatment or at least as an indicator of the efficacy of a drug candidate developed to treat a particular disease. These biomarker discovery studies generally involve comparing two populations of complex biological mixtures. One of these sample populations is typically representative of a "control" state (normal, untreated, non-diseased, etc) and the second sample population is typically representative of an "experimental" state (abnormal, treated, diseased, etc). The primary goals of these biomarker discovery experiments are two-fold. First, each component in the two sample populations must be measured quantitatively to determine if their relative expression level has changed in a statistically significant manner between the two sample states. The second goal is to qualitatively identify each component that has shifted in its expression level in a statistically significant manner and, in general, to qualitatively identify as many chemical components in the sample populations as possible. Ideally, analytical methods developed for this application are high in sensitivity and are capable of measuring chemical components in a mixture over a wide dynamic range.

Thus, there exists a need for a relatively rapid and cost-effective analytical method that allows the chemical composition of very complex biological mixtures to be compared in a comprehensive and a quantitative manner and preferably in a comprehensive quantitative and comprehensive qualitative manner.

According to an aspect of the present invention, there is provided a method of mass spectrometry comprising:

providing a first sample comprising a first mixture of molecules of biological origin;

measuring a first physico-chemical property other than mass to charge ratio of first molecules in the first mixture;

mass analysing the first molecules in the first mixture and accurately determining the mass to charge ratio of the first molecules in the first mixture;

providing a second sample comprising a second mixture of molecules of biological origin;

measuring a first physico-chemical property other than mass to charge ratio of first molecules in the second mixture;

mass analysing the first molecules in the second mixture and accurately determining the mass to charge ratio of the first molecules in the second mixture; and determining the intensity of first molecules in the first mixture and the intensity of first molecules in the second mixture, the first molecules in the first mixture and the first molecules in the second mixture having been determined to have substantially the same mass to charge ratio and substantially the same first physico-chemical property.

The first mixture and/or the second mixture may comprise a plurality of different biopolymers, proteins, peptides, polypeptides, oligionucleotides, oligionucleosides, amino acids, carbohydrates, sugars, lipids, fatty acids, vitamins, hormones, portions or fragments of DNA, portions or fragments of cDNA, portions or fragments of RNA, portions or fragments of mRNA, portions or fragments of tRNA, polyclonal antibodies, monoclonal antibodies, ribonucleases, enzymes, metabolites, polysaccharides, phosphorolated peptides, phosphorolated proteins, glycopeptides, glycoproteins or steroids.

The first mixture and/or the second mixture preferably comprise at least 2, 5, 10, 20, 30, 40, 50, 60, 70, 80, 90, 100, 200, 300, 400, 500, 600, 700, 800, 900, 1000, 1500, 2000, 2500, 3000, 3500, 4000, 4500, or 5000 molecules having different identities. Preferably, the first mixture and/or the second mixture comprise a non-equimolar heterogeneous complex mixture.

The mass to charge ratio of the first molecules in the first mixture and/or the mass to charge ratio of the first molecules in the second mixture is preferably determined to within 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm or <1 ppm. Preferably, the mass to charge ratio of the first molecules in the first mixture and/or the mass to charge ratio of the first molecules in the second mixture is determined to within 15-20 ppm, 10-15 ppm, 5-10 ppm or 1-5 ppm. Preferably, the mass to charge ratio of the first molecules in the first mixture and/or the mass to charge ratio of the first molecules in the second mixture is determined to within 0.01 mass units, 0.009 mass units, 0.008 mass units, 0.007 mass units, 0.006 mass units, 0.005 mass units, 0.004 mass units, 0.003 mass units, 0.002 mass units, 0.001 mass units or <0.001 mass units.

Quantitation of the first molecules may involve at least one of the following steps:

(i) comparing the intensity of first molecules in the first mixture with the intensity of second molecules in the first mixture;

(ii) comparing the intensity of first molecules in the first mixture with the intensity of first molecules in the second mixture;

(iii) comparing the intensity of second molecules in the first mixture with the intensity of second molecules in the second mixture;

(iv) comparing the intensity of first molecules in the second mixture with the intensity of second molecules in the second mixture; and (v) comparing the ratio of: (a) the intensity of first molecules in the first mixture to the intensity of first molecules in the second mixture with (b) the intensity of second molecules in the first mixture to the intensity of second molecules in the second mixture.

The second molecules in the first mixture are preferably substantially the same as the second molecules in the second mixture.

The second molecules may be endogenous or exogenous to the first and second mixtures.

Preferably, the method further comprises:

measuring a second physico-chemical property other than mass to charge ratio of the first molecules in the first mixture and the first molecules in the second mixture; and wherein the first molecules in the first mixture and the first molecules in the second mixture are determined to have substantially the same second physico-chemical property.

Preferably, the method further comprises:

measuring a third physico-chemical property other than mass to charge ratio of the first molecules in the first mixture and the first molecules in the second mixture; and wherein the first molecules in the first mixture and the first molecules in the second mixture are determined to have substantially the same third physico-chemical property.

Preferably, the method further comprises:

measuring a fourth physico-chemical property other than mass to charge ratio of the first molecules in the first mixture and the first molecules in the second mixture; and wherein the first molecules in the first mixture and the first molecules in the second mixture are determined to have substantially the same fourth physico-chemical property.

Preferably, the method further comprises:

measuring a fifth or yet further physico-chemical property other than mass to charge ratio of the first molecules in the first mixture and the first molecules in the second mixture; and wherein the first molecules in the first mixture and the first molecules in the second mixture are determined to have substantially the same fifth or yet further physico-chemical property.

The first and/or the second and/or the third and/or the fourth and/or the fifth or yet further physico-chemical properties are preferably selected from the group consisting of: (i) elution time, hydrophobicity, hydrophilicity, migration time, or chromatographic retention time; (ii) solubility; (iii) molecular volume or size; (iv) net charge, charge state, ionic charge or composite observed charge state; (v) isoelectric point (pI); (vi) dissociation constant (pKa); (vii) antibody affinity; (viii) electrophoretic mobility; (ix) ionisation potential; (x) dipole moment; (xi) hydrogen-bonding capability or hydrogen-bonding capacity; and (xii) ion mobility in gas phase.

The mass to charge ratio of the first molecules in the first mixture and/or the mass to charge ratio of the first molecules in the second mixture may be mass analysed by either: (i) a Fourier Transform ("FT") mass spectrometer; (ii) a Fourier Transform Ion Cyclotron Resonance ("FTICR") mass spectrometer; (iii) a Time of Flight ("TOF") mass spectrometer; (iv) an orthogonal acceleration Time of Flight ("oaTOF") mass spectrometer; (v) a magnetic sector mass spectrometer; (vi) a quadrupole mass analyser; (vii) an ion trap mass analyser; and (viii) a Fourier Transform orbitrap, an electrostatic Ion Cyclotron Resonance mass spectrometer or an electrostatic Fourier Transform mass spectrometer.

The first sample may comprise an experimental sample and the second sample may comprise a control sample. For example, the first sample may be taken from a diseased organism and the second sample may be taken from a non-diseased organism. Alternatively, the first sample may be taken from a treated organism and the second sample may be taken from a non-treated organism. A yet further option is that the first sample may be taken from a mutant organism and the second sample may be taken from a wild type organism.

The first molecules in the first mixture and/or the first molecules in the second mixture may be identified.

Embodiments are contemplated wherein 3, 4, 5 or more different samples may be analysed and quantified. Accordingly, the method may further comprise:

providing one or more further samples comprising one or more further mixtures of molecules of biological origin;

measuring a first physico-chemical property other than mass to charge ratio of first molecules in the one or more further mixtures;

mass analysing the first molecules in the one or more further mixtures and accurately determining the mass to charge ratio of the first molecules in the one or more further mixtures; and determining the intensity of first molecules in the one or more further mixtures wherein the first molecules in the first mixture, the first molecules in the second mixture and the first molecules in the one or more further mixtures are determined to have substantially the same mass to charge ratio and substantially the same first physico-chemical property and optionally the same second and/or third and/or fourth and/or fifth or yet further physico-chemical property. The first molecules in the first mixture and/or the first molecules in the second mixture and/or the first molecules in the one or more further mixtures may then be identified.

Identification of the first molecules may in some circumstances only be carried out when there is a differential expression greater than a predetermined threshold. For example, the molecules present in an experimental sample may only be identified if they are present at a higher (or lower) concentration than a control sample. For example, the first molecules in the first mixture and/or the first molecules in the second mixture may only be identified if the intensity of the first molecules in the first mixture differs (positively or negatively) from the intensity of the first molecules in the second mixture by more than a predetermined amount. Alternatively, the first molecules in the first mixture and/or the first molecules in the second mixture may only be identified if the average intensity of a plurality of different molecules in the first mixture differs from the average intensity of a plurality of different molecules in the second mixture by more than a predetermined amount. In both cases the predetermined amount may be selected from the group consisting of: (i) 1%; (ii) 2%; (iii) 5%; (iv) 10%; (v) 20%; (vi) 50%; (vii) 100%; (viii) 150%; (ix) 200%; (x) 250%; (xi) 300%; (xii) 350%; (xiii) 400%; (xiv) 450%; (xv) 500%; (xvi) 1000%; (xvii) 5000%; and (xviii) 10000%.

In an embodiment molecules may be identified by referring to a database. For example, the step of identifying the first molecules in the first mixture and/or the first molecules in the second mixture may comprise comparing the first physico-chemical property and optionally the second and/or third and/or fourth and/or fifth and yet further physico-chemical properties and the determined mass to charge ratio of the first molecules in the first mixture and/or the first molecules in the second mixture with an index of molecules, wherein the index comprises:

(i) the identity of each indexed molecule;

(ii) an experimentally determined or predicted first physico-chemical property of each indexed molecule;

(iii) an experimentally determined or predicted accurate mass or mass to charge ratio(s) of each indexed molecule; and (iv) optionally an experimentally determined or predicted second physico-chemical property of each indexed molecule and/or an experimentally determined or predicted third physico-chemical property of each indexed molecule and/or an experimentally determined or predicted fourth physico-chemical property of each indexed molecule and/or an experimentally determined or predicted fifth or yet further physico-chemical property of each indexed molecule. The first molecules in the first mixture and/or the first molecules in the second mixture may comprise a peptide and the index of molecules may comprise an index of peptides. The index of peptides may be generated by determining how one or more proteins might fragment or be digested so as to result in a plurality of peptides. Alternatively, the first molecules in the first mixture and/or the first molecules in the second mixture may comprise a peptide and the index of molecules comprises an index of proteins.

According to another embodiment, at least some of the data may be calculated. Accordingly, the step of identifying the first molecules in the first mixture and/or the first molecules in the second mixture may comprise calculating the first and/or second and/or third and/or fourth and/or fifth or yet further physico-chemical properties from an index of molecules, the index comprising:

(i) the identity of each indexed molecule; and (ii) an experimentally determined or predicted accurate mass or mass to charge ratio(s) of each indexed molecule.

The index of molecules may comprise: (i) a protein or proteome sequence database; (ii) an Expressed Sequence Tag (EST) database; or (iii) a gene or genome database.

Other embodiments are contemplated wherein a database comprising both accurate mass and other physico-chemical properties is referred to and other physico-chemical properties are calculated from data in the database. For example, the database may comprise a list of molecules and their accurate mass and retention time, and a second physico-chemical property such as dissociation constant (pKa) may be calculated.

The first molecules in the first mixture and/or the first molecules in the second mixture may be identified on the basis of:

(i) the closeness of fit of the determined mass to charge ratio of the first molecules in the first mixture and/or the first molecules in the second mixture with the mass or mass to charge ratio of an indexed molecule; and/or (ii) the closeness of fit of the first physico-chemical property of the first molecules in the first mixture and/or the first molecules in the second mixture with the first physico-chemical property of the indexed molecule; and/or (iii) the closeness of fit of a second physico-chemical property of the first molecules in the first mixture and/or the first molecules in the second mixture with the second physico-chemical property of the indexed molecule; and/or (iv) the closeness of fit of a third physico-chemical property of the first molecules in the first mixture and/or the first molecules in the second mixture with the third physico-chemical property of the indexed molecule; and/or (v) the closeness of fit of a fourth physico-chemical property of the first molecules in the first mixture and/or the first molecules in the second mixture with the fourth physico-chemical property of the indexed molecule; and/or (vi) the closeness of fit of a fifth or yet further physico-chemical property of the first molecules in the first mixture and/or the first molecules in the second mixture with the fifth or yet further physico-chemical property of the indexed molecule.

According to another aspect of the present invention, there is provided a method of mass spectrometry comprising:

providing a mixture of molecules of biological origin;

measuring a first physico-chemical property other than mass to charge ratio of first molecules in the mixture;

mass analysing the first molecules and accurately determining the mass to charge ratio of the first molecules; and identifying the first molecules on the basis of at least the first physico-chemical property and the accurately determined mass to charge ratio of the first molecules.

The mixture of molecules preferably comprises a plurality of different biopolymers, proteins, peptides, polypeptides, oligionucleotides, oligionucleosides, amino acids, carbohydrates, sugars, lipids, fatty acids, vitamins, hormones, portions or fragments of DNA, portions or fragments of cDNA, portions or fragments of RNA, portions or fragments of mRNA, portions or fragments of tRNA, polyclonal antibodies, monoclonal antibodies, ribonucleases, enzymes, metabolites, polysaccharides, phosphorolated peptides, phosphorolated proteins, glycopeptides, glycoproteins or steroids.

The first molecules may also be quantified.

According to another aspect of the present invention there is provided a method of mass spectrometry, comprising:

providing a mixture of peptides;

measuring a first physico-chemical property other than mass to charge ratio of first molecules comprising peptides in the mixture;

accurately determining the mass to charge ratio of the first molecules comprising peptides; and identifying the first molecules comprising peptides on the basis of at least the measured first physico-chemical property and the accurately determined mass to charge ratio of the first molecules comprising peptides.

An internal standard comprising one or more peptides and/or one or more synthetic molecules may be added to the mixture of peptides or a fraction of the mixture of peptides.

According to another aspect of the present invention there is provided a method of mass spectrometry, comprising:

providing a mixture of proteins;

providing a mixture of peptides derived from at least some of the proteins;

measuring a first physico-chemical property other than mass or mass to charge ratio of either at least one protein in the mixture of proteins and/or first molecules comprising peptides in the mixture of peptides;

accurately determining the mass to charge ratio of the first molecules comprising peptides; and identifying the first molecules comprising peptides on the basis of at least the measured first physico-chemical property and the accurately determined mass to charge ratio of the first peptides.

An internal standard comprising one or more proteins and/or one or more synthetic molecules may be added to the mixture of proteins or a fraction of the mixture of proteins.

The mixture of proteins may be pre-fractionated. For example, the method may further comprise fractionating the mixture of proteins, preferably by single-dimensional electrophoresis e.g. 1D gel, multi-dimensional electrophoresis e.g. 2D gel, size exclusion chromatography or by affinity chromatography so as to separate one or more proteins from the mixture of proteins and wherein the one or more proteins separated from the mixture of proteins are then digested or fragmented so as to provide the mixture of peptides.

According to an alternative embodiment the mixture of proteins may be digested without any pre-fractionation of the proteins and hence the method may further comprise digesting or fragmenting the mixture of proteins so as to provide the mixture of peptides.

The peptides may be fractionated prior to mass analysis. The method may further comprise separating a first fraction of one or more peptides from the mixture of peptides. The one or more peptides may be separated from the mixture of peptides by: (i) High Performance Liquid Chromatography ("HPLC"); (ii) anion exchange; (iii) anion exchange chromatography; (iv) cation exchange; (v) cation exchange chromatography; (vi) ion pair reversed-phase chromatography; (vii) chromatography; (vii) single dimensional electrophoresis; (ix) multi-dimensional electrophoresis; (x) size exclusion; (xi) affinity; (xii) reverse phase chromatography; (xiii) Capillary Electrophoresis Chromatography ("CEC"); (xiv) electrophoresis; (xv) ion mobility separation; (xvi) Field Asymmetric Ion Mobility Separation ("FAIMS"); or (xvi) capillary electrophoresis. Preferably, the one or more peptides in the first fraction have substantially the same first physico-chemical property, preferably the same elution time, hydrophobicity, hydrophilicity, migration time, or chromatographic retention time. Chromatographic methods may therefore be used to separate one or more peptides from a pool of peptides on the basis of e.g. elution time, hydrophobicity, hydrophilicity, migration time, or chromatographic retention time.

The peptides may also be quantified.

According to a particularly preferred embodiment, a protein or a Post Translationally Modified ("PTM") protein which correlates with one or more identified peptides may be identified. The protein or the Post Translationally Modified protein may also itself by quantified.

Various refinements to the identification process are contemplated. One refinement comprises checking that the intensities of all peptides which are considered to correlate with the protein or the Post Translationally Modified protein fall within one or more predetermined ranges (i.e. checking that the intensities are consistent).

In addition to proteins and peptides, the present invention is particularly suitable for the analysis of metabolites. According to another aspect of the present invention there is provided a method of mass spectrometry, comprising:

providing a mixture of metabolites;

measuring a first physico-chemical property other than mass to charge ratio of first molecules comprising metabolites in the mixture;

accurately determining the mass to charge ratio of the first molecules comprising metabolites; and identifying the first molecules comprising metabolites on the basis of at least the measured first physico-chemical property and the accurately determined mass to charge ratio of the first molecules comprising metabolites.

At least some of the metabolites in the mixture may be extracted from blood plasma and/or urine and/or faeces and/or sweat and/or breath.

According to another aspect of the present invention there is provided a method of mass spectrometry, comprising:

providing a mixture comprising: (i) a plurality of portions or fragments of DNA; (ii) a plurality of portions or fragments of RNA; (iii) a plurality of oligionucleotides and/or a plurality of oligionucleosides; (iv) a plurality of nucleic acids; (v) a plurality of portions or fragments of genes; (vi) a plurality of ribonucleases (RNases); (vii) a plurality of portions or fragments of cDNA; (viii) a plurality of portions or fragments of mRNA; or (ix) a plurality of portions or fragments of tRNA;

measuring a first physico-chemical property other than mass to charge ratio of first molecules in the mixture;

accurately determining the mass to charge ratio of the first molecules; and identifying the first molecules on the basis of at least the measured first physico-chemical property and the accurately determined mass to charge ratio of the first molecules.

According to another aspect of the present invention there is provided a method of mass spectrometry, comprising:

providing a mixture selected from the group comprising: (i) phosphorolated peptides; (ii) phosphorolated proteins; (iii) glycopeptides; (iv) glycoproteins; (v) carbohydrates; (vi) sugars; (vii) lipids; (viii) fatty acids; (ix) vitamins; (x) hormones; (xi) steroids; (xii) monoclonal or polyclonal antibodies; and (xiii) polysaccharides;

measuring a first physico-chemical property other than mass to charge ratio of first molecules in the mixture;

accurately determining the mass to charge ratio of the first molecules; and identifying the first molecules on the basis of at least the measured first physico-chemical property and the accurately determined mass to charge ratio of the first molecules.

The mixture preferably comprises at least 2, 5, 10, 20, 30, 40, 50, 60, 70, 80, 90, 100, 200, 300, 400, 500, 600, 700, 800, 900, 1000, 1500, 2000, 2500, 3000, 3500, 4000, 4500, or 5000 molecules having different identities. The preferred embodiment is particularly suitable for use with non-equimolar heterogeneous complex mixtures.

The step of accurately determining the mass to charge ratio of the first molecules preferably comprises determining the mass to charge ratio of the first molecules to within 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm or <1 ppm. Preferably, step of accurately determining the mass to charge ratio of the first molecules comprises determining the mass to charge ratio of the first molecules to within 15-20 ppm, 10-15 ppm, 5-10 ppm or 1-5 ppm. Preferably, the step of accurately determining the mass to charge ratio of the first molecules comprises determining the mass to charge ratio of the first molecules to within 0.01 mass units, 0.009 mass units, 0.008 mass units, 0.007 mass units, 0.006 mass units, 0.005 mass units, 0.004 mass units, 0.003 mass units, 0.002 mass units, 0.001 mass units or <0.001 mass units.

First molecules may separated from other molecules in the mixture by virtue of the first physico-chemical property e.g. elution/retention time.

The first molecules may be temporally and/or spatially separated from other molecules in the mixture.

Preferably, the first molecules are separated from other molecules in the mixture by: (i) High Performance Liquid Chromatography ("HPLC"); (ii) anion exchange; (iii) anion exchange chromatography; (iv) cation exchange; (v) cation exchange chromatography; (vi) ion pair reversed-phase chromatography; (vii) chromatography; (vii) single dimensional electrophoresis; (ix) multi-dimensional electrophoresis; (x) size exclusion; (xi) affinity; (xii) revere phase chromatography; (xiii) Capillary Electrophoresis Chromatography ("CEC"); (xiv) electrophoresis; (xv) ion mobility separation; (xvi) Field Asymmetric Ion Mobility Separation ("FAIMS"); or (xvi) capillary electrophoresis.

Embodiments are also contemplated wherein the first physico-chemical property (e.g. net charge, charge state, ionic charge or composite observed charge state) is determined from a mass spectrum of molecules in the mixture.

The method may further comprise:

measuring a second physico-chemical property other than mass to charge ratio of the first molecules in the mixture, the second physico-chemical property being different from the first physico-chemical property; and wherein the step of identifying the first molecules further comprises identifying the first molecules on the basis of at least the first and second physico-chemical properties and the determined mass to charge ratio of the first molecules.

The method may further comprise:

measuring a third physico-chemical property other than mass to charge ratio of the first molecules in the mixture, the third physico-chemical property being different from the first and second physico-chemical properties; and wherein the step of identifying the first molecules further comprises identifying the first molecules on the basis of at least the first, second and third physico-chemical properties and the determined mass to charge ratio of the first molecules.

The method may further comprise:

measuring a fourth physico-chemical property other than mass to charge ratio of the first molecules in the mixture, the fourth physico-chemical property being different from the first, second and third physico-chemical properties; and wherein the step of identifying the first molecules further comprises identifying the first molecules on the basis of at least the first, second, third and fourth physico-chemical properties and the determined mass to charge ratio of the first molecules.

The method may further comprise:

measuring a fifth or yet further physico-chemical property other than mass to charge ratio of the first molecules in the mixture, the fifth or yet further physico-chemical property being different from the first, second, third and fourth physico-chemical properties; and wherein the step of identifying the first molecules further comprises identifying the first molecules on the basis of at least the first, second, third, fourth, fifth or yet further physico-chemical properties and the determined mass to charge ratio of the first molecules.

The first and/or second and/or third and/or fourth and/or fifth or yet further physico-chemical property may be selected from the group consisting of: (i) elution time, hydrophobicity, hydrophilicity, migration time, or chromatographic retention time; (ii) solubility; (iii) molecular volume or size; (iv) net charge, charge state, ionic charge or composite observed charge state; (v) isoelectric point (pI); (vi) dissociation constant (pKa); (vii) antibody affinity; (viii) electrophoretic mobility; (ix) ionisation potential; (x) dipole moment; (xi) hydrogen-bonding capability or hydrogen-bonding capacity; and (xii) ion mobility in gas phase.

One or more endogenous and/or one or more exogenous molecules may be used as an internal standard. The internal standard may be used to calibrate at least the first physico-chemical property and optionally the second and/or third and/or fourth and/or firth or yet further physico-chemical property.

The step of identifying the first molecules may comprise comparing the first physico-chemical property and optionally the second and/or third and/or fourth and/or fifth or yet further physico-chemical properties and the determined mass to charge ratio of the first molecules with an index of molecules, wherein the index comprises:

(i) the identity of each indexed molecule;

(ii) an experimentally determined or predicted first physico-chemical property of each indexed molecule; and (iii) an experimentally determined or predicted accurate mass or mass to charge ratio(s) of each indexed molecule.

The first molecules comprise a peptide and the index of molecules comprises an index of peptides.

The index of peptides may be generated by determining how one or more proteins might fragment or be digested so as to result in a plurality of peptides.

The first molecules may comprise a peptide and the index of molecules may comprises an index of proteins.

Preferably, the first molecules are identified on the basis of:

(i) the closeness of fit of the determined mass to charge ratio of the first molecules with the mass or mass to charge ratio of an indexed molecule; and/or (ii) the closeness of fit of the first physico-chemical property of the first molecules with the first physico-property of the indexed molecule; and/or (iii) the closeness of fit of a second physico-chemical property of the first molecules with the second physico-property of the indexed molecule; and/or (iv) the closeness of fit of a third physico-chemical property of the first molecules with the third physico-property of the indexed molecule; and/or (v) the closeness of fit of a fourth physico-chemical property of the first molecules with the fourth physico-property of the indexed molecule; and/or (vi) the closeness of fit of a fifth or yet further physico-chemical property of the first molecules with fifth or yet further physico-property of the indexed molecule.

Preferably, the step of identifying the first molecules comprises calculating the first and/or second and/or third and/or fourth and/or fifth or yet further physico-chemical properties from an index of molecules, the index comprising:

(i) the identity of each indexed molecule; and (ii) an experimentally determined or predicted accurate mass or mass to charge ratio(s) of each indexed molecule.

The index may comprise a protein or proteome sequence database, an Expressed Sequence Tag (EST) database or a gene or genome database.

According to another aspect of the present invention there is provided a method of generating an index for use in identifying molecules of biological origin by mass spectrometry comprising:

accurately determining the masses or mass to charge ratios of molecules of biological origin;

determining a first physico-chemical property other than mass or mass to charge ratio of the molecules of biological origin; and optionally determining a second and/or third and/or fourth and/or fifth or yet further physico-chemical property of the molecules of biological origin.

According to another aspect of the present invention there is provided a method of generating an index for use in identifying molecules of biological origin by mass spectrometry comprising:

accurately determining the masses or mass to charge ratios of molecules comprising peptides resulting from the digestion or fragmentation of a polypeptide or protein;

determining a first physico-chemical property other than mass or mass to charge ratio of the molecules comprising peptides; and optionally determining a second and/or third and/or fourth and/or fifth or yet further physico-chemical property of the molecules comprising peptides.

According to another aspect of the present invention there is provided a method of generating an index for use in iden tifying molecules of biological origin by mass spectrometry comprising:

accurately determining the masses or mass to charge ratios of molecules comprising peptides resulting from the digestion or fragmentation of a polypeptide or protein;

determining a first physico-chemical property other than mass or mass to charge ratio of one or more proteins from which the peptides are derived; and optionally determining a second and/or third and/or fourth and/or fifth or yet further physico-chemical property of the proteins.

Preferably, the mass to charge ratio of the molecules is determined to within 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm or <1 ppm. Preferably, the mass to charge ratio of the molecules is determined to within 15-20 ppm, 10-15 ppm, 5-10 ppm or 1-5 ppm. Preferably, the mass to charge ratio of the molecules is determined to within 0.01 mass units, 0.009 mass units, 0.008 mass units, 0.007 mass units, 0.006 mass units, 0.005 mass units, 0.004 mass units, 0.003 mass units, 0.002 mass units, 0.001 mass units or <0.001 mass units.

The first and/or second and/or third and/or fourth and/or fifth or yet further physico-chemical property may be selected from the group consisting of: (i) elution time, hydrophobicity, hydrophilicity, migration time, or chromatographic retention time; (ii) solubility; (iii) molecular volume or size; (iv) net charge, charge state, ionic charge or composite observed charge state; (v) isoelectric point (pI); (vi) dissociation constant (pKa); (vii) antibody affinity; (viii) electrophoretic mobility; (ix) ionisation potential; (x) dipole moment; (xi) hydrogen-bonding capability or hydrogen-bonding capacity; and (xii) ion mobility in gas phase.

A relatively low priority may be assigned to molecules having masses or mass to charge ratios below a lower threshold. Indeed such molecules may effectively be ignored. The lower threshold may be in the range <500, 500-1000, 1000-1500, 1500-2000, 2000-2500, 2500-3000 or 3000-3500 daltons. The lower threshold may for example correspond with the masses or mass to charge ratios of peptides having less than 6, 7, 8, 9, 10, 11 or 12 amino acids. A relatively low priority may also be assigned to molecules having masses or mass to charge ratios above an upper threshold. The upper threshold may be in the range 5000-5500, 5500-6000, 6000-6500, 6500-7000, 7000-7500, 7500-8000, 8000-8500, 8500-9000, 9000-9500, 9500-10000, 10000-10500, 10500-11000, 11000-11500, 11500-12000, 12000-12500, 12500-13000, 13000-13500, 13500-14000, 14000-14500, 14500-15000, 15000-15500, 15500-16000, 16000-16500 and >16500 daltons.

The first and/or second and/or third and/or fourth and/or fifth and yet further physico-chemical properties may be calculated.

According to another aspect of the present invention there is provided a mass spectrometer comprising:

a mass analyser for accurately determining the mass to charge ratio of the first molecules;

wherein in use at least a first physico-chemical property other than mass to charge ratio of the first molecules is measured and optionally a second and/or third and/or fourth and/or fifth or yet further physico-chemical property is measured;

and wherein the mass spectrometer further comprises means for identifying the first molecules on the basis of at least the first physico-chemical property and the accurately determined mass to charge ratio of the first molecules and optionally on the basis of the second and/or third and/or fourth and/or fifth or yet further physico-chemical property.

The first and/or second and/or third and/or fourth and/or fifth or yet further physico-chemical properties may be measured using: (i) a liquid chromatography or High Performance Liquid Chromatography ("HPLC") column; (ii) a reverse phase High Performance Liquid Chromatography column; (iii) an ultra High Pressure Liquid Chromatography column; (iv) a size exclusion chromatography column; (v) an affinity chromatography column; (vi) a Capillary Electrophoresis ("CE") column; (vii) an ion chromatography column; (viii) a single dimensional or multi-dimensional electrophoresis device; or (ix) a drift tube comprising a gas.

The first and/or second and/or third and/or fourth and/or fifth or yet further physico-chemical properties may additionally/alternatively be measured from a mass spectrum of the first molecules. For example, net charge, charge state, ionic charge or composite observed charge state may be measured or determined from a mass spectrum by virtue of the mass to charge ratio separation of peaks in the mass spectrum.

The first and/or second and/or third and/or fourth and/or fifth or yet further physico-chemical property may be selected from the group consisting of: (i) elution time, hydrophobicity, hydrophilicity, migration time, or chromatographic retention time; (ii) solubility; (iii) molecular volume or size; (iv) net charge, charge state, ionic charge or composite observed charge state; (v) isoelectric point (pI); (vi) dissociation constant (pKa); (vii) antibody affinity; (viii) electrophoretic mobility; (ix) ionisation potential; (x) dipole moment; (xi) hydrogen-bonding capability or hydrogen-bonding capacity; and (xii) ion mobility in gas phase.

The mass to charge ratio of the first molecules is preferably determined to within 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm or <1 ppm. Preferably, the mass to charge ratio of the first molecules is determined to within 15-20 ppm, 10-15 ppm, 5-10 ppm or 1-5 ppm. Preferably, the mass to charge ratio of the first molecules is determined to within 0.01 mass units, 0.009 mass units, 0.008 mass units, 0.007 mass units, 0.006 mass units, 0.005 mass units, 0.004 mass units, 0.003 mass units, 0.002 mass units, 0.001 mass units or <0.001 mass units.

The mass spectrometer may comprise a Fourier Transform ("FT") mass spectrometer, a Fourier Transform Ion Cyclotron Resonance ("FTICR") mass spectrometer, a Time of Flight ("TOF") mass spectrometer, an orthogonal acceleration Time of Flight ("oaTOF") mass spectrometer, a magnetic sector mass spectrometer, a quadrupole mass analyser, an ion trap mass analyser or a Fourier Transform orbitrap, electrostatic Ion Cyclotron Resonance mass spectrometer or electrostatic Fourier Transform mass spectrometer.

The mass spectrometer preferably further comprises an ion source for generating mainly molecular or pseudo-molecular ions. The ion source may comprise an atmospheric pressure ionization source e.g. an Electrospray ionisation ("ESI") ion source, an Atmospheric Pressure Chemical Ionisation ("APCI") ion source, an Atmospheric Pressure Photo Ionisation ("APPI") ion source or an atmospheric pressure Matrix Assisted Laser Desorption Ionisation ("MALDI") ion source. Alternatively, the ion source may comprise a non-atmospheric pressure ionization source e.g. a Fast Atom Bombardment ("FAB") ion source, a Liquid Secondary Ions Mass Spectrometry ("LSIMS") ion source, a Matrix Assisted Laser Desorption Ionisation ("MALDI") ion source, a Matrix Assisted Laser Desorption ("MALDI") ion source in combination with a collision cell for collisionally cooling ions or a Laser Desorption Ionisation ("LDI") ion source.

According to another aspect of the present invention there is provided a mass spectrometer comprising:

identification means for identifying first molecules analysed by the mass spectrometer, wherein the identification means refers, in use, to an index of molecules, the index comprising:

(i) the identity of each indexed molecule;

(ii) an experimentally determined or predicted first physico-chemical property of each indexed molecule;

(iii) an experimentally determined or predicted accurate mass or mass to charge ratio(s) of each indexed molecule; and (iv) optionally an experimentally determined or predicted second and/or third and/or fourth and/or fifth or yet further physico-chemical property of each indexed molecule.

Preferably, the index is at least partially stored or generated within the mass spectrometer and/or wherein the index is at least partially stored or generated remotely, preferably on the internet.

According to another aspect of the present invention there is provided a mass spectrometer comprising:

identification means for identifying first molecules analysed by the mass spectrometer, wherein the identification means refers, in use, to an index of molecules, the index comprising:

(i) the identity of each indexed molecule; and (ii) an experimentally determined or predicted accurate mass or mass to charge ratio(s) of each indexed molecule;

and wherein the identification means further determines a first physico-chemical property other than mass or mass to charge ratio of the molecules in the index and optionally determines a second and/or third and/or fourth and/or fifth or yet further physico-chemical property of the molecules in the index.

Preferably, the index comprises: (i) a protein or proteome sequence database; (ii) an Expressed Sequence Tag (EST) database; or (iii) a gene or genome database.

According to another aspect of the present invention there is provided method of mass spectrometry, comprising:

providing a mixture of proteins;

providing a mixture of peptides derived from at least some of the proteins;

measuring a first physico-chemical property other than mass or mass to charge ratio of either at least one protein in the mixture of proteins and/or first molecules comprising peptides in the mixture of peptides;

optionally measuring a second and/or third and/or fourth and/or fifth or yet further physico-chemical property other than mass or mass to charge ratio of either the at least one protein in the mixture of proteins and/or the first molecules comprising peptides in the mixture of peptides;

accurately determining the mass to charge ratio of the first molecules comprising peptides; and identifying the first molecules comprising peptides on the basis of at least the measured first physico-chemical property other than mass or mass to charge ratio of either at least one protein in the mixture of proteins and/or first molecules comprising peptides in the mixture of peptides and the accurately determined mass to charge ratio of the first peptides and optionally also on the basis of the second and/or third and/or fourth and/or fifth or yet further physico-chemical properties.

The preferred embodiment provides an analytical method that identifies and/or quantitates the biopolymers present in a mixture. The biopolymers may be proteins. The mixture under study may be fractionated by one or more separation steps while recording the retention times of each component. Where the biopolymers are proteins, each fraction may then subjected to enzymatic digestion of to obtain mixtures of peptides. These peptide pools may then fractionated by one or more separation steps while recording the retention times of each component. Each fraction may then subjected to mass spectrometry to determine the masses and areas of the peptides. Throughout these processing steps a variety of internal standards and calibrants may be introduced into the samples in order to monitor the performance and reproducibility of the processes.

An appropriate database may be computationally constructed for the samples under investigation. This database may comprise a collection of sequences of proteins hypothesized to be present in the samples under study and may include known and/or hypothesized post-translational modifications. The database may then be expanded by predicting, (a) the retention times of proteins based on experimental parameters used; (b) the peptides generated by enzymatic digestion on experimental parameters used; (c) the retention times of peptides based on experimental parameters used; and (d) the masses of the peptides.

The experimental data is compared with the computationally generated database. Each data point is assigned a peptide based on the statistical significance of the correlation thereby identifying the proteins in the mixture(s). Furthermore, the areas of the assigned peptides are compared between protein mixtures to determine the relative change of peptides and/or post-translationally modified peptides. Finally, the quantitative information gained from this analysis may be used to validate the protein assignments.

Mass spectrometry is used for characterization of the accurate mass of a plurality of biological molecules in a mixture, particularly wherein one or more of the biological molecules is characterized, such that one or more of the mixture's components may be identified and/or quantitated.

A method is provided for determining which members of a set of candidate biopolymers are present in a mixture of sample biopolymers. The method comprises the steps of:

(a) optionally subjecting the mixture of sample biopolymers to one or more fractionation steps, so as to obtain a plurality of sample biopolymer fractions;

(b) selectively digesting a plurality of the sample biopolymers, to obtain a digest comprising a mixture of sample fragments;

(c) subjecting the digest to one or more fractionation steps, so as to obtain a plurality of sample fragment fractions;

(d) determining the accurate masses of individual sample fragments present in one or more fractions;

(e) attributing one or more physicochemical properties to the individual sample fragments, based upon the particular sample fragment fraction each individual sample fragment was fractionated into;

(f) optionally attributing one or more physicochemical properties to the sample biopolymers from which the sample fragments were derived, based upon the particular sample biopolymer fraction the sample biopolymers were fractionated into; and (g) identifying individual sample fragments by comparing the accurate mass and attributed physicochemical properties of the sample fragments with the accurate masses and physicochemical properties of candidate fragments derived from a set of candidate biopolymers that are known to have some probability of being present in the sample.

Optionally, the attributed physicochemical properties of the sample biopolymers from which the sample fragments were derived are compared to the physicochemical properties of the candidate biopolymers, and a candidate biopolymer is identified as being present in the sample on the basis of the identification in step (g) of one or more fragments thereof in the sample fragment mixture.

Preferably, the accurate masses and physicochemical properties of candidate fragments are stored in a calculated fragment map, which is derived from a set of candidate biopolymers that are known to have some probability of being present in the sample.

In one embodiment, the method includes generating a sample fragment map which correlates the accurate mass of individual sample fragments with the attributed physicochemical properties of the individual sample fragments. The identification of individual sample fragments is done by comparing the sample fragment map to the calculated fragment map.

Optionally, a known amount of one or more reference biopolymers is added at any time prior to determining the accurate masses of the individual sample fragments. Preferably, the reference biopolymers are added prior to selectively digesting the plurality of sample biopolymers. Preferably, the physicochemical properties of the reference biopolymers are known, and are used to validate the physicochemical properties attributed to the particular sample biopolymer fractions that the sample biopolymers were fractionated into.

In another embodiment, the relative amounts of individual sample fragments and reference biopolymer fragments are determined.

Preferably, one or more reference biopolymers are added to a plurality of sample biopolymer mixtures, sample biopolymer fractions, digests, or sample fragment fractions.

In the above-described methods, the accurate masses are preferably determined by mass spectrometry. Preferably, the methods are carried out without obtaining secondary MS/MS mass spectra of the measured fragment ions.

Among the physicochemical properties employed according to the preferred embodiments are pI, chromatographic retention time, electrophoretic mobility, ionic charge, ionization potential, hydrophilicity, hydrophobicity, dipole moment, size, hydrogen-bonding capability, and antibody affinity.

Preferably at least one fractionation step employed in the methods of the preferred embodiment is reverse-phase chromatography.

The methods of the preferred embodiment are particularly suitable where the biopolymer is a protein. The methods are preferably applied to mixtures comprising at least 100, 1000 or 5,000 or more proteins.

The preferred embodiment provides an analytical method for identifying and quantitating the proteins present in a complex mixture of proteins. In this embodiment, the method comprises the steps of:

subjecting a mixture of proteins to one or more separation steps while recording the associated retention and/or migration times;

selectively digesting the proteins present in the resulting fractions to obtain mixtures of protein fragments;

subjecting the resulting mixtures to one or more separation steps while recording the associated retention and/or migration times;

accurately measuring the masses of individual protein fragments in the resulting fractions by mass spectrometry; and identifying individual protein fragments by comparing the measured masses and retention and/or migration times of the protein fragments with calculated values.

In a preferred embodiment, the method includes a determination of the relative amounts of individual protein fragments, based on the mass spectral response. In another embodiment, the relative amounts of individual protein are used to help identify the proteins.

In the above-described embodiments, retention and or migration times are preferably obtained from appropriate modes of high performance chromatography, electrophoresis, and ion mobility mass spectrometry.

According to an embodiment amino acid modifications and the relative amounts thereof may be identified and measured. An embodiment will be described below in further detail with respect to the analysis of protein mixtures. With modifications known to be appropriate to the particular biopolymer under study, the methods of the preferred embodiment may also be applied to RNA, DNA and polysaccharides.

A method for the identification and quantitation of biopolymers in mixtures is disclosed. The biopolymer may be a protein or peptide, a nucleic acid, or a polysaccharide, preferably a protein or peptide or nucleic acid, and most preferably a protein or peptide. The method is capable of identifying and quantitating one or more biomolecules from very complex mixtures, for example nucleic acids present in a genome and proteins present in a proteome.

According to an embodiment there is provided the selective cleavage of the macromolecules with reagents that cleave only at selected sites of the macromolecule, for example cleavage of nucleic acids by restriction enzymes, cleavage of proteins by selective peptidases, and cleavage of polysaccharides by glycosidases. Among the peptidases that may be employed are trypsin, endoprotease-LysC, endoprotease-ArgC, endoprotease GluC, and chymotrypsin. The selective cleavage is preferably followed by separation of the resulting fragments on the basis of at least a first physico-chemical property, and optionally further separation on the basis of a second, third or further physico-chemical properties. The mass of the fragments are then measured with high precision, and by comparison of the results to a database of expected fragments which contains information about their exact mass and physico-chemical properties, the method arrives at the identity of the fragments. From the identity and quantity of the fragments, the identity and original quantity of the biopolymer can be determined.

In the case of proteins, the method combines the exact mass of peptide fragments with one or more physico-chemical properties of the peptide fragments, to identify the fragments and assign them to known proteins. This method is used to create detailed ion maps of proteins in the proteome. These ion maps will simultaneously yield accurate identification of and quantitative information regarding proteins in the proteome.

The mass of enzymatically or chemically derived peptides is preferably measured or determined to an accuracy of about 10 ppm, most preferably to an accuracy of about 5 ppm, and particularly preferred to an accuracy of about 1 to about 5 ppm, or less.

Included in the ion maps is information regarding one or more physico-chemical properties of these enzymatically or chemically derived peptides defined within the experimental parameters. This physico-chemical information may include, but is not limited to, the accurate mass, hydrophobicity/hydrophilicity, and net charge. In addition, the proteins in the sample mixture(s) may be pre-fractionated or fractionated by any of a number of different methods including through the use of column matrices, such as but not limited to size exclusion, cation exchange, anion exchange, heparin, sepharose. This fractionation may occur prior to and/or following enzymatic or chemical digestion of the protein mixture. The fractionation may be utilized to generate one or more sub-fractions, with a thereby assigned character, which can then be digested and/or further fractionated. This fractionation and separation process will provide additional information to be added to the ion map and inputted into an identification and quantitation algorithm thereby further increasing the stringency of search.

The optional incorporation of an internal standard provides a means for quantitating the abundance of a protein or peptide, thereby accomplishing absolute quantitation of a protein or peptide in a sample. Relative quantitation of protein abundances in complex mixtures is accomplished by comparing ion maps generated in different conditions (e.g. diseased vs. non-diseased, treated vs. non-treated).

Thus, an overall method for identifying and quantitating the proteins and/or peptides in a mixture, particularly a complex mixture is provided, whereby a series of experimentally derived highly accurate molecular masses is correlated and compared with a database consisting of theoretical molecular masses. In addition to molecular mass, one or more physico-chemical properties or characteristics of the proteins and/or peptides is utilized in correlation and verification of the mixture proteins/peptides with a database or protein data set.

Proteins in a sample mixture being analyzed may be separated by single or multi-dimensional electrophoresis and/or chromatography, e.g. size exclusion, anion exchange, cation exchange, affinity or any combination thereof with each resulting subset being subject to enzymatic or chemical treatment with the specific intent of generating sub-sequences of peptides from such. The resulting peptides generated from each subset may then be subjected to mass spectrometric analysis, with the separation apparatus preferably directly or indirectly coupled to a mass spectrometer. More specifically, with respect to electrospray ionization mass spectrometry, the elution path of the separation/concentration apparatus can be directly coupled to the ionization source of the mass spectrometer. With respect to nano-electrospray ionization mass spectrometry, the eluent from the separation/concentration apparatus can be directly deposited into the nano-electrospray emitter or into any connection in fluid registration therewith. With respect to MALDI mass spectrometry, the eluent from the separation/concentration apparatus is directly deposited in timed fractions, or fractions selected by peak detection by such methods as UV or fluorescence, onto the MALDI targets. In all instances, the ultimate outcome will be generation of a plurality of experimentally derived mass-charge values whose elution/detection time is based on the constraints for elution dictated by the previous separation/concentration apparatus used prior to peptide ionization. A peak picking algorithm reconstructs a calculated molecular mass map of each subset of enzymatically or chemically treated protein or protein pool, included in which is a listing of all pertinent information relating to the creation of the subset. More specifically included will be the molecular weight range of the intact protein(s), the intact protein(s) net charge, and the intact protein(s) affinity to name only a few. Also included may be properties including but not limited to the net charge, hydrophobicity, hydrophilicity, and electrophoretic mobility of each separated sub-sequence from the enzymatically or chemically treated peptide pools prior to ionization.

Further, a control or controls of known concentration may optionally be included and placed directly into the selected separation buffers prior to peptide ionization or directly into the pre-separated/concentrated peptide subsets. Preferably, the control will be approximately equimolar and of a type that will not interact with the separation/concentration support matrix. The addition of the control(s) in a known concentration will facilitate quantitation of the identified proteins.

Identifications may be made using any of a number of different non-redundant protein or nucleotide sequence databases, such as for example, Genbank, SWISS-PROT, EMBLE, TREMBLE, Pdb, Genseq, etc. These databases may be used to predict highly accurate molecular mass maps of any of a number of different enzymatically or chemically digested proteins for comparison with the experimentally derived data. In one embodiment, proteins having a statistically relevant number of peptides whose calculated molecular masses are substantially equal to that of the method's prediction are identified as candidate proteins. For each candidate protein, a plurality of peptide molecular masses are identified based on their accuracy to the method's prediction resulting in a ranked predicted protein list. The peptides identified in the ranked protein list are then cross correlated by their closeness of fit to the characterized physico-chemical properties, including for instance hydrophilicity/hydrophobicity, basicity/acidity values of the peptide. In one embodiment, a multi-step reiterative process of analysis is provided, wherein mass accuracy is assessed as a first analysis, followed by assessment of correlation by various determined physico-chemical properties, including hydrophilicity, net charge, and protein net charge or size depending on how the sample mixture was fractionated or characterized.

By characterization of mixtures under different conditions or from different sources, the method of the invention provides a means for determining protein concentrations, up and/or down regulation, complex formation, post-translational modification, and processing of proteins, from non-equimolar heterogeneous complex protein mixtures. The skilled artisan may then utilize the resulting information to determine and/or identify therapeutically or diagnostically relevant targets for study, screening, or intervention.

The preferred embodiment provides a means for quantitatively comparing the relative level of chemical components contained in two or more complex chemical mixtures such as those which may be encountered in the field of metabolomics or proteomics or other life science comparative experiments. In at least one embodiment, the method of the invention provides information that may be used to qualitatively identify one or more chemical components in each chemical mixture.

An embodiment includes the steps of measuring two or more physico-chemical properties of each chemical component in a mixture with one of these properties being its accurate mass as determined by mass spectrometry. Other physico-chemical properties include, for example, order of elution in one or more specifically defined chromatographic separations, net charge, pI, pKa, and antibody affinity. The accurate mass and physico-chemical property collection of information measured for each component provides a distinguishing signature for each component in each mixture. Finally, the method of the invention includes the step of measuring the mass spectrometric signal intensity or chromatographic peak area of each chemical component in each mixture. Preferably this intensity or peak area measurement is based on accurate mass.

As previously mentioned, a highly desirable task in comparative life science experiments is to determine whether any chemical components in two or more mixtures of samples of biological origin have changed in their level of abundance relative to other chemical components common to each mixture. The method of the invention allows chemical components common to each sample mixture to be matched based on their physico-chemical property distinguishing signatures.

It is not necessary for the chemical identity of each component to be known for a match to be accomplished. It is only necessary that the accurate mass and physico-chemical property signature of each chemical component allows it to be uniquely distinguished from other chemical components in the mixture. The determination of the relative abundance of each matched chemical component is made by first determining the abundance of that chemical component relative to the abundance of a second endogenous chemical component common to both mixtures that has been determined to be unchanged in a statistically significant manner in its relative abundance level in the two sample states being compared. An endogenous chemical component with these properties serves as an internal standard. The ratio of each matched chemical component in each mixture relative to the same endogenous internal standard in each mixture is then compared to provide the relative abundance level difference of each matched chemical component in each mixture. In some instances the addition of exogenous chemical species to each chemical mixture as internal standards may facilitate estimates of recovery, enzymatic digestion efficiency when applicable, accurate mass measurement and chromatographic elution time correction.

In some life science experiments, the chemical components in a sample mixture are known to be constrained to a well characterized list of chemical components. For example, in a proteomics experiment, the proteins being studied may be known to emanate from a particular organism or a well characterized fraction or subset of the proteome of a particular organism. The proteins which could be contained in such a sample or sample sub-fraction in many cases are substantially known. Accordingly the polypeptides produced when such a protein mixture is enzymatically digested using a selective peptidase may be predicted and the accurate mass and many of the physico-chemical properties of each of these polypeptides may be calculated. A preferred method allows the empirically measured accurate mass and physico-chemical properties of each unknown polypeptide in a mixture to be compared to the calculated accurate mass and physico-chemical properties of each polypeptide that could be theoretically contained in the mixture. The chemical identity of a polypeptide in the unknown mixture may be ascertained by its closeness of fit to the accurate mass and physico-chemical properties of a polypeptide that could theoretically be contained in the mixture. Generally, a polypeptide is unique to a particular protein. Therefore, the identification of a particular polypeptide also generally provides a unique identification of the protein parent to that polypeptide. The identification of a protein is further confirmed when more than one polypeptide is identified that is unique to that protein.

In the study of proteins, another embodiment of the invention allows the detection of post translationally modified forms of the constrained group of proteins or a subset thereof that could be theoretically contained in the mixture being studied. This method also provides for the detection of modified forms of the constrained group of proteins that could theoretically be contained in the mixture or a subset thereof which arise from one or more amino acid substitutions. This embodiment examines the entire measured polypeptide accurate mass and physico-chemical property data set for additional polypeptides which differ in mass by an exact amount which corresponds to the difference in mass of a post translational modification or an amino acid substitution of a polypeptide that theoretically could emanate each of the proteins in the constrained group of proteins or a subset thereof that could theoretically be contained in the unknown mixture being studied. The identity of each of these candidate post-translationally modified and amino acid substitution forms of this initial protein data set may be further confirmed by its conformance with other calculated physical chemical properties. For example, a phosphorylated form of a polypeptide would not only exhibit an exact mass difference conforming to the addition of a phosphorylation group, but it would only be likely to occur in mammalian systems if the non-phosphorylated form of the polypeptide contained one of the amino acids: serine, tyrosine, or threonine. In bacterial systems this list of amino acids could be extended to include histidine. Finally, the phosphorylated form of the polypeptide would be expected to be more hydrophilic than the non-phosphorylated form and it would therefore be expected to exhibit a slightly shorter elution time in a reverse phase chromatography separation.

The method of the preferred embodiment is appropriate for the analysis of mixtures where different chemical components of the mixture are first separated or partially separated by one or more dimensions of well defined chromatography that causes components to elute sequentially and in a reproducible manner.

A variety of mass spectrometry systems can be employed in the methods of the invention. Ideally, mass spectrometers capable of high mass accuracy, high sensitivity and high resolution are employed. The mass analyzers of such mass spectrometers include, but are not limited to, quadrupole, Time of Flight, ion trap, magnetic sector or FT-ICR or combinations thereof. Ideally the ion source of the mass spectrometer should yield mainly sample molecular ions, or pseudo-molecular ions, and few fragment ions. Examples of such ion sources include atmospheric pressure ionization sources (e.g. electrospray and atmospheric chemical ionization) and Matrix Assisted Laser Desorption Ionization ("MALDI").

Ideally the mass spectrometer will accurately measure the mass of a chemical species of interest to within 20 ppm of its exact or calculated mass, more preferably to accuracy to within 10 ppm of its exact or calculated mass, and most preferably to an accuracy within 5 ppm of its exact or calculated mass.

Ideally the mass analyzer should sample and record the whole mass spectrum simultaneously and with a frequency that allows enough spectra to be acquired for a plurality of components in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

The preferred embodiment takes advantage of the fact that each chemical component in a complex chemical mixture can be characterized in a highly specific manner by measurement of its accurate mass and one or more additional physico-chemical properties. This highly specific information allows chemical components common to different chemical mixtures to be matched and quantitatively compared. In some experiments, when the chemical components in a sample mixture are known to be constrained to a well characterized list of chemical components, it is also possible to qualitatively identify the chemical components in the mixture.

Although the methods of the preferred embodiment may be applied to a wide variety of life science experiments, the description of its application to the qualitative and quantitative characterization of a protein mixture is illustrative. The protein mixture may be simple in composition or it may be comprised of at least 100 proteins or even greater than 1,000 proteins.

According to an embodiment the method comprises the following steps:

subjecting a mixture of proteins to one or more separation steps while recording the physico-chemical properties of each fraction collected;

digesting the proteins present in the resulting fractions with a selective peptidase to obtain mixtures of protein fragments or polypeptides;

subjecting the resulting polypeptide mixtures to one or more chromatographic separation steps while recording the associated chromatographic elution times;

accurately measuring the masses of individual polypeptides in the resulting fractions by mass spectrometry;

identifying individual polypeptides by comparing their measured accurate mass and one or more physical chemical properties to the calculated accurate mass and physico-chemical properties of polypeptides which could theoretically be associated with a constrained list of proteins that is representative of the sample being studied.

In some situations it is of interest to quantitatively compare the relative level of individual proteins in two different sample mixtures of biological origin. For example, the two protein mixtures may be representative of two different states of an organism such as diseased versus normal or treated versus untreated. The information gained above facilitates such a quantitative assessment. Mixtures of this type which are of similar biological origin and which been prepared in a nearly identical manner according to good analytical practice are for the most part very similar qualitatively and quantitatively in chemical composition. In general, most of the proteins in such mixtures are qualitatively the same and they are present in the same relative abundance. Polypeptides from these proteins represent a pool of endogenous internal standards which facilitate the discovery and quantitative measurement of polypeptides and hence the proteins that have changed in their relative abundance in the two sample states being compared.

According to an embodiment the method comprises matching polypeptides that are common to the one or more mixtures being compared based on their distinguishing accurate mass and physical chemical properties. It is not necessary for the chemical identity of each polypeptide to be known for a match to be accomplished. It is only necessary that the physico-chemical property signature of each polypeptide allows it to be uniquely distinguished from other polypeptides in the mixture. A number of endogenous polypeptides may be tested to determine if they qualify as internal standards. A polypeptide qualifies as an internal standard if its abundance level relative to other specific polypeptides in the mixture does not vary in a statistically significant manner when compared to the same polypeptide abundance ratios in the other sample state mixtures of interest. The ratio of the abundance of each polypeptide in each mixture relative to the abundance of a designated internal standard common to each mixture may be determined. This ratio may be compared for each polypeptide which has been matched between mixtures to determine if its relative expression level has changed between the sample states being compared.

Complex sample mixtures may be separated by using a variety of physical processes, such as for example, centrifugation, or through the use of one or more dimensions of chromatography such as, for example, size exclusion, anion exchange, cation exchange, gel electrophoresis, normal phase, reverse phase or combinations thereof. These separation steps may be done off-line or on-line with the mass spectrometric measurement process. In the investigation of biopolymers, as for example proteins, the separations may optionally be done on the intact proteins prior to enzymatic digestion as well as on the protein digestion products. The primary goal of the separation process is to produce fractions in a well defined and reproducible manner. In many cases these separation processes will produce sample fractions with definable physico-chemical properties.

An embodiment includes the steps of measuring two or more physico-chemical properties of each chemical component in a mixture with one of these properties being its accurate mass as determined by mass spectrometry. The chemical components common to two different mixtures are allowed to be matched and compared quantitatively based on the distinguishing nature of this accurate mass and physico-chemical property information. These chemical components can also be qualitatively identified when their measured accurate mass and physico-chemical properties can be matched against the calculated accurate mass and physico-chemical properties of a constrained list of chemical species which are known to represent the chemical mixture being studied.

There are a plurality of chemical species in many chemical mixtures of biological origin that have calculated molecular masses which are unique unto themselves within some mass tolerance. It is possible to assign a unique signature to a chemical component in a mixture based on accurate mass measurement alone if the inherent mass error of the mass spectrometric measurement process is sufficient to distinguish it from other components in the mixture that are similar in mass.

Additional physico-chemical properties which could provide unique signature information for a chemical component in a complex mixture of biological origin are, for example, solubility, hydrophobicity, hydrophilicity, net charge, pI, pKa, molecular volume, and antibody affinity. Some of these parameters can be related to a chemical component's measured elution order in a chromatographic separation. One such distinguishing physico-chemical property is elution order in a reverse phase chromatographic separation which is a measure of the hydrophobicity of a chemical component. Chromatographic retention time or relative retention time in combination with accurate mass is frequently sufficient to uniquely distinguish a chemical component in a complex metabolite mixture or a protein digest mixture thus allowing its relative abundance to be quantitatively compared to a like component in a second mixture. This concept can be extended to include the actual qualitative identification of polypeptides in a protein digest mixture if the composition of the unknown sample is known to be constrained to a particular list of proteins. In this case the elution order of an unknown polypeptide relative to known polypeptide standards is used to estimate its hydrophobicity. This measured value of hydrophobicity can then be compared to the theoretical hydrophobicity of all the polypeptides which could theoretically be contained in the mixture. This hydrophobicity constraint in combination with accurate mass may be used to uniquely identify the unknown polypeptide.

Another example physico-chemical property which is of utility as a distinguishing chemical signature is isoelectric point (pI). Intact proteins may be electrophoretically fractionated on the basis of (pI). Small molecules and polypeptides may be fractionated under appropriate conditions by on exchange chromatography on the basis of pI. These measured values of pI for an unknown chemical species can be compared to calculated values of pI for chemical species which could theoretically be contained in the mixture of interest.

Yet another example physico-chemical property which is of utility as a distinguishing chemical signature is charge state as ascertained in the mass spectrometric measurement process. This is of particular value as a distinguishing signature for polypeptides. The present inventors have empirically determined that a polypeptide ion's charge-state ($2^+$, $3^+$, $4^+$, etc.) can be estimated from the length of its sequence and the number of basic amino acids contained in its sequence. For example, such information allows the correct polypeptide to be identified when more than one polypeptide that could be theoretically contained in the mixture of interest is consistent with the measured accurate mass of the unknown peptide.

The meaning of a number of terms used throughout the present application will now be given. "AEX" stands for Anion Exchange High Performance Liquid Chromatography. "Area" is the mass spectral signal integrated over time for a measured polypeptide fragment. "Area Ratio" is the division of the area from a peptide in a given sample (such as Experimental) by the area from a peptide in another sample (such as Control). "B&B" is the Bull and Breese value, a measure of hydrophobicity. See H. B. Bull, K. Breese, Hydrophobicity estimates for proteins and peptides, *Arch. Biochem. Biophys.* 161:665-670 (1974). "Calibration Lock Mass" is where an analyte is used to correct for fluctuations in mass measurements during data acquisition, in order to improve mass accuracy. "CAM" stands for Carboxamidomethyl group, a chemical moiety usually attached to sulfhydryl groups by treatment of a protein or peptide with a reducing agent such a mercaptoethanol or dithiothreitol, followed by the alkylating agent 2-iodoacetamide. "Candidate Protein" is a protein to which a statistically significant number of peptides can be assigned by mass alone. "CEX" stands for Cation Exchange High Performance Liquid Chromatography. "Charge-State" is the number of protons attached to a peptide molecule during the ionization (ion formation) process in the ion source of a mass spectrometer. "Composite Ion Map" is a list of all measured physiochemical properties and areas of all peptides and all proteins identified and qualified in an Ion-Mapping experiment. "Composite UML" is a non-redundant list generated by comparing two of any types of Unique Mass Lists (UMLs). Included in the Composite UML is the status of each peptide as a function of their UMLs. This process is repeatable to generate further Composite UMLs. "Compressed UML" is the intersected portion of a Composite UML, where the area(s) are the median values. "Database" is a collection of sequences of proteins and/or peptides hypothesized to be present in the proteome under study, including all their respective physiochemical properties. "Endogenous Reference Protein (ERP)" is an endogenous protein hypothesized to be present in all the samples and used for normalization of experimental parameters. "HPLC Index" is a measure of hydrophobicity. See *Biochemistry*, 25:5425 (1986). "Intensity Value" is the sum of all centroided mass spectral signals for all isotopes of all charge-states of any ion exceeding the minimum threshold for ion detection. "Internal Reference Protein (IRP)" is an exogenous protein introduced into a sample under study and used for normalization of experimental parameters. "Internal Standard (IS)" is an exogenous peptide, of known molecular weight and concentration, added to the peptide fractions immediately prior to the final separation. "Ion Map" is a list of all measured physiochemical properties and areas of all peptides from a single protein identified and qualified in an Ion-Mapping experiment. "Physico-chemical Property" is any measurable characteristic of a protein, peptide or other biological molecule which may serve as a basis for its separation or description. "Post-Translational Modification(s) (PTM)" are all changes to a protein following-its assembly from individual amino acids. "Post-Translational Modification (PTM) Candidate" is a peptide whose changes in physico-chemical properties support the hypothesis of post-translational modification. "Proteome" is the proteins present in a living cell at any given point in time. "Qualification Algorithm" is a computational tool which uses experimental values contained in any UML, Composite UML, Ion Map, and/or Composite Ion Map and compares it with calculated values from database(s) in order to identify peptides, and thereby proteins, in the mixture(s). "Qualified Protein" is a protein to which a statistically significant number of peptides can be further assigned by physico-chemical properties other than mass. "Signature peptide" is a peptide that can be assigned to a protein based on mass alone. "Unique Mass List (UML)" is a non-redundant list of values such as mass, area, retention time, charge-state etc., obtained from an Ion-Mapping experiment. "Unique Mass List Browser (UMLB)" is a software tool designed to compare and normalize any two UMLs, Composite UMLs or Composite Ion Maps in order to determine their comparative status. "Unique Mass List Generator (UMLG)" is a user-definable software tool that interrogates and reduces raw data generated from an Ion Mapping experiment to extract a non redundant list of data points. "Up Regulation, Down Regulation" is the change in the abundance of a peptide or protein between two physiological conditions. "Validated protein" is a qualified protein whose peptides all track quantitatively between two experiments.

Various embodiments of the present invention will now be described, by way of example only, and with reference to the accompanying drawings in which.

Figure 5:
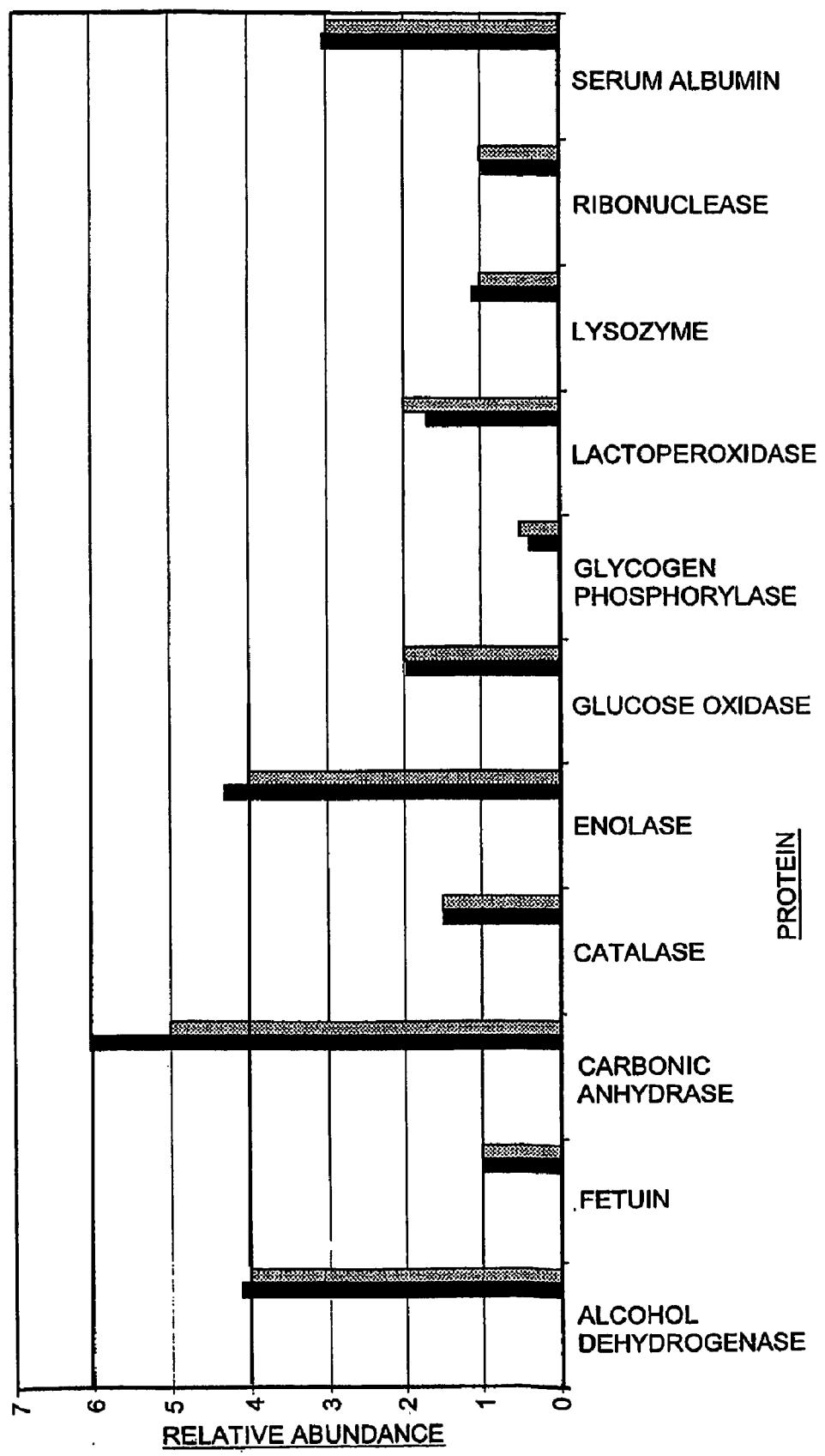

FIG. 4 details the composition of two mixtures;

FIG. 5 shows a histogram of observed versus theoretical abundance for a mixture B/mixture A;

FIG. 6 shows a BSA unique mass list;

FIG. 7A shows an indexed peptide database for Bovine Serum Albumin which is continued on FIGS. 7B-7D;

FIG. 8 shows measured and calculated match results for a BSA protein digest;

FIGS. 9A-9M detail a protein qualitative match; and

FIG. 10 shows a rat urine metabolism comparative study.

E. COLI

There are a substantial number of peptides whose calculated molecular masses are unique unto themselves within some mass tolerance. Clearly the more accurate the measuring device, the better the chances are of identifying a large number of these types of peptides. Peptides that have no neighbors within the inherent mass error of the measuring device are referred to as Accurate Mass Signature Ions for their respective parent protein. To illustrate this point, a non-redundant protein database of the proteome of *E. coli* was indexed using the Indexing Algorithm described below. When the entire *E. coli* proteome was analyzed, in silico, for the expected products of digestion with trypsin, 191,777 theoretical peptides were generated. The Indexer was set to report only those peptides between molecular mass 500 and 5000 with up to one missed cleavage. Calculated theoretical physico-chemical properties include but were not limited to the predicted retention time and the predicted charge state. The indexed database was queried for those peptides that were unique to within 5 ppm of their corresponding accurate mass (i.e. for which no other peptide in the database had a mass within 5 ppm). The query resulted in a list of 20,455 peptides identifying 4023 (95%) of the 4234 annotated proteins in the non-redundant E. coli database.

The in-silico analysis illustrates the ability to qualitatively identify 95% of the proteins in the E. coli proteome by generating an accurate mass measurement of the signature ions from each respective protein. However, this does not mean that an experimental enzymatic digestion of a whole-cell lysate will produce all theoretical signature peptides from all the proteins in the proteome. Typically any type of mass spectrometric analysis of an enzymatically or chemically fragmented protein results in a sequence coverage of between 20 and 60%, therefore increasing the number of signature ions per protein becomes important if the goal is to qualitatively identify as many proteins as possible in a proteome. In the case of the trypsin-treated E. coli proteome (with up to one missed cleavage) only 10.6% of the peptides are signature ions. So the question becomes, how can one increase the number of signature ions per protein as the sample becomes more complex.

To increase the number of signature ions per protein the method of the preferred embodiment employs a second fractionation method utilizing an additional physico-chemical property, preferably hydrophobicity. Just as each amino acid has a defined molecular mass, each also has a defined hydrophobicity and can be separated according to this property using the appropriate chromatographic column and solvent system, typically reverse-phase liquid chromatography. The hydrophobicity of a peptide may be calculated by summing the hydrophobicity value for each amino acid in a peptide sequence. In some instances the value is corrected by multiplying the sum by a correction coefficient, which directly relates to the peptide length. Thus a peptide's hydrophobicity can be considered to be a second physical constant, i.e. a second physico-chemical property. By using a hydrophobicity curve generated by accurate mass analysis of an Intact Reference Protein, each of the theoretical peptides in the indexed non-redundant E. coli database may be assigned a calculated hydrophobicity and a theoretical retention time. One can then query the database for ions that are unique (hydrophobicity signature ions) within some retention time window. For example, setting the retention time window to +/−2.5 minutes and removing all accurate mass signature ions from the database, and then querying the indexed non-redundant E. coli database, resulted in 74,239 hydrophobicity signature ions (38.7%). Combining the two physico-chemical properties of mass and hydrophobicity identifies 94,671 peptides which are unique to the protein they are derived from. Querying these 94,671 ions against the indexed non-redundant E. coli database resulted in the identification of 100% of the 4234 proteins. Depending on the complexity of the proteome under investigation (E. coli 4,234, Yeast 6,173, Human 35,000 plus) it may be necessary to further increase the number of signature ions per protein to raise the minimum sequence coverage to some acceptable user-defined level.

When this is necessary, the preferred embodiment employs a third physico-chemical property, such as for example the isoelectric point (pI). Just as each amino acid has a defined molecular mass and hydrophobicity, it also has a defined pI and can be separated by ion exchange chromatography in conjunction with an appropriate elution gradient and buffer composition. In instances where peptide pI is employed as a physico-chemical property, the enzymatically-derived peptide pool is first separated by ion exchange chromatography. Accurate mass physico-chemical property analysis identifies the peptide ions from the intact reference protein(s) present in each salt fraction thereby providing a pI range for each. A pI tolerance window can then be assigned for each fraction. One can then query the indexed non-redundant E. coli protein database for ions that are unique unto themselves (pI signature ions) within some pI tolerance window. For example, setting the pI tolerance window to +/−2 pI units, removing all accurate mass and hydrophobicity signature ions, and then querying the indexed non-redundant E. coli database resulted in 16,470 pI signature ions (8.6%). Combining the three physico-chemical properties results in 111,141 peptides which are unique to the protein they are derived from. Querying these 111,141 ions against the indexed non-redundant E. coli database resulted in all 4234 proteins (100%) being identified.

If the desired level of sequence coverage has not been reached by employing three physico-chemical properties, a fourth physico-chemical property, such as for example the charge state of the peptide, can be used. Given a specific buffer system (typically pH <2) for an accurate mass LCMS analysis, a peptide ion's charge-state(s) will be determined by the peptide length, composition, and sequence. Through mass spectrometric and physico-chemical property analysis of many peptides from many different reference proteins, the present inventors have empirically determined that a peptide ion's charge-state ($2^+$, $3^+$, $4^+$, etc.) can be predicted from its sequence and length. As an example, if the sequence is >18 amino acids long and contains an internal basic residue at position 9 the combined weighted charge-state for that peptide ion will be 2.5+/−0.2. Using these empirically-derived charge-state rules, the method of the preferred embodiment assigns a theoretical charge state to each of the 191,777 theoretical peptides in the indexed non-redundant E. coli protein database and generates a list of charge-state signature ions.

The preferred embodiment optionally employs additional separation methodologies for further increasing the number of signature ions per protein. It will be apparent to those skilled in the art of protein and peptide fractionation that a variety of different chromatographic separation technologies may be employed to further fractionate complex samples. Such separation technologies include but are not limited to gel permeation (size exclusion) chromatography, anion and cation exchange chromatography, capillary electrophoresis, isoelectric focusing, and the many forms of affinity chromatography. The separation methods may be applied to both intact proteins and the peptide fragments derived therefrom. Preferably, each successive round of separation increases the number of signature ions unique to the protein they emanate from, until all proteins within the proteome under investigation have enough signature ions to achieve the desired level of peptide identification.

It will be apparent that as the resolution of the mass spectrometer decreases, the number of physicochemical properties, and/or the level of resolution with which they are measured and calculated, must increase to maintain a given level of signature ions. For this reason, it is preferable that the mass spectrometer have the highest possible resolution, within the practical constraints of expense and throughput.

The Ion Mapping Process

An example of the preferred ion mapping will now be described with reference to the "in silico" digestion of proteins. The amino acid sequences of the proteins of interest that make up the mixture to be analyzed are examined by any of several known automated methods to identify cleavage sites where the enzyme to be used is likely to cleave them. Programs are available via the world wide web for the purpose of calculating masses of peptide fragments expected from digestion, for example MS-Digest, located at (http://) prospector.ucsf.edu/ucsfhtml3.4/msdigest.htm. The proteins of interest may be the entire genome of an organism, and the sequences may be derived from readily available genomic and proteomic databases. The peptide fragments expected to be generated by the enzyme or enzymes to be used may be calculated "on the fly" and compared to stored results of an Ion Mapping experiment and/or the data on the expected fragments may be pre-calculated and stored, and the results from an Ion Mapping experiment compared against the stored data approximately as fast as it is generated.

In one embodiment of the invention, the method of creating a theoretical ion map of at least one polypeptide comprises one or more of the following steps:

optionally translating sequences in database (e.g. take a DNA database and translate it into a protein or EST database);

calculate predicted molecular weight and pI for native proteins from which peptides derived;

associate each peptide to the MW and pI of the native parent protein;

perform in silico trypsin digest using known trypsin substrate patterns (provide reference for predicted trypsin patterns);

optionally calculate theoretical accurate mass and/or mass to charge ratio(s) of each of the resulting fragments;

optionally set a threshold "Mass Scrutable" Masses (e.g., >8,000 daltons and <500 daltons—masses much above about 8,000 daltons are difficult to weigh with the resolution necessary to identify amino acid composition; peptides shorter than about 5 amino acids are too common to be of much diagnostic use);

optionally set a threshold for calculated missed cleaves (provide reference for missed cleavages);

optionally calculate hydrophobicity indices for all or some peptides (e.g. by the Bull and Breese method);

optionally calculate the pI for all or some peptides;

optionally calculate the theoretical charge for all or some peptides;

optionally maintain the annotations of each native parent protein in the database (e.g. a protein database may incorporate knowledge of post-translational modifications, splice variants, etc.);

optionally calculate all of the phosphorylation sites of native peptide (this may be done via the world wide web, for example by using the prosite resource at www.expasy.org/prosite/ (using the http:// protocol) or similar programs running on a local computer);

optionally calculate all of the glycosylation sites of native peptide (this may be done via the world wide web, for example by using the netOglyc resource at www.cbs.dtu.dk/services/NetOGlyc/ (using the http:// protocol)).

FIG. 1 shows a flow diagram of the steps undertaken in the ion mapping process. The process as presented in FIG. 1 includes the assessment of a control sample and experimental sample along with an intact reference protein sample(s). Each aspect of the process is described in more detail below.

Control Sample/Experimental Sample

Ion mapping may be used to identify proteins in complex mixtures and/or to compare quantitatively the relative expression level of proteins taken from one or more control and experimental sample sources.

Isolation and Pre-Fractionation of Intact Protein Mixture

If a goal of the Ion Mapping study is to quantitatively compare the relative expression level of proteins in two different samples, then similar amounts of complex protein mixture would be isolated from one or more control and experimental sample sources. These intact protein mixtures may be derived from any number of sources including whole cell lysates, partially fractionated protein complexes, and subcellular organelles to name a few. Intact protein mixtures taken from one or more control and experimental sources may be fractionated by any number of a number of different methodologies known in the art including but not limited to one-dimensional gel electrophoresis, capillary electrophoresis, liquid phase iso-electric point focusing, affinity chromatography, single or multi-dimensional anion or cation exchange chromatography, reverse phase chromatography and partitioning centrifugation. Fractionation of complex intact protein mixtures is one way to increase the dynamic range of proteins that can be identified and/or quantitatively compared using the method(s) of the preferred embodiment.

Sample Known Amount of Intact Protein Mixture

Similar amounts of intact complex protein mixture should be isolated from the raw and/or fractionated control and experimental sample sources to simplify subsequent quantitative comparisons.

Add Intact (Exogenous) Protein Internal Standard(s)

The same amount of one or more intact proteins known not to be native to the complex protein mixtures being studied may be added to the control and experimental samples as an internal standard(s). These intact protein internal standards provide several valuable quality control checks in the ion mapping study. The relative level of peptides produced from the digestion of internal standard proteins and native proteins provides a measure that the control and experimental complex protein mixtures have been digested, reduced, and derivatized with similar efficiency. The peptides produced from the digestion of the internal standard protein(s) also serve as markers to monitor chromatographic retention time reproducibility in subsequent peptide separation procedures and to monitor mass measurement accuracy.

Create Intact Protein Internal Standard(s) Blank Sample

An independent sample of the intact protein(s) used as internal standard(s) in the control and experimental samples will be subjected to the same digestion, reduction, and derivatization procedures as well as the same chromatographic and ionization conditions incorporated in the Ion Mapping analysis of the control and experimental samples. This will allow the identification of the peptides associated with the internal standards. It will also allow the identification of background ions which should be excluded from subsequent qualitative identification and/or quantitative comparison procedures.

Chemical/Enzymatic Digestion of Protein Mixture

Any number of previously described methodologies can be used to generate peptide fragments from the control and experimental complex intact protein mixtures and from the internal standard intact protein mixture. Such methodologies for protein fragmentation may include but are not limited to enzymatic or chemical digestion.

Optional Single or Multi-Dimensional Chromatographic Separation

Single or multi-dimensional liquid phase chromatographic separation methodologies may be applied to reduce the complexity of the peptide mixtures produced in the digestion of the control, experimental and internal standard/background protein mixtures prior to mass spectrometric analysis. These liquid phase chromatographic separation methodologies could include anion or cation exchange chromatography, reverse phase chromatography, Capillary Electrophoresis Chromatography ("CEC"), or any combination of these or other previously described prior art relating to the chromatographic separation of peptides contained in non-equimolar, heterogeneous complex mixtures. These liquid chromatographic separation methodologies may be directly coupled or used independently to produce sub-fractions of the peptide pool. Typically, the final liquid chromatographic separation will be directly interfaced to the ion source of a mass spectrometer capable of accurate mass measurement.

Optionally Add Internal Standard B for Injection Volume Correction

The same amount of one or more internal standard compounds may be added to each sample mixture prior to liquid chromatography-mass spectrometry (LC-MS) analysis. The primary purpose of this optional internal standard(s) is to correct for chromatographic injection volume variations, but it can also serve as a chromatographic retention time standard and mass accuracy check standard as well.

Liquid Chromatography Accurate Mass Analysis

The final stage of liquid chromatographic separation of the peptide pools produced from the digestion of the control, experimental, and internal standard blank protein samples is directly coupled to a mass spectrometer capable of accurate mass measurement. A mass spectrometer capable of routinely providing mass measurement accuracy to within 10 parts per million (ppm) of the theoretically calculated mass is acceptable. However, routine mass measurement accuracy equal to or less than 5 ppm of the theoretically calculated mass is desirable. The type of mass spectrometer capable of this accurate mass measurement process might include Time of Flight, Fourier transform ion cyclotron resonance, or magnetic sector to name a few.

Process Results Using Unique Mass List Generator

The liquid chromatography accurate mass information is processed using a Unique Mass List Generator which uses threshold criteria based on mass accuracy, charge state, chromatographic peak intensity and area, and calculated hydrophobicity, among others, to generate a list of unique ions which can be compared to lists derived in a similar manner from other LC-MS analyses.

Identify and Quantify Internal Standard Components

Both the peptide digestion products from the optional intact protein internal standard(s) and the optional post-digestion "B" internal standard(s) that were added to the Control, Experimental and Internal Standard/Blank samples are identified in the unique mass list information sets generated for each of these samples and flagged for non-consideration as native peptide candidate ions.

Internal Standard B Correction of Native Peptide Peak Areas

The peak area of each component identified by the unique mass list generator is corrected for LC-MS injection volume deviations by ratioing against the peak area of the optional "B" internal standards.

Compile List of Background Ions for Unique Mass List Blank Correction

All non-internal standard ions identified in the Intact Protein Internal Standard(s) Blank Sample are designated as background ions and are compiled in an exclude list.

Remove Background Ions from Unique Mass List

Background ions identified in the Intact Protein Internal Standard(s) Blank Sample are removed from consideration as native peptide candidate ions in the Control and Experimental Sample Unique Mass Lists.

Estimate Relative Digestion Efficiency from Protein Internal Standard

The peak areas of peptide ions associated with the Intact Protein Internal Standard(s) which were added to the Control and Experimental Samples prior to digestion are compared to the peak areas of a number of native peptide ions in the Control and Experimental Samples to determine that both samples were digested with comparable efficiency.

Compare Internal Standard Corrected Accurate Mass Chromatogram Peak Areas for Polypeptides from Control Sample and Experimental Sample The internal standard corrected accurate mass peak areas for unique mass list peptide ions remaining after background correction in the Control Sample are compared to similarly corrected accurate mass peak areas for unique mass list peptide ions in the Experimental Sample. Peptide ions to be compared are matched according to user-defined accurate mass, and chromatographic retention time threshold criteria. If the ratio of peak area for an Experimental Sample peptide ion that is matched to a Control Sample peptide is above or below user-defined expression level threshold criteria or if an Experimental Sample peptide ion is not matched against a Control Sample peptide ion, then the Experimental Sample peptide ion is flagged for further effort to qualitatively identify the protein from which it derived. If the ratio of peak area for an Experimental Sample peptide ion that is matched to a Control Sample peptide ion is within user-defined expression level threshold criteria, then further effort to qualitatively identify the protein from which it is derived may or may not be pursued.

Qualitative Identification Biologically Important

If the ratio of peak area for an Experimental Sample peptide ion that is matched to a Control Sample peptide ion is within user-defined expression level threshold criteria, then further effort to qualitatively identify the protein from which it is derived may be pursued if this information is considered to be biologically important or otherwise relevant to the goals of the study. Otherwise, the analytical information that was determined for the Experimental Sample peptide ion is recorded in a database and no further efforts to qualitatively identify the protein from which it is derived are pursued.

Perform High Mass Accuracy Peptide Mass Fingerprint (PMF) Data Base Search on Unique Mass List Ions Experimental Sample peptide ions submitted for qualitative identification are searched against a non-redundant protein database. Database searches are restricted by the mass measurement accuracy of the Experimental Sample peptide ion as well as by one or more physical-chemical properties that may be known about the source of the proteins included in the experimental sample. Relevant physical-chemical properties may include sample source organism, sub-cellular sample fraction, protein molecular weight range, and protein pI to name a few.

Tabulate or Form a Redundancy List of all Unique Mass List Peptides Consistent with Each Tentative PMF Protein Identification Experimental Sample Unique Mass List peptides which are tentatively identified via the PMF database search to be associated with the same protein are grouped together to form a redundancy list for each tentatively identified protein.

Determine if Every Peptide Consistent with Each Tentative Peptide Mass Fingerprint Protein Identification has Same Expression Level Shift The expression level shift of each Experimental Sample peptide that has been identified to be consistent with the same protein identification is compared. If the expression level shifts for all the peptides are consistent, then additional qualitative identification checks may be performed e.g. double check retention time. If the expression level shifts are not consistent, then either all of the peptides or at least the peptide(s) which are not consistent in expression level shift may be flagged for LC-MS/MS analysis.

Generate Bull & Breeze Calibration Curves

An optional test for confirming a tentative PMF identification is based on whether the measured Bull & Breeze hydrophobicity/hydrophilicity for each Experimental Sample peptide is consistent with the theoretical Bull & Breeze hydrophobicity/hydrophilicity that the peptide should have if the PMF identification is correct. To this end, the theoretical Bull and Breeze index of known internal standard peptides are plotted against LC-MS retention time to produce a calibration curve from which the measured Bull & Breeze index of each Experimental Sample peptide can be determined.

Test Tentative Peptide Mass Fingerprint Identification Via Application of Qualifying Algorithm A variety of information has been accumulated that can be used to further validate the PMF identification results. Information such as sample source organism, sub-cellular sample fraction, protein molecular weight range, and protein pI, among others, may have been used in entirety or in part to restrict the PMF database search. Additional physico-chemical property information may be tested through the use of a qualifying algorithm to further validate each tentative PMF identification. For example, the algorithm might be used to score the consistency of measured versus theoretical Bull & Breeze index for each unique mass list peptide, it might be used to score the consistency of measured versus theoretical pI of each unique mass list peptide, it might be used to score the consistency of missed cleavage and peptide charge state information, it might be used to score the consistency of histidine containing peptides and charge state information, it might be used to score the consistency of cysteine containing peptides and the measured presence of associated peptides which contain modified cysteine amino acids, and/or it might be used to score the consistency of methionine containing peptides and the measured presence of associated peptides which contain oxidized methionine containing peptides.

Remove Tentatively Identified Masses from Unique Mass List and Create Tentatively Identified Protein List At this point in the data reduction process, all background and optional internal standard related ions have been removed from the Experimental Sample Unique Mass List. Depending on the goals of the study, the Experimental Sample Unique Mass List may have been further restricted to include only those ions which have an apparent expression level difference relative to the Control Sample Unique Mass List ions that is above or below User-defined threshold criteria. In either case, the remaining Experimental Sample Unique Mass List ions are subdivided into those which do satisfy the qualifying algorithm criteria and those which do not satisfy the qualifying algorithm criteria. Ions which do satisfy the qualifying algorithm criteria are moved to a Tentatively Identified Protein List. These ions would generally not be furthered qualified by LC-MS/MS analysis.

Create Orphan Mass List from Unidentified Masses in Unique Mass List

Experimental Sample Unique Mass List ions which do not satisfy the qualifying algorithm criteria are moved to an Orphan Mass List.

Search Orphan Mass List for Post Translationally Modified (PTM) Variants of Tentatively Identified Proteins Orphan Mass List ions are resubmitted to a PMF search specifically to evaluate whether they can be accounted for as post translationally modified variants of the tentatively identified proteins.

Transfer Qualified PTM Hits from Orphan Mass List to Tentatively Identified Protein List Orphan Mass List ions which satisfy Tentatively Identified Protein PTM variant criteria are validated using the qualifying algorithm and are transferred from the Orphan Mass List to the Tentatively Identified Protein List.

Place Remaining Orphan Masses on Include List for LC-MS/MS Analysis

Orphan Mass List ions which do not satisfy Tentatively Identified Protein PTM variant criteria or subsequent qualifying criteria are flagged for LC-MS/MS Analysis.

LC-MS/MS Analysis of Unidentified Orphan Masses and Tentative Protein ID Peptide Masses Requiring Further Verification Unidentified Orphan Masses and any other Peptide Masses which are flagged for further verification may then be analyzed by LC-MS/MS.

Protein Sequence Database Search or EST Database Search or De Novo Sequence LC-MS/MS Results The LC-MS/MS analytical results are processed with software tools that take advantage of the peptide sequence information produced in the MS/MS analysis process. Software tools include Protein Sequence database searching, Expressed Sequence Tag (EST) database searching, and de novo sequencing algorithms to name a few.

Update Tentative Protein ID List with LC-MS/MS Analysis Results

Proteins tentatively identified from the LC-MS/MS analysis are added to the Tentatively Identified Protein List.

Generate Ion Maps and Archive Results for Tentatively Identified Protein and Orphan Peptide Mass Lists All physico-chemical property data and quantitative expression level data for the tentatively identified proteins, their corresponding peptide fragments, and for the Orphan Peptide Mass List Ions are archived in a database and made available for display in a variety of Ion Map formats which illustrate the difference in protein content of the control and experimental samples studied.

Qualification

Before an experimentally derived unique mass can be qualified, the optional Internal Reference Protein(s) (IRP) is digested alone. Again the IRPs are run in triplicate with each resulting UML compared and compressed using specific user-defined parameters and thresholds. As an example for the $E.\ coli$ data set described herein, these parameters were set to +/−5-ppm, 2 minutes, and +/−0.5 charge state. Since the same IRPs are used, all the time data compression provides for a number of different redundancy checks. First, how reproducible the digestion was; second, how reproducible the cysteine derivatization was; and third, how reproducible the ionization efficiency was. All of these parameters can be qualified by comparing the compressed data for that set of IRP accurate mass LCMS analyses to those of others.

Figure 1A:
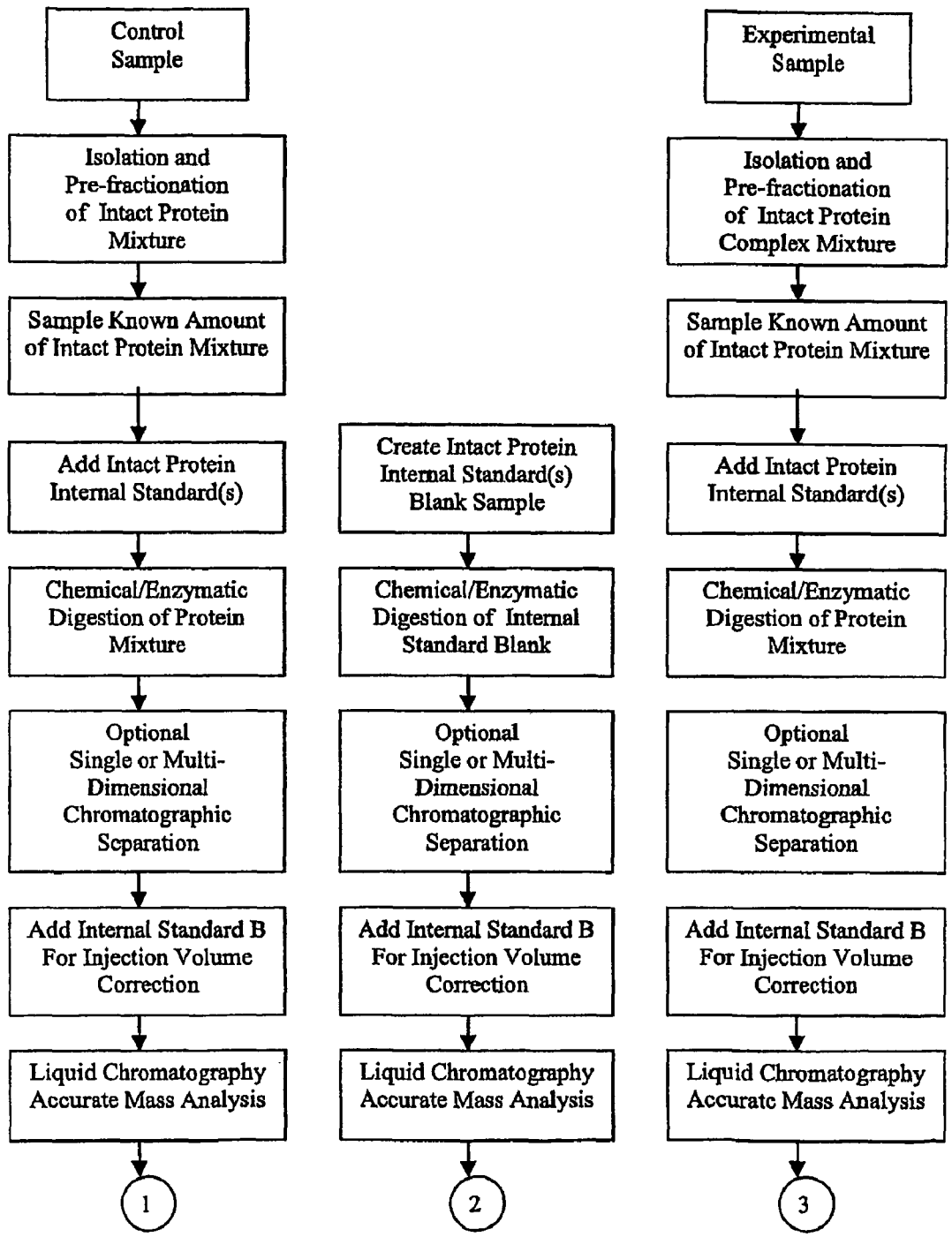
FIGS. 1A-1F show a flow chart depicting a method for analyzing differential protein expression by ion mapping.
Figure 1B:
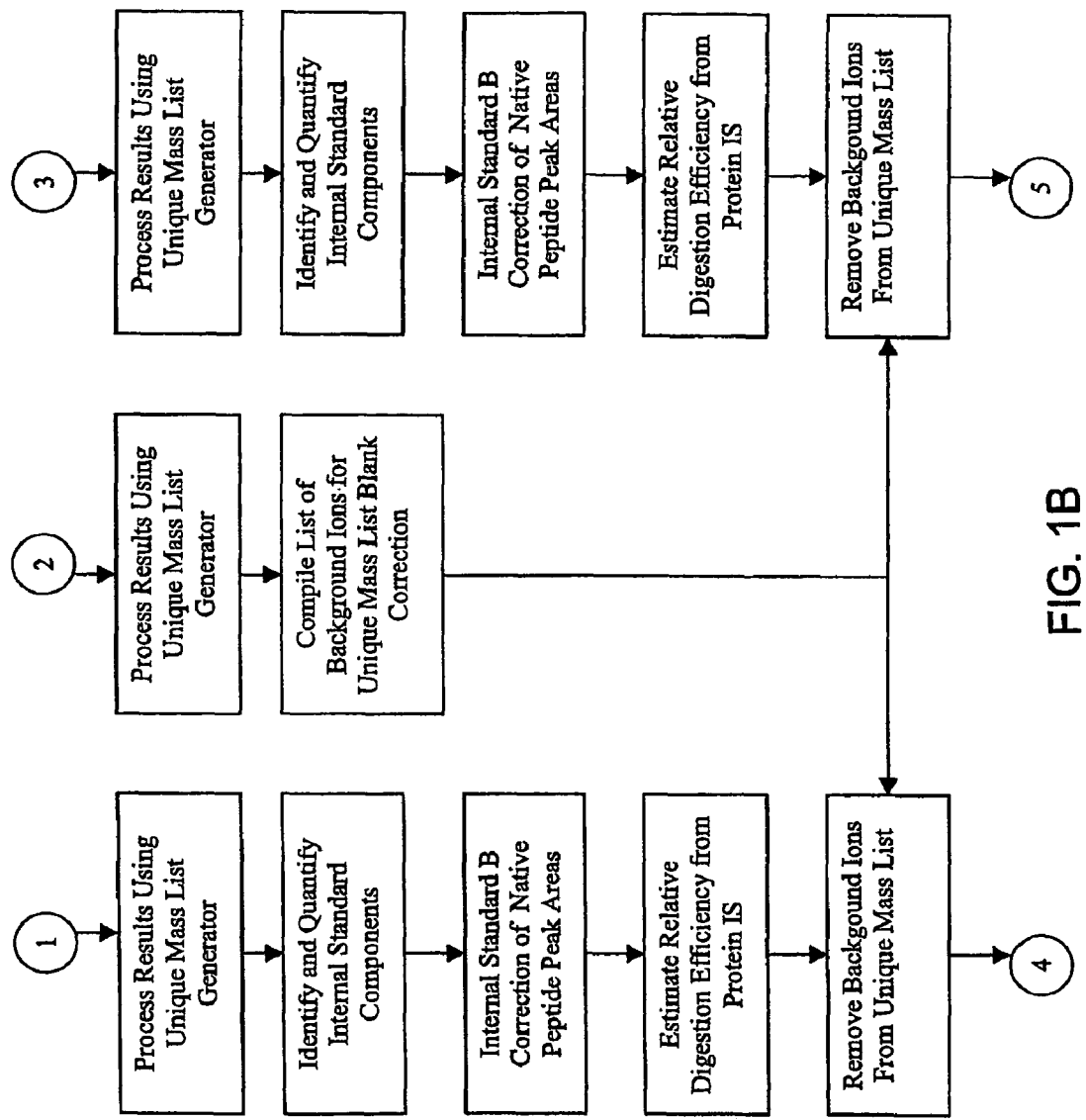
Figure 1C:
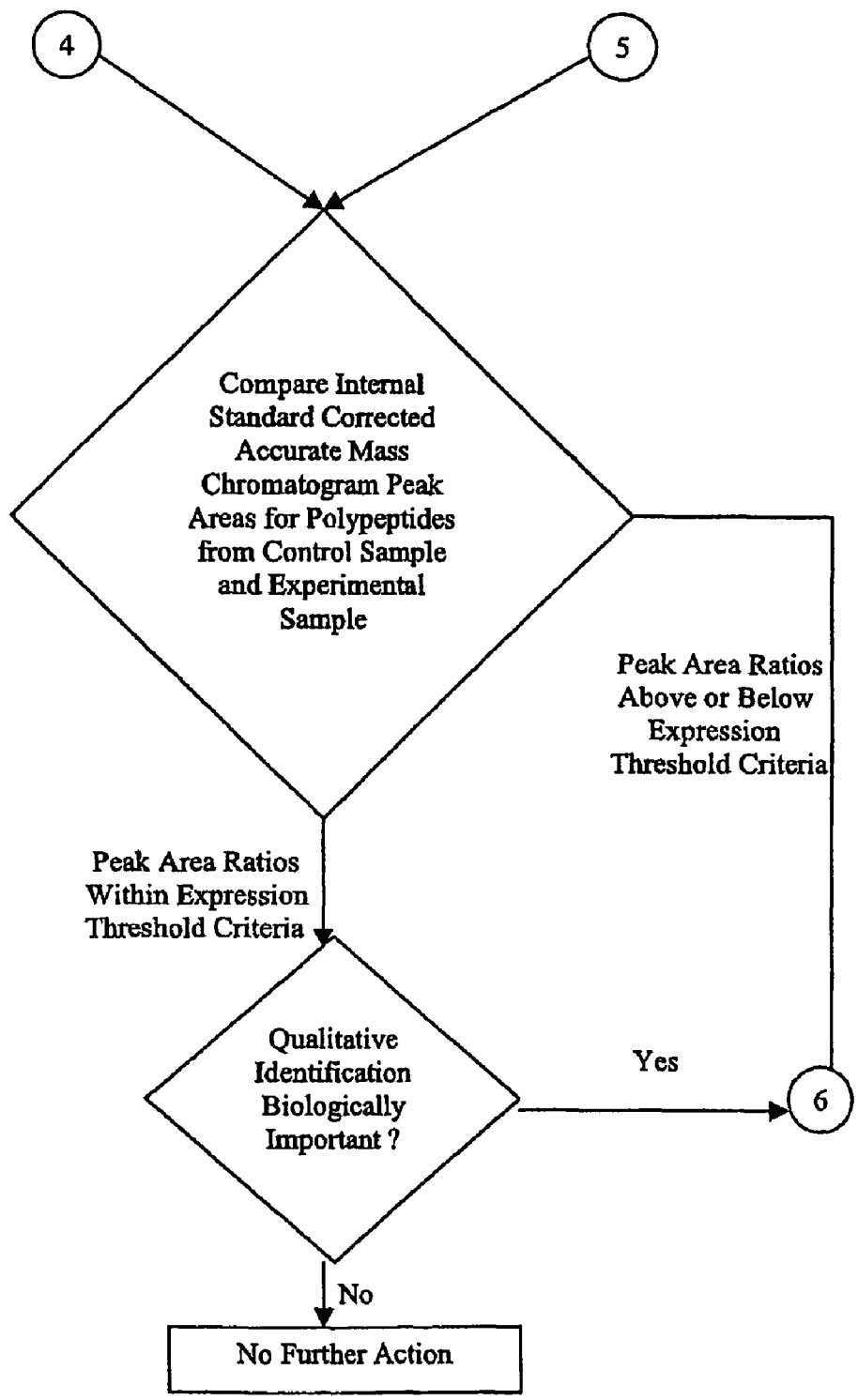
Figure 1D:
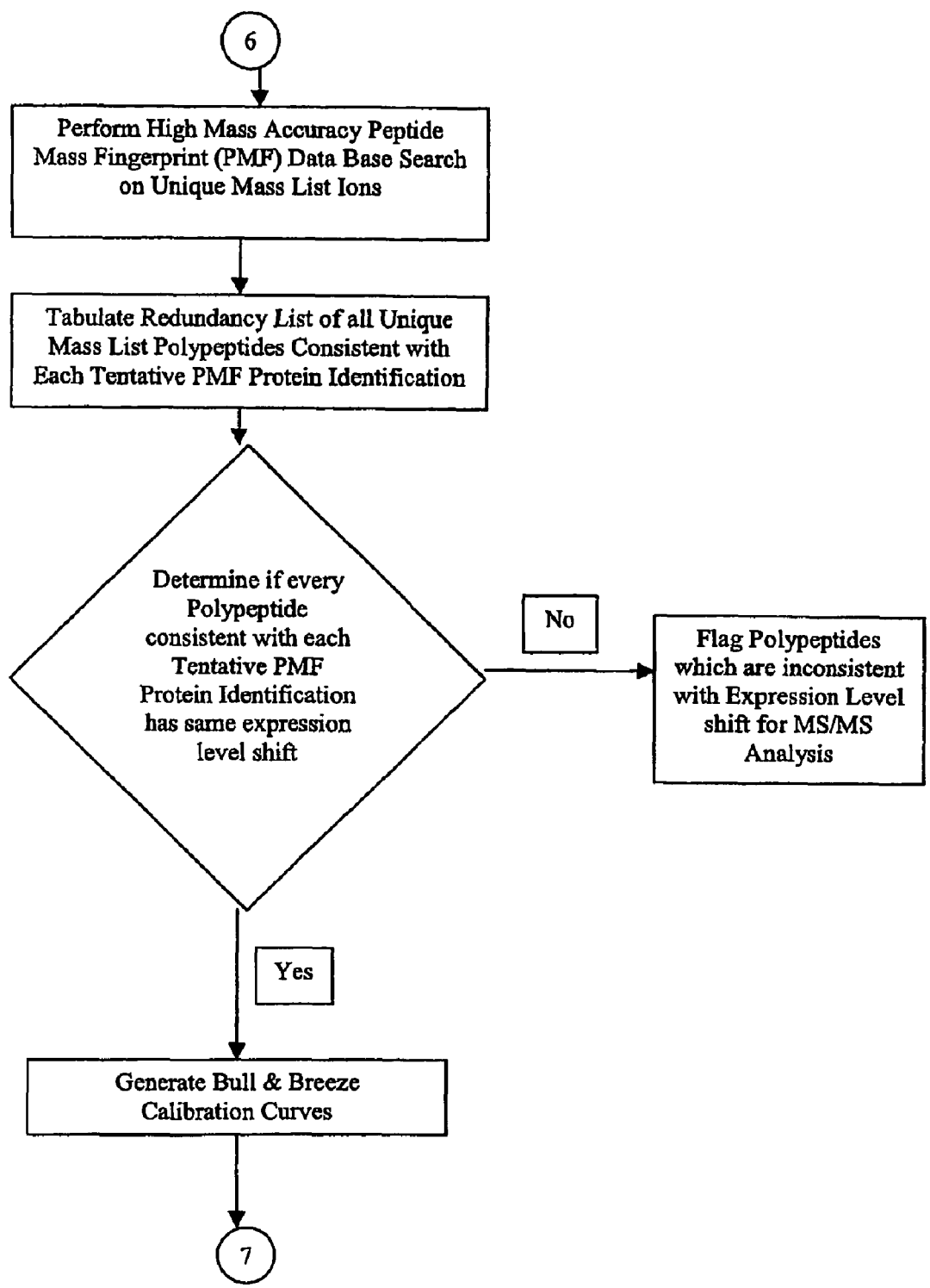
Figure 1E:
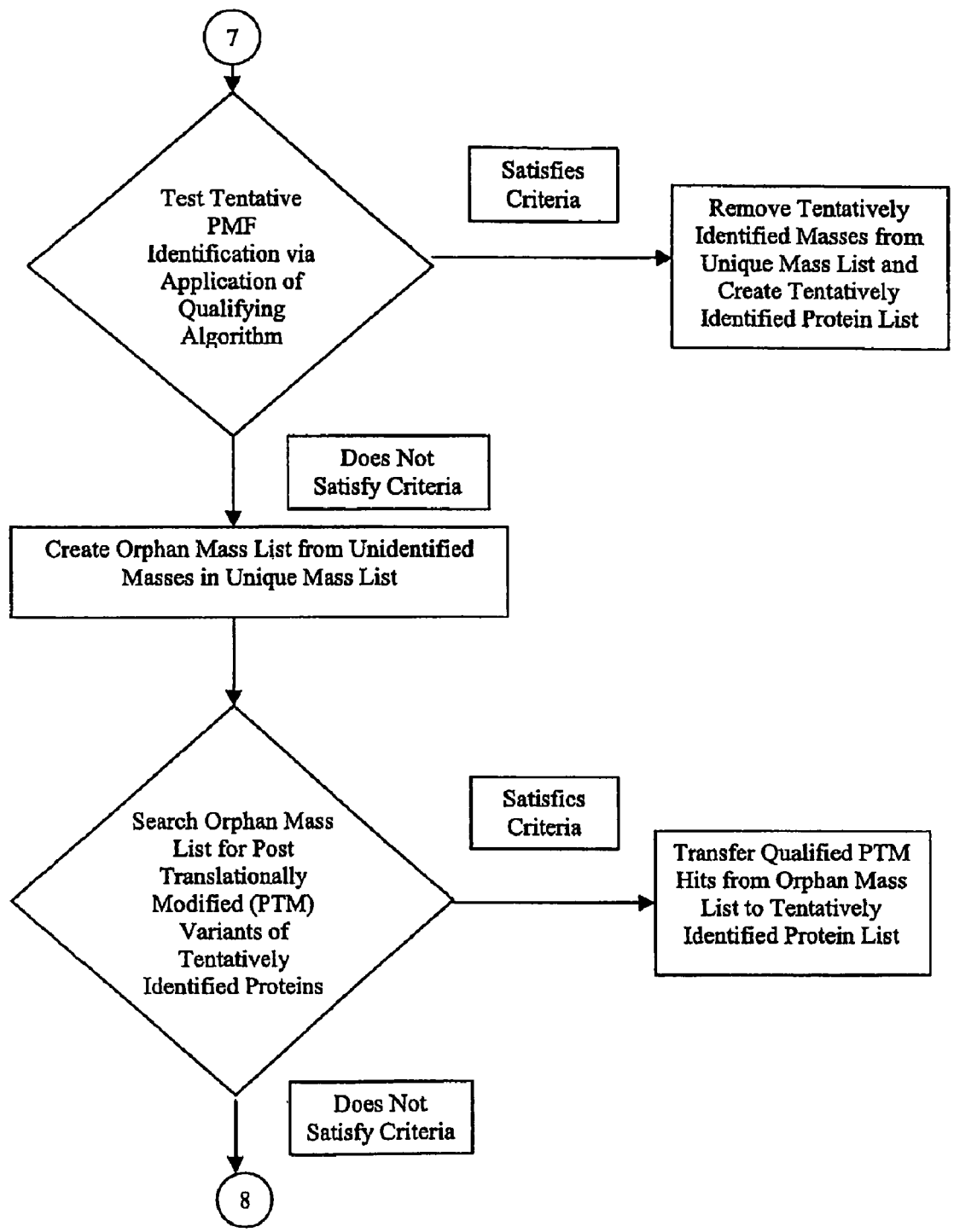
Figure 1F:
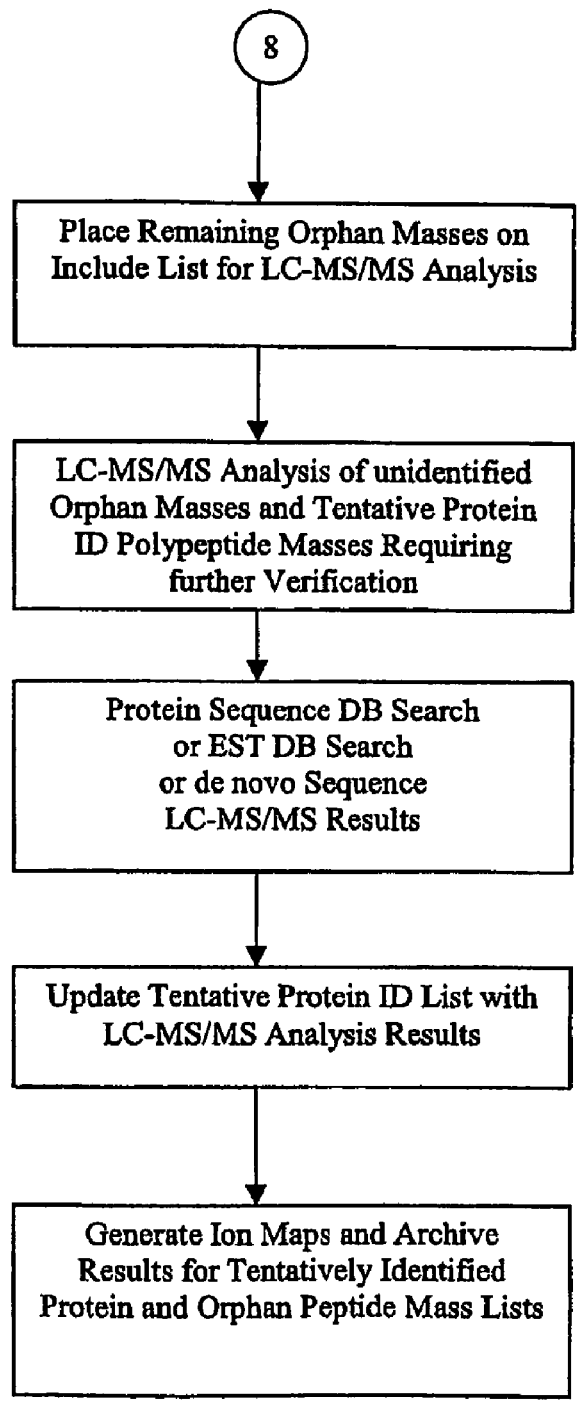
Figure 2:
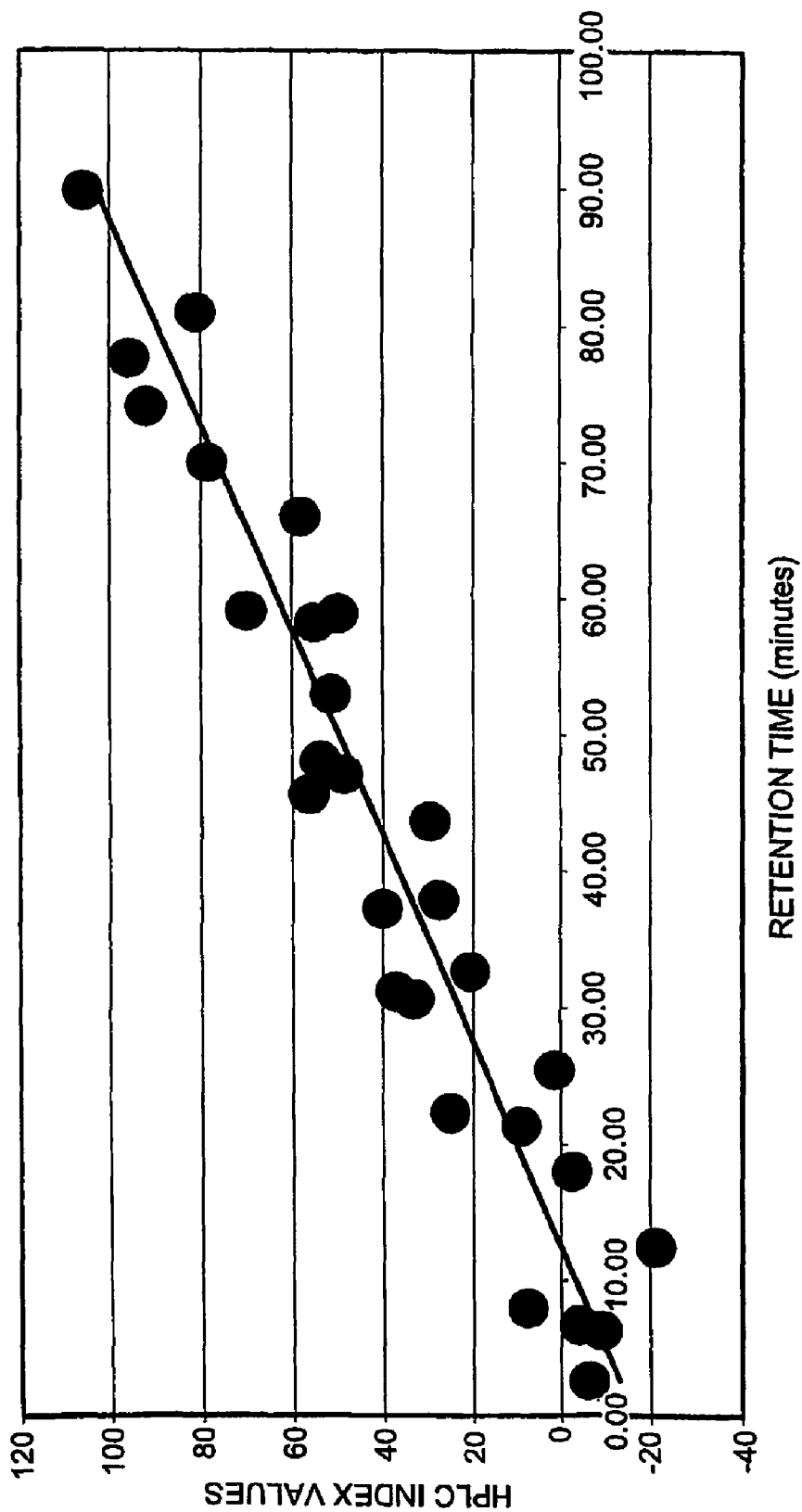
FIG. 2 shows hydrophobicity versus retention time on a reverse-phase HPLC column for a collection of tryptic fragments of bovine serum albumin (BSA) which may be used as an internal standard.

The retention times of all unique masses matching IRP peptides by accurate mass and charge state may then plotted vs. each peptides theoretical hydrophobicity resulting in a linear equation relating retention time to hydrophobicity (see FIG. 2). Having this equation allows an experimental hydrophobicity to be calculated for each experimentally derived unique mass's retention time in the Composite UML. Further, having already established the charge state rules allows a theoretical charge state for each peptide in the indexed non-redundant protein database to be calculated. Qualification may therefore involve ranking all experimentally derived physico-chemical properties to those theoretical physico-chemical properties of all peptides within an organism's Proteome. With respect to the $E.\ coli$ dataset these physico-chemical properties may be accurate mass, hydrophobicity and charge state. Before the qualification algorithm is applied, the Composite UML is accurate mass searched against the indexed non-redundant protein database. An accurate mass search can be considered to be a Peptide Mass Fingerprint. Here the user selects from and inputs a tolerance value for a list of different accurate mass search parameters. With respect to the E. coli dataset the accurate mass search parameters were set to: mass accuracy +/−10 ppm, minimum number of peptides to match 3, and missed cleavages=0. Other parameters could include sequence coverage, intact protein molecular weight range, intact protein pI, peptide pI, peptide modifications i.e. phosphates, sugars, and non-specific cleavages to name only a few. Further the user could select different parameters for different iterations as illustrated in the subtractive reiteration section. Here the Tentative Identification Algorithm applies the appropriate accurate mass search parameters for each iteration.

Frequency Generator

The Frequency Generator first annotates each Tentative Identification (TID) with the number of proteins hit under the user-defined tolerance windows for each physico-chemical property selected in the analysis process. For the E. coli example these Frequency Values were ($Freq_{AM}$, $Freq_{HPLCi}$, $Freq_{CS}$). The experimentally derived calculated $MH^+$ 1795.9523 @ RT 45.00 minutes with a calculated experimental charge-state of 2.90 hit 7 different proteins within the accurate mass tolerance of 10 ppm. However, three Tolerance Windows were selected for Accurate Mass, 0-5 ppm, 5-7.5 ppm and 7.5 to 10 ppm:

| Tolerance = 10 ppm Coefficients for $AM_{windows}$ | |
| --- | --- |
| x = 5 | 7.5 to 10 ppm |
| y = 2.5 | 5 to 7.5 ppm |
| z = 1 | 0 to 5 ppm |

As such the $Freq_{AM}$ was 5 for the 5 TIDs within the tolerance window 0-5 ppm, 6 for the tolerance window between 5-7.5 ppm and 7 for the tolerance window between 7.5-10 ppm. To further separate the ranking, each tentative identification (TID) receives a weighing factor based on which tolerance window that TID fell in. In this example, there is not that much of a difference between 5 hits and 7 seven hits however if a weighing factor is assigned to each tolerance window it is possible to further separate a high quality (<5 ppm) accurate mass TID from a lower quality (>7.5 ppm) one. As such, each tolerance window is assigned a user-defined weighing factor $AM_{Weighted}$ (x, y, and z as shown above). In this example, weighing factors of 1, 2.5 and 5 were assigned for tolerance windows 0-5 ppm, 5-7.5 ppm and 7.5-10 ppm respectively. Taking the product of $Freq_{AM}*AM_{Window}$ changes the score from 5, 6, 7 to 5, 15, 35 clearly distancing a lower quality TID from a higher quality one. (It will become clear later why a lower score is better). To further adjust the scoring another weighing factor $TIDS_{WeightedAM}$ may be included. This coefficient corrects the score by dividing each individual TID's $Freq_{AM}$ by that of the Maximum $Freq_{AM}$. For the present example, the calculated $TIDS_{WeightedAM}$ was 3.57 for those with $Freq_{AM}$'s of 5, 5.14 for that at 6 and 7 for the one with a $Freq_{AM}$ of 7. Since there is not that great a spread between how many proteins are tentatively identified at each tolerance window the coefficient $TIDS_{WeightedAM}$ does not impact the score as much as that of the $AM_{Window}$. Taking the product of $Freq_{AM}*AM_{Window}*TIDS_{WeightedAM}$ changes the score from 5, 15, 35 to 17.85, 77.1, 245. However, if there is only one TID, within tolerance window one, of any physico-chemical property selected for data reduction this coefficient clearly separates it from the rest of the pack. The final user-defined weighing factor for a particular physico-chemical property is the Weight that that property has on the final score, i.e. 50% of the total score is based on accurate mass, therefore the $AM_{weight}=\frac{1}{2}$:

| Coefficients for frequency weighting | |
| --- | --- |
| a = 6 | Weight_AM |
| b = 2 | Weight_HPLC |
| c = 2 | Weight_CS |

As such the AM value in the final Weighted Rank equation:

$$1/(AM+HPLC+CS) = (AM_{weighted}*AM_{Freq}*TIDS_{Weighted}*AM_{Window})$$

The same logic follows for all selected physico-chemical properties that were used for data reduction resulting in a final Weighted Rank of 0.1795 for two of the seven TIDs with the next closest scoring being 0.156. It should be noted that the two TIDs scoring 0.1795 are from the same peptide, derived from two isoforms of the same protein. To validate this Accurate Mass Physico-chemical Properties TID, the accurate mass and retention time were placed in an include list and MS/MS was performed. The MS/MS search results clearly and unambiguously assigned that unique mass to tufA and B.

There is an additional weighing factor, the "Probability Weighing Factor," a coefficient that is ordinarily set by default to one. When all TIDs matched only within the lowest Physico-chemical Tolerance Window, the following weighing factors are employed, indicating that there is a high probability that all TIDs are false positives:

AM=0.2
HPLCi=0.5
CS=0.33

In a reiterative searching system these may be unique masses that contain missed cleavages, point mutations, modifications etc. When this condition is met the probability value is multiplied by the user-defined coefficient.

It will be clear to one skilled in the art that other physico-chemical properties could be ranked as well. Such other physico-chemical properties could be Intact Protein Mw and pI, Peptide pI, and exact mass differences as they relate to peptide modifications, to name only a few.

As previously stated the Frequency Generator is simply a Ranking Algorithm resulting in each TID being assigned a Weighted Rank. The weighted rank can be extrapolated into a probability score, essentially assigning a probability to a certain accurate mass with a certain charge state eluting at a certain retention time to the best likely candidate peptide sequence in the non-redundant protein database. To further validate a TID the user preferably runs a Qualification Algorithm.

Qualification Algorithm

The Qualification Algorithm allows the user to set certain parameters for comparing and qualifying frequency annotated TIDs from any two-sample sets typically a Control and an Experiment. To activate the Algorithm the user first sets up the parameters for matching. In the tufA example from E. coli the qualification parameters were set to only those matching pairs with a mass error less than 5 ppm, a retention time difference of less than 2 minutes, an ABS Freq <=4 and a probability score >70%. First the Frequency annotated data is sorted by Protein, then by MH+, then by sample. Only those with matching pairs are passed. This is accomplished by further sorting by sequence, then by sample. Calculations are then made on mass and retention time differences and normalized area ratios. Calculations are always based on dividing the Experimental results by that of the Control.

Once this accomplished the software generates a ABS Freq for each matched pair. The ABS Freq is equal to the Min Value of $Freq_{AM}$, $Freq_{HPLCi}$ and $Freq_{CS}$. All matched pairs passing the user-defined qualification parameters are transferred to the IonMap Summary Report.

Targeted Tandem Mass Spectrometry for Orphan Peptide Ions from the Ion Mapping Experiment After generating ion maps as detailed in the preferred embodiment, there are typically several ions that exhibit good mass accuracy but fail to correlate with known proteins from a variety of protein and nucleotide databases. A list is generated for these "orphan" peptide ions. The list may then be submitted as an include list for performing a set of LC-MS/MS experiments. These experiments will provide orphan peptide ion fragmentation data, which can then be examined using de novo methods and/or database searching software to ascertain the identity of these peptides. The orphan peptides may then be correlated, with or without post-translational modifications, to their respective parent proteins.

Global Analysis

A global analysis attempts to identify every protein in a proteome or proteome subset. Further it provides a means of measuring the relative levels of these proteins in two or more proteome or proteome subsets. In its most simple form, two or more protein mixtures are chemically or enzymatically fragmented in a reproducible manner to form respective mixtures of peptides. These peptides are then separated and accurately mass measured in a LC-MS analysis procedure. The unique mass list generator algorithm extracts a comprehensive list of accurate masses associated with the peptides in these mixtures and measures the relative intensity of these peptides. A qualifying algorithm uses accurate mass information in combination with physico-chemical property information to identify the proteins in the original mixtures and to assign each unique mass list peptide to the protein from which it is derived. Furthermore, this process measures the relative level of each peptides present, which is proportional to the relative level of the protein from which the peptide is derived.

Those ions which do not satisfy user-specified redundancy and threshold criteria may be analyzed by LC-MS/MS to derive sequence information, which may be searched against protein or DNA data bases or analyzed using de novo sequencing methods to provide additional protein identification information. The global analysis process provides a comprehensive and reproducible description of the identified and unidentified proteins in two or more proteome or proteome subset samples, which may be used to illustrate the qualitative and quantitative differences in the protein composition of the samples.

Up/Down Regulation

This type of analysis allows the user to set a threshold value on protein or peptide expression level difference between two samples and only identify and qualify those peptide ions outside the user-defined pre-set threshold. This type of analysis is a subset of a global analysis.

Differential Analysis

This type of analysis allows the user to identify and qualify only those peptide ions that are unique to one of the two conditions (Control and Experiment). This type of analysis is a subset of a global analysis.

Post Translational Modifications

This type of analysis will only identify and report relative expression levels for post-translationally modified peptide ions. This type of analysis is a subset of a global analysis.

Protein Family

This type of analysis will only identify and report relative expression levels for protein(s) indicated by the user which serves to create an indexed subset database. This type of analysis is a subset of a Global Analysis.

Relative Stoichiometry

Since the global analysis process determines the relative levels of the proteins that have been identified and qualified, one can choose to compare the measured levels of these proteins against any user-defined protein that has also been identified and qualified. Furthermore, if quantitative stoichiometry is required, signature peptides for each protein can be synthesized and analyzed to develop MS ionization response factors that can be used to correct the relative area ratio measurements for response factor differences.

It will be apparent to one skilled in the art that if one can do a global analysis, one can perform any type of subset analysis.

The Identification and Quantitation Algorithm Setup

The identification and quantitation algorithm can be set up by the user to be a single or reiterative process. Through a user interface the user may select the number of Stringency Searches (iterations) and the number of PASSES (cycles of reiterative analysis) for MS (and MS/MS, if any) interrogations.

The user inputs how many PASSES are desired, and how many iterations of the identification and quantification algorithm to use for each PASS. Listed below are examples of some physicochemical properties for each iteration of each PASS. The interface preferably allows the user to control the searching algorithm by setting the stringency parameters for each iteration of each PASS.

| Parameter | Example(s) |
| --- | --- |
| Source | All taxonomies, Yeast, Human, E. coli, etc. |
| Proteolytic Enzyme | (User-defined) |
| Non Redundant database | Protein, Translated Genomic DNA |
| Sub-Cellular Location | ER, Golgi, Cytoplasm, etc. |
| Protein Molecular Weight Range* | Complete, 0-50, 50-100, >100, and Threshold |
| Protein Isoelectric Point Range* | Complete, 0-4, 4-8, 8-12 and Threshold |
| Peptide Molecular Range | Complete, Start and Stop Weight (kDa) and Threshold |
| Peptide Isoelectric Point Range* | Complete, 0-4, 4-8, 8-12 and Threshold |
| Number of Peptides Required for Match | User-defined |
| Mass Accuracy | User-defined |
| Number of Missed Cleavages | User-defined |
| Modifications | CAM, Phosphorylation, etc. |
| Non-Specific Cleavages | yes/no (if yes, choose: subtlisin, chymotrypsin etc.) |
| Point Mutations | yes/no (User-defined: substitution, deletion, etc.) |

Any or all additional Physico-chemical Properties not listed.
*User-defined values. The values illustrated are only examples.

Rules for Number of Missed Cleavages

Rules may be defined for missed cleavages based on the fact that any peptide that has a missed cleavage will have an extra basic residue between the N- and C-terminus, since trypsin preferentially cleaves peptide bonds after R and K. Accordingly:

1. If there is a 2+ peptide ion with no 3+ companion ion, there is likely to be no missed cleavage;

2. If there is a 2+ peptide ion with no 3+ companion ion, there may be one missed cleavage;
3. If there, is a 2+ peptide ion with no 3+ companion ion, there is unlikely to be two missed cleavages;
4. If there is a 2+ peptide ion and a 3+ companion ion, there is likely to be no missed cleavage;
5. If there is a 2+ peptide ion and the identified sequence has KP or RP then the 2+ peptide ion is likely to have a 3+ companion;
6. If there is a 3+ peptide ion with no 2+ companion it is likely to have one missed cleavage;
7. If there is a 3+ peptide ion with a 2+ companion ion then it is very likely to have one or two missed cleavages;
8. If there is a 3+ peptide ion with a 2+ companion ion then it is likely to have no missed cleavage.

Rules for Phosphorylation

Rules may be formulated to define some of the parameters one would need to include in order to qualify a peptide as being phosphorylated:
1. The peptide must have an amino acid that is susceptible to phosphorylation (serine, serine, tyrosine, histidine, aspartic acid);
2. The peptide ion should have a phosphorylated companion ion that is 79.9994 atomic mass units greater;
3. The peptide should have a phosphorylation motif (for example, . . . GXDP . . . );
4. The phosphorylated companion ion should elute earlier from the reverse phase $C_{18}$-column; and
5. The more hydrophobic the nonphosphorylated peptide ion, the greater the retention time difference compared to the phosphorylated companion.

Scoring Algorithm Alternative

A further algorithmic approach is illustrated below, by which values are assigned to each matched/correlated characteristic to derive a match score for proteins/peptides from a theoretical/calculated database of known peptides/proteins versus the experimental protein/peptide.

Algorithm

Part 1—Data Set Generation:
    Smooth, Center, and Lock Mass Correct
    Determine Charge State
    Calculate Molecular Mass
    Search Database to generate initial hit list of candidate protein/peptide matches Part 2—Scoring:
    Sort Hit List by Protein Mw
    increase score if protein Mw is within SEC tolerance by 2×
    decrease score if protein Mw is outside SEC tolerance by 0.5×
    Sort Hit List by Protein pI
    increase score if protein pI is within CEX/AEX tolerance by 2×
    decrease score if protein pI is outside CEX/AEX tolerance by 0.5×
    Sort Peptide Hits by ppm mass difference
    if ppm mass difference is within mass difference of lock mass corrected nearest internal standard increase score by 4×
    if ppm mass accuracy is within 5 ppm increase score by 3×
    if ppm mass accuracy is within 7.5 ppm increase score by 1.5×
    if ppm mass accuracy is within 10 ppm leave score as is
    if ppm mass accuracy is outside 10 ppm then decrease score by 0.5×
    Sort Peptide Hits by Bull & Breese Values
    if B&B is within ±1000 of internal standard increase score by 3×
    if B&B is within ±2000 of internal standard increase score by 2×
    if B&B is within ±3000 of internal standard, leave as is
    if B&B is outside ±3000 of internal standard decrease score by 0.5×
    Compare Peptide pI against internal standard
    increase score if pI is within user-defined tolerance of internal standard with respect to CEX/AEX separation by 2×
    decrease score if pI is outside user-defined tolerance of internal standard with respect to CEX/AEX separation by 0.5×
    Sort Peptide hits by missed cleavages
    if 2+ with no multiply charged companion ion(s) and 0 missed cleavages increase score by 3×
    if 2+ with no multiply charged companion ion(s) and 1 missed cleavages leave score as is
    if 2+ with no multiply charged companion ion(s) and 2 missed cleavages decrease score by 0.5×
    if 2+ ion with 3+ companion ion and no missed cleavage leave score as is
    if 2+ ion with 3+ companion ion and K/P or RP increase score by 1.5×
    if 2+ ion without 3+ companion ion and K/P or RP leave score as is
    if 3+ ion with one missed cleavage and no 2+ counterpart leave score as is
    if 3+ ion with one or two missed cleavages and there exists a 2+ counterpart increase score by 2×
    Sort by Histidine containing peptides
    if no "histidine" present leave score as is
    if "histidine" is present and there is a companion ion of a different charge state increase score 1.5×
    if "histidine" is present and there is a companion ion of a different charge state and no missed cleavages increase score by 3×
    if "histidine" is present and there is no companion ion of a different charge state leave score as is
    if multiple histidines or histidine in conjunction with one or multiple missed cleavages and no multiply charged companion ions increase score by 2×
    Sort by Cysteine containing peptides
    if "cysteine" is present and modified leave score as it is
    if "cysteine" is present and not modified and no other ion earlier in elution matches with a modified cysteine decrease score by 0.5×
    if "cysteine" is present and not modified and there is another ion earlier in elution which matches with a modified cysteine increase score by 2×
    if multiple cysteines are present and none are modified increase score by 2×
    Sort Met Ox
    if one or more "Met Ox" are present and there exists a later eluting ion which mass matches to the same sequence in which one or more methionies are not oxidized increase score by 2×
    Sum hits from all scans which pass a user-defined preset threshold (i.e. only scores exceeding the user-defined preset threshold will be passed)
    In cases of repeat ions (nearest two scans or number of scans defining a typical peak width) include only hit with the highest score
    Increase Final score as coverage increases
    Sort resulting Summary Hit List with Proteins in ascending order, Calculate Probability Score Part 3—Quantitation:
  Plot molecular masses for each Identified Protein including summed intensities for all isotopes and save resulting Ion Map
  Compare relative intensities of each Ion Map against that of the Control Protein
  Calculate pseudo-concentration level relative to internal control protein In the algorithm above, the database may be searched by any of a number of recognized methods or programs known to the skilled artisan. Exemplary such methods include but are not limited to those described by K. R. Clauser et al., *Anal. Chem.* 71:2871-2882 (1999); M. Mann, M. Wilm, *Anal. Chem.* 66:4390-4399 (1994); P. A. Pevzner et al., *Genome Res.* 11:290-299 (2001); J. A. Taylor, R. S. Johnson, *Rapid Comm. Mass Spec.*, 11:1067-1075 (1997); S. Altschul et al., *Nucl. Acids Res.* 25:3389-3402 (1997); and B. A. Gaeta, *Biotechniques* 28:436-440 (2000).

In accordance with the preferred embodiment there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)].

All amino-acid residue sequences are represented herein by formulae whose left to right orientation is in the conventional direction of amino-terminus to carboxy-terminus. A dash or ellipsis at the beginning or end of an amino acid residue sequence indicates a peptide bond to a further sequence of one or more amino acid residues.

Applications of Ion Mapping

The preferred embodiment may be used in a variety of applications e.g. drug discovery, patient diagnosis and monitoring.

Single Nucleotide Polymorphism (SNP) Discovery

Ion mapping could be used to identify polymorphisms in 2'-deoxy-5'-ribonucleic acid (DNA). DNA of interest would be collected from populations of eukaryotic or prokaryotic cells of interest, and subjected to amplification as described in the literature (Genome Res 1999 May; 9(5):499-505). Then, through the judicious use of restriction endonucleases, resulting fragments could by separated and their accurate masses recorded by single or multiple dimensions of high performance liquid chromatography in conjunction with mass spectrometry. Fragments of interest, shared by populations of interest, could be simultaneously collected, as not all of the column effluent would be directed into the source of the mass spectrometer. These collected pool would go through additional rounds of amplification, digestion, and Ion Mapping, to eventually identify the particular gene, or region thereof, that contained the polymorphism unique to the population of interest. Ultimately, if the specific sequence location of the polymorphism was desired, then the judicious application of the knowledge of the starting material's sequence (e.g. whole genome, entire chromosome(s), subsets thereof, specific genes, or subsets thereof), the choice of restriction enzyme(s), the elution time of the various fragments created in the series of digests, and their accurate masses would be used to calculate what the original sequence of the fragment must have been to have generated a fragment(s) of the observed retention time(s) and mass(es).

Genotyping

Ion Mapping could be used for genotyping. A single base extension (SBE) assay would be used, and this has been described previously in the literature (Clin Chem. 2001 February; 47(2):164-72). However, the advantage of the application of IonMapping to this existing technology would be realized in the parallelization of process. Multiple genes of interest could be amplified simultaneously; whereas the number of assays to determine the specific allele(s) and homozygote versus heterozygote, has been limited to the mass window of a given time of flight instrument or to the florescence or fluorescence polarization of a particular antibody conjugate(s), Ion Mapping would dramatically expand the number of assays which could be simultaneously detected. These nucleic acids would be separated by one or more dimensions of high performance liquid chromatography (HPLC), e.g. anion exchange chromatography followed by ion pair reversed-phase chromatography in conjunction with mass spectrometry. Only if the SBE assay had the potential of creating two or more nucleic acids of exactly the same mass (within the mass accuracy of the given IonMapping process), and exactly the same chromatographic retention time(s), would the two (or more) assays be unable to be simultaneously analyzed. Since such an potential conflict could be calculated in advance through the judicious use of the calculated mass(es) and retention time(s) of the extended nucleic acids, these interfering assays could be conducted in separate experiments, or the amplified regions changed to create non-interfering assays. In any case, the signal intensity generated by each extended nucleic acid on the mass spectrometer would be used as the basis for quantitative analysis, e.g. determination of zygosity Transcriptional Profiling Ion Mapping could be used for monitoring gene expression, commonly referred to as transcriptional profiling. This technique has been previously described in the literature (Science 270, 467-470, (1995), where the means of separation are arrays of complementary immobilized nucleic acids, and detection results when fluorescently labeled nucleic acids generated from in vivo or in vitro systems hybridize to these arrays and remain behind to fluoresce following removal of non-specific binding partners. Ion Mapping could be used as a superior substitute for both the separation and identification of the nucleic acids generated from the in viva and in vitro systems. These nucleic acids would be separated by one or more dimensions of high performance liquid chromatography (HPLC), e.g. anion exchange chromatography followed by ion pair reversed-phase chromatography in conjunction with mass spectrometry. The retention time(s) of the molecules, combined with knowledge of their accurate masses could be used to identify which transcripts, and a relative idea of amount of each, were present in the sample. The signal area and/or intensity generated by each would be used as the basis for quantitative comparison between samples. It would be possible to generate tagged versions of these nucleic acids that would permit the detection of these molecules by positive ion mode mass spectrometry, and this would improve both reliability and sensitivity.

Metabolomics

A method for identifying and quantifying metabolite profiles from all different types of clinical samples. The ion mapping of metabolites will be performed using similar techniques to those described in the preferred embodiment of this application. Two or more sets of clinical samples will be compared to identify and quantify metabolites. For example, drug metabolites will be extracted from clinical samples (treated vs non treated) using a plethora of chromatographic separation techniques. These samples will then be analyzed by liquid chromatography interfaced to mass spectrometry gain information on accurate chromatographic retention times, and accurate mass of the all the metabolites in the sample in order to generate ion maps. Additionally, physico-chemical properties of small molecule metabolites can be used to assist in the generation of these metabolite ion maps. Relative as well as absolute quantification information can be extracted from selected ion chromatogram (SIC) information generated by the LC/MS experiment. Relative quantification of metabolites will be performed by comparing SIC peak integration data of metabolite ion maps generated in different conditions (i.e., diseased vs. non-diseased, treated vs. non-treated, mutant vs. wild type). In order to perform absolute quantification of metabolites from their respective ion maps an known internal standard will be incorporated and a calibration curve will generated. This information can then used to obtain absolute quantification of all the metabolites in the ion map.

Peptidomics

A method for identifying and quantifying bioactive peptide profiles from all different types of biological samples. The ion mapping of peptides will be performed using similar techniques to those described in the preferred embodiment of this application. Two or more sets of biological samples will be compared to identify and quantify bioactive peptides. For example, bioactive peptides will be extracted from clinical samples (i.e., diseased vs. non-diseased, treated vs non treated and wild type vs. mutant) using a plethora of chromatographic separation techniques. These bioactive peptide samples will then be analyzed by liquid chromatography interfaced to mass spectrometry to gain information on accurate chromatographic retention times, and accurate mass of the all the peptides in the sample in order to generate peptide ion maps. Additionally, physico-chemical properties of these bioactive peptides such as mol. Wt., pI etc. can be used to further assist in the generation of these peptide ion maps. Relative as well as absolute quantification information can be extracted from Selected Ion Chromatogram ("SIC") information generated by the LC/MS experiment. Relative quantification of peptides will be performed by comparing SIC peak integration data of peptide ion maps generated under different conditions (i.e., diseased vs. non-diseased, treated vs. non-treated, mutant vs. wild type). In order to perform absolute quantification of peptides from their respective ion maps a known internal standard will be incorporated and a calibration curve will generated. This information can then used to obtain absolute quantification of all the bioactive peptides in the ion map.

Protein Profiling

A method of identifying and quantifying protein profiles from all different types of biological samples is contemplated. The ion mapping of intact proteins may be performed using similar techniques to those described in the preferred embodiment of this application. Two or more sets of biological samples may be compared to identify and quantify intact proteins. For example, intact proteins may be extracted from clinical samples (i.e., diseased vs. non-diseased, treated vs non treated and wild type vs. mutant) using a plethora of chromatographic separation techniques. These intact protein samples may then be analyzed by liquid chromatography interfaced to mass spectrometry to gain information on accurate chromatographic retention times and the accurate mass of the all the proteins in the sample in order to generate protein ion maps. Additionally, physico-chemical properties of these proteins such as mol. Wt., pI etc. can be used to further assist in the generation of these intact protein ion maps. Relative as well as absolute quantification information can be extracted from Selected Ion Chromatogram ("SIC") information generated by the LC/MS experiment. Relative quantification of intact proteins will be performed by comparing SIC peak integration data of protein ion maps generated under different conditions (i.e., diseased vs. non-diseased, treated vs. non-treated, mutant vs. wild type). In order to perform absolute quantification of proteins from their respective ion maps a known internal standard will be incorporated and a calibration curve will generated. This information can then used to obtain absolute quantification of all the intact proteins in the ion map.

The invention may be better understood by reference to the following non-limiting examples, which are provided by way of example only. The examples are presented in order to more fully illustrate the preferred embodiments of the invention and should not be construed as limiting the scope of the invention in any way.

EXAMPLES

General Procedures

All proteins and complex protein mixtures were suspended in 0.4 M ammonium bicarbonate buffer (pH 8.5) containing 8.0 M urea. Proteins were reduced by adding DTT to a final concentration of 4.5 mM and incubating at 50 degrees Celsius for 30 minutes. After reduction, cysteine residues were alkylated by the addition of iodoacetamide to a final concentration of 10 mM and incubating in darkness at room temperature for 30 minutes. The reaction was diluted with water to a final urea concentration of 2M, and trypsin was added to a final concentration of 4% (w/w, enzyme to that of protein) and incubated for 24 hours at 37 degrees Celsius. Acetic acid was added to a final concentration of 2% to terminate the trypsin digest.

Accurate Mass LCMS analysis was performed on an orthogonal acceleration Time of Flight mass spectrometer (Q-TOF 2, Micromass Ltd., Manchester UK) interfaced to a Waters CapLC HPLC System. The Q-TOF 2 was fitted with a custom triaxial sprayer that facilitated the co-addition of a solution of lock mass standard at the tip of the sprayer (inner diameter: chromatographic eluent, middle diameter: lockmass, outer diameter: nebulizing gas). A 2.0 picomole per microliter solution of [Glu$^1$]-Fibrinopeptide B was generally used as a lockmass standard. The instrument was operated in W-optics mode at 17,000 resolving power (FWHM definition). The Q-TOF 2 was set to acquire data over the 300 and 2000 mass-to-charge range. Spectral acquisition time was 1.9 seconds with an inter-scan delay of 0.1 second.

One hundred microliters of each sample was pipetted into a septum-capped vial and placed into a chilled (4° C.) autosampler plate of the CapLC. Five microliters of a 1.0 picomole/microliter solution of Leu-Enkaphlin was added as an internal standard to each vial to monitor injection reproducibility. Mobile phase A was 2% Acetic Acid/0.05% TFA/5% Acetonitrile and mobile phase B was 2% Acetic Acid/0.05% TFA/95% Acetonitrile. A 0.320×150 mm $C_{18}$ Waters Symmetry™ column was employed for on-line peptide separation with a gradient of 1-40% B in 120 minutes, 50-90% B in 1 minute, isocratic at 90% B for 15 minutes than back to initial conditions for 30 minutes prior to the next injection. The gradient was developed at a flow rate of 3.5 microliters per minute and the lock mass solution was added at a flow rate of 0.25 microliters per minute. All samples were run in triplicate with blanks inserted after each injection to insure there was no carryover from injection to injection.

A customized implementation of the Q-TOF 2 MassLynx software was used to lock mass correct and accurately mass measure to within +/−5 ppm the components within the mixtures of interest. In each spectra, isotopic cluster signal intensity from all the charge states associated with each component were collapsed into an intensity number corresponding to the MH+ monoisotopic ion corresponding to that component. The intensity of this accurate mass monoisotopic peak information was summed across the chromatographic elution profile of each component to quantify its abundance. This abundance measurement was further corrected relative to the abundance of internal standards spiked into the samples and/or to the abundance of one or more endogenous chemical components or polypeptides that was determined to be an appropriate internal standard. An endogenous chemical component or polypeptide qualifies as an internal standard if its abundance level relative to other specific chemical components or polypeptides in the mixture does not vary in a statistically significant manner when compared to the same chemical component or polypeptide abundance ratios in another sample mixture which is being compared quantitatively. The suitability of a chemical component as an endogenous internal standard can be tested according to the following equation:

$$(A_{IS}/A_{CC})_{control}/(A_{IS}/A_{CC})_{Experiment} \sim 1.0$$

where, $A_{IS}$ is the abundance of a candidate endogenous internal standard found in both the control sample and the experimental sample, and $A_{CC}$ is the abundance of a second component which is also common to both the control and experimental samples. If the ratio closely approximates one when the abundance of a candidate endogenous internal standard is tested against the abundance of a plurality of second components in the control and experimental samples, then it is a satisfactory endogenous internal standard.

This resulting accurate mass, intensity, charge state, and chromatographic retention time information was recorded for each chemical component or polypeptide into a compilation referred to as a Unique Mass List. Information from replicate analyses of the same mixture was retained in a compressed or composite Unique Mass List which combined the measured information in a statistically valid manner.

In the following qualitative identification examples, two physico-chemical properties, hydrophobicity and charge state, are used along with an accurate mass measurement to confirm the identity of an unknown polypeptide and hence the protein from which it came. For both physico-chemical properties, the closeness-of-fit between the measured and calculated values of these properties is used in combination with the corresponding accurate mass measurement to identify a given-unknown polypeptide. FIG. 2 illustrates the relationship between the observed retention time and the corresponding calculated hydrophobicity measurements for a mixture of known tryptic BSA peptides that were separated under the chromatographic conditions previously described. In this example, the HPLC Index value of a given peptide is a measure of its hydrophobicity based on its amino acid composition. Using BSA as an internal standard for each sample, the hydrophobicity relationship is used to estimate the HPLC Index value of unknown peptides in a complex peptide mixture. The identity of an unknown peptide in a complex mixture is determined by comparing on a best-fit basis the estimated HPLC Index value to the theoretical HPLC Index values of known peptides in an annotated peptide index that are within an acceptable mass error from the measured accurate mass. For example, peptides that match to within 15 units of the predicted HPLC Index value are scored with the highest probability and those, which match between 15 and 30 units, are scored lower.

If the identification of an unknown peptide cannot be made by the predicted hydrophobicity value and accurate mass information, then an additional physico-chemical property can be used to further reduce the number of possible candidate peptides to a single peptide identification. Such an additional physico-chemical property is charge state. More specifically, the measured charge state of an unknown peptide can be compared to the calculated charge state of a given peptide candidate from an annotated peptide index. The measured charge state (composite observed charge state) of a peptide is calculated according to the following formula:

$$\text{Composite Observed Charge State} = (C_1 * I_{C_1}) + (C_2 * I_{C_2}) + (Cn * I_{C_n})/(I_{C_1} + I_{C_2} + I_{C_n})$$

Where: $I_{C_n}$ equals the intensity of each charge state $C_n$ associated with each peptide.

The calculated charge state annotated to each peptide in the proteome subset associated with each sample of interest may be calculated according to the following rules.

For no internal basic residue/user-defined, if the peptide length <12 then the calculated charge state is in the range 2.00-2.05, if the peptide length is >12 and <17 then the calculated charge state is in the range 2.00-2.20, if the peptide length is >18 and <25 then the calculated charge state is in the range 2.00-2.30, and if the peptide has a length >25 then the calculated charge state is the range 2.50-3.00.

For one internal basic residue/user-defined residues (within 4 residues of N or C terminus), if the peptide length <12 then the calculated charge state is in the range 2.15-2.25, if the peptide length is >12 and <25 then the calculated charge state is in the range 2.00-2.25 or 2.75-3.00, and if the peptide has a length >25 then the calculated charge state is the range 2.00-2.35 or 2.85-3.00.

For two internal basic residues/user-defined residues (within 4 residues of N or C terminus), if the peptide length <12 then the calculated charge state is in the range 2.00-2.20 or 2.50-2.70, if the peptide length is >12 and <25 then calculated charge state is in the range 2.25-2.35 or 2.8-3.25, and if the peptide length is >25 then the calculated charge state is the range 2.30-2.50 or 3.00-4.00.

For three internal basic residues/user-defined residues (within 4 residues of N or C terminus), if the peptide length <12 then the calculated charge state is in the range 2.10-2.30 or 2.70-3.00, if the peptide length is >12 and <25 then the calculated charge state is in the range 2.25-2.50 or 3.00-3.50, and if the peptide length is >25 then the calculated charge state is the range 2.50-2.70 or 3.20-4.50.

Example 1

Analysis of a Single Protein (BSA)

Qualitative Analysis

To illustrate the ability to qualitatively identify a protein, one picomole of Bovine Serum Albumin trypsin digest was analyzed in triplicate by accurate mass LC-MS. The same solution was also analyzed on the Q-TOF 2 operated in a conventional data dependent LC-MS-MS/MS mode of acquisition in an effort to validate the accurate mass LC-MS identifications. The accurate mass, intensity, charge state and chromatographic retention time for each peptide was compiled into a composite Unique Mass List representing the measurements made from the three replicate analyses. This list is illustrated in FIG. 6. The criteria used for matching peptides in replicate injections were that accurate mass tolerance must be within +/−5 ppm from the average, retention time tolerance +/−2 minutes from the average, and charge state tolerance +/−0.35.

The resulting composite UML was then matched against an indexed peptide database created for the protein Bovine Serum Albumin (BSA). This database is illustrated in FIGS. 7A and 7B. The indexing algorithm was set to report only tryptic peptides consistent in mass to charge ratio with the mass measurement range employed on the Q-TOF 2 (m/z 300 to 2000) and having one or no missed cleavages. The indexing algorithm calculated and annotated each peptide with the accurate mass of its $MH^+$ ion, its HPLC index as a measure of hydrophobicity (Browne, C. A., Bennet, H. P. J. and Solomon S. (1982) *Anal. Biochem.* Vol. 124, pp. 201), peptide pI, number and position of missed cleavages, number and position of basic residues, peptide length, frequency index value, and amino acid sequence, as well as intact protein molecular weight and pI. The frequency index value represented the number of peptides in the entire Indexed Database that have a mass within +/−5 ppm of that peptide. The Indexed Database for BSA contains 99 peptides. None of these peptides are isobaric at the +/−5 ppm level. FIG. 8 illustrates the Unique Mass List $MH^+$ ions that were experimentally measured and matched to the BSA indexed database. A total of 27 ions were matched on the basis of their accurate mass, hydrophobicity, and charge state to provide 64% sequence coverage of the BSA protein. The identity of 11 of these 27 peptides which were assigned on the basis of their accurate mass and physical chemical properties was also confirmed by LC-MS-MS/MS.

Figure 3:
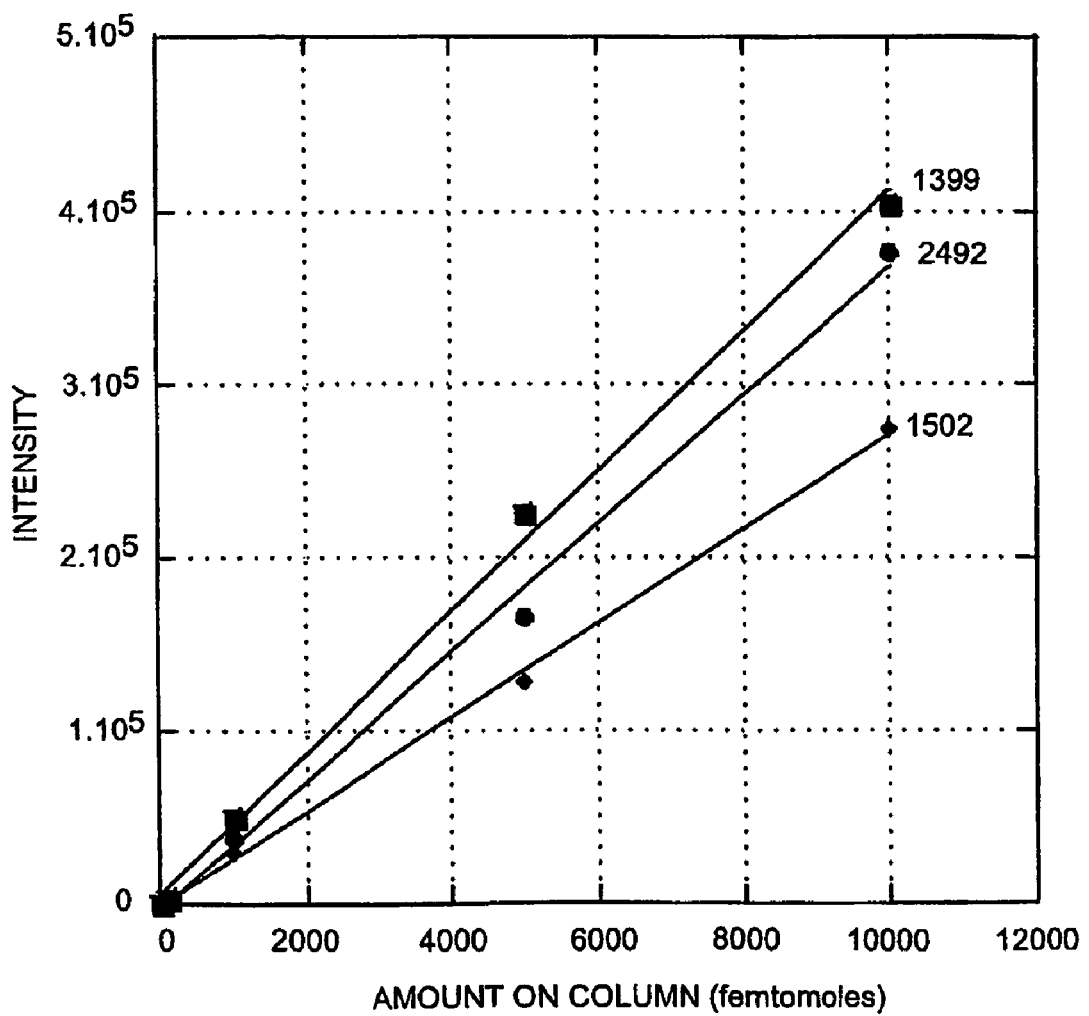
FIG. 3 shows plots of ion intensity versus amount of BSA introduced to the spectrometer for three fragment peptide ions.

The BSA single protein mixture was also used to evaluate the dynamic range and quantitative reproducibility of the sample handling and analysis procedure. Accordingly, intact Bovine Serum Albumin was suspended to concentrations of 10, 100, 1000, 5000, and 10,000, femtomoles per microliter in an Ambic/Urea buffer. These five samples were independently reduced with DTT, the cysteines were derivatized with iodoacetimide and each was digested overnight at 37° C. with trypsin as previously described. Triplicate injections were made of concentration of digested BSA. The resulting mass chromatograms were processed as previously described and the signal intensity for the peptides with MH+ ions at mass 1399.6931, 1502.6189, and 2491.2649 are plotted as a function of concentration in FIG. 3. The dynamic range of each peptide was linear over three orders of magnitude. The linearity of response also illustrates that the digestion chemistry and mass measurement process is reproducible.

Example 2

Analysis of a 14-Peptide Mixture

Qualitative Analysis—Simple Mixture

To illustrate the ability of the method to qualitatively identify all proteins in a moderately complex mixture, a model system of fourteen proteins consisting of the commercially available proteins listed in FIG. 4 was constructed. All proteins were used without further purification. Stock solutions of each protein were made up in an Ambic/Urea buffer at a concentration of 150 picomoles/microliter (per the vendors' weights). Volumes of these stock solutions were then assembled to create two different mixtures as defined in FIG. 4. Once assembled each mixture was diluted with varying volumes of Ambic/Urea to keep the final volumes constant. Each mixture was reduced with DTT; cysteine residues were derivatized with iodoacetamide, and each mixture digested independently at 37° C. overnight as previously described.

Each mixture was subjected to the same LC-MS accurate mass analysis previously described and data was processed as previously described.

Assuming up to one missed cleavage, a total of 487 peptides were calculated to be theoretically possible from the tryptic digestion of the 14 protein mixture. The accurate mass analysis of Mixture A produced a total of 125 peptides that were matched against this theoretical database. Sequence coverage ranged as high as 67% for the proteins in the mixture. The observed versus calculated accurate mass and physico-chemical property information for these 125 peptides is illustrated in FIGS. 9A-F.

Quantitative Analysis—14 Protein Mixture

FIG. 5 illustrates in a histogram format the measured versus theoretical relative abundance of the proteins in Mixtures B (bold) and A (shaded). The theoretical protein composition of both mixtures is illustrated in FIG. 4. The protein Fetuin was at the same concentration in both Mixtures A and B. A peptide associated with Fetuin was used as an endogenous internal standard to normalize quantitative comparisons between the two mixtures. All measured relative abundance values were within 20% of the theoretical abundance values thus illustrating the accuracy of the method for monitoring change in relative abundance of proteins or other chemical species contained in relatively complex mixtures.

Example 3

Analysis of a Bacterial Proteome

Bacterial Strains and Growth Conditions

Two 1 L cultures each of *Escherichia coli* strain MC4100 were cultured in M9 minimal medium supplemented with 0.2% glucose simultaneously one at the permissive temperature of 37° C. (MCLT) the other at the non-permissive temperature of 42° C. (MCHT). Cells were grown to mid-logarithmic phase (as determined by O.D. at 450 nm) and harvested by centrifugation in 500 mL tubes at 1000×g for 30 min at 4° C.

Cell Lysis and Digestion

Cells were lysed using a cocktail of 6M urea, 10 mM Tris, 1 mM DTT, pH 8.0, using gentle shaking for 20 min at 23° C. The cellular debris was then spun down at 20,000×g for 20 min. at 4° C., and the supernatant collected by pipette. The protein-laden supernatant was assayed for total protein concentration by bicinchoninic acid method of Smith et al. (*Anal. Biochem.* 150:74-85, 1985). This data was used to aliquot the supernatant into samples of 2.9 mg each of total protein. To each sample, 2.2 uL of 30 mg/mL bovine serum albumin (Sigma) in 8 M urea, 400 mM ammonium bicarbonate, pH 8.0 was added as a retention time standard to facilitate the calculation of HPLC Index values. Following mixing by vortex, each sample was chilled to 4° C. and chloroform/methanol precipitated. These pellets were dissolved in 8M urea, 400 mM ammonium bicarbonate, pH 8.0, and subjected to reduction (dithiothreitol, Sigma), alkylation (iodoacetamide, Sigma), and dilution to 200 uL. The samples were digested by the addition of 20 ug of porcine trypsin (Promega) overnight at 37° C. The samples were then diluted to a final volume of 1000 uL with the addition of water, bringing the final concentration of digested protein to ~60 pmol/uL, containing ca. 1 pmol/uL of BSA. These samples were aliquoted into polypropylene PCR tubes at 200 uL each, and stored at −80° C. until analyzed.

For illustrative purposes the low-temperature sample will be regarded as the control and the high-temperature sample as the experiment. Each sample was run in triplicate with the resulting Unique Mass Lists (UML) compressed into one Composite UML as previously described.

After compression the composite UML for the Control and Experiment samples contained 13,722 and 15,242 observed MH+ ions respectively. The abundance of these polypeptides were normalized to polypeptides associated with the proteins FTS1 and REC-C that were endogenous to both samples and determined to be unchanged by the conditions of the experiment. Each composite UML was matched on the basis of accurate mass and physico-chemical properties to an Indexed non-redundant E. coli database containing approximately 190,000 tryptic peptides (allowing for one missed cleavage) that correspond to the 4234 proteins believed to be contained in the E. coli proteome.

After applying accurate mass, hydrophobicity and charge state matching criteria, a total of 12,542 and 13,987 peptides were identified in the Control and Experimental samples, respectively that could be uniquely assigned to a proteins in the E. coli proteome. On the basis that a minimum of two peptides were required to qualify a protein identification, 2,985 proteins (70.5% of the proteome) were tentatively identified in the Control sample and 3,127 proteins (73.9% of the proteome) were tentatively identified in the Experimental sample. Comparison of the Control versus the Experimental resulted in 2,743 proteins being common to both conditions, 242 unique to the Control and 384 unique to the Experiment. Of the 2,743 proteins that were common to both samples, 2,249 proteins were observed to vary less than 150% in their relative abundance and 331 proteins were observed to change in their relative abundance by more than 150%, but less than 450%. A total of 163 of the proteins common to both mixtures were observed to change in their relative abundance by more than 450%.

Of particular interest to this study is the fact that the proteins GroEL and GroEs are two well characterized E. coli chaperone proteins that are known to be up-regulated when grown at non-permissive temperatures. Both of these proteins were identified in the mixtures and these identifications were confirmed by subsequent data dependent LC-MS-MS/MS analysis. The data illustrated a 3.0 and 6.1 fold increase in abundance of GroEL and GroEs proteins, respectively, in the Experimental sample versus the Control sample which is consistent with the expected change. The protein TufA, an elongation factor protein, was previously not known to be affected by temperature. However, it exhibited a 2.1 fold increase in relative abundance in the experimental sample. TufA further serves as an example of the quality of data that can be produced by the method. A total of 8 peptides were identified as TufA peptides providing 56% sequence coverage. The relative abundance of each of these peptides depicted a 2.1 fold change in expression with only an 8% coefficient of variation.

Rat Dose/Response Metabolism Study

A study was conducted with two rats dosed with a proprietary drug candidate. One rat was given a "low" dose of the drug and the second rat was given a "high" dose of the same drug. Urine samples were collected from both rats after a prescribed number of hours. Urine sample preparation consisted of dilution by a factor of four with double distilled water prior to accurate mass LC-MS analysis. LC-MS analytical conditions were as previously described. Both the low and high dose samples were analyzed in triplicate.

The compressed Unique Mass List for the high-dose and low-dose rat urine samples contained 2,674 and 2,827 unique masses, respectively. A total of 1,164 of these unique masses were found to be common to both the high and the low dose samples and could be matched on the basis of their accurate mass and retention time signatures. All component levels were normalized to a common chemical component that qualified as an endogenous internal standard as previously described. The relative abundance of all the components matched between the high dose and low dose samples were compared quantitatively. FIG. 10 illustrates a subset list of 27 of these matched metabolites that exhibited greater than 4-fold change in relative abundance. Statistical analysis of the triplicate results demonstrated that these quantitative measurements had a p-Score of less than 0.005. These results indicate that the method of the invention is an effective means of quantifying the relative abundance of chemical components in two complex metabolism samples. Furthermore, the example demonstrates that it is unnecessary to qualitatively identify the components of interest prior to being quantitatively compared.

The invention claimed is:

1. A method for analyzing differential expression of proteins in proteomes, comprising:
    a) providing a control sample comprising a complex mixture of proteins;
    b1) adding a protein standard to the complex mixture of proteins of the control sample;
    b2) digesting the complex mixture of proteins of the control sample, and the added protein standard, to form polypeptides fragmented from the proteins and the protein standard;
    b3) measuring a liquid chromatographic elution profile and a retention time for each polypeptide of the digest;
    b4) measuring a mass spectrometric signal intensity and an accurate mass and for each eluting polypeptide;
    b5) determining, from the measured elution profile and signal intensity, an abundance, summed over all isotopes and all charge states, for each polypeptide;
    b6) determining a relative abundance of each polypeptide, relative to the abundance of the internal standard, thereby correcting for variability of digestion efficiency;
    c) repeating steps (b1) through (b6) for an experimental sample in place of the control sample, the experimental sample having a similar biological origin to that of the control sample;
    d) matching polypeptides of the experimental sample with polypeptides of the control sample in response to accurate mass and chromatographic retention time meeting threshold criteria;
    e) comparing the relative abundance in the experimental sample to the relative abundance in the control sample of each matched polypeptide to determine one or more differentially expressed polypeptides that are above or below expression-level threshold criteria; and
    f) identifying proteins that correspond to the differentially expressed polypeptides in association with the measured retention times and accurate masses of the differentially expressed polypeptides.

2. A method as claimed in claim 1, wherein said complex mixture of proteins of the control sample comprises at least 1000 molecules having different identities.

3. A method as claimed in claim 1, wherein said first mixture and/or said second mixture comprise a nonequimolar heterogeneous complex mixture.

4. A method as claimed in claim 1, wherein the accurate mass is associated with a mass to charge ratio determined to within 20 ppm.

5. A method as claimed in claim 1, wherein the accurate mass is associated with a mass to charge ratio determined to within 0.01 mass units.

6. A method as claimed in claim 1, wherein said method further comprises:

measuring an ion mobility in gas phase for each polypeptide of the control sample and for each polypeptide of the experimental sample; and wherein matching polypeptides of the experimental sample with polypeptides of the control sample further comprises matching in response to ion mobility meeting the threshold criteria.

7. A method as claimed in claim 6, wherein said method further comprises:

measuring a charge state for each polypeptide of the control sample and for each polypeptide of the experimental sample; and wherein matching polypeptides of the experimental sample with polypeptides of the control sample further comprises matching in response to a same charge state.

8. A method as claimed in claim 1, wherein the mass spectrometric signal intensity and the accurate mass are analysed by a Time of Flight ("TOF") mass spectrometer.

9. A method as claimed in claim 1, wherein either: (i) said experimental sample is taken from a diseased organism and said control sample is taken from a nondiseased organism; (ii) said experimental sample is taken from a treated organism and said control sample is taken from a non-treated organism; or (iii) said experimental sample is taken from a mutant organism and said control sample is taken from a wild type organism.

* * * * *